US009771397B2

(12) United States Patent
Rybicki et al.

(10) Patent No.: US 9,771,397 B2
(45) Date of Patent: Sep. 26, 2017

(54) HPV CHIMAERIC PARTICLE

(71) Applicant: University of Cape Town, Cape Town (ZA)

(72) Inventors: Edward Peter Rybicki, Cape Town (ZA); Inga Isabel Hitzeroth, Cape Town (ZA)

(73) Assignee: University of Cape Town, Cape Town (ZA)

( * ) Notice: Subject to any disclaimer, the term of this patent is extended or adjusted under 35 U.S.C. 154(b) by 78 days.

(21) Appl. No.: 14/360,524

(22) PCT Filed: Dec. 3, 2012

(86) PCT No.: PCT/IB2012/056912
§ 371 (c)(1),
(2) Date: May 23, 2014

(87) PCT Pub. No.: WO2013/080187
PCT Pub. Date: Jun. 6, 2013

(65) Prior Publication Data
US 2014/0377367 A1   Dec. 25, 2014

(30) Foreign Application Priority Data

Dec. 1, 2011 (ZA) .............................. 2011/08841

(51) Int. Cl.
| C07K 14/005 | (2006.01) |
| C12N 7/00 | (2006.01) |
| A61K 39/12 | (2006.01) |
| A61K 39/00 | (2006.01) |

(52) U.S. Cl.
CPC ............ *C07K 14/005* (2013.01); *A61K 39/12* (2013.01); *C12N 7/00* (2013.01); *A61K 2039/5258* (2013.01); *A61K 2039/55566* (2013.01); *A61K 2039/575* (2013.01); *C12N 2710/20022* (2013.01); *C12N 2710/20023* (2013.01); *C12N 2710/20034* (2013.01); *Y10T 428/2982* (2015.01)

(58) Field of Classification Search
None
See application file for complete search history.

(56) References Cited

U.S. PATENT DOCUMENTS

| 7,407,807 B2 * | 8/2008 | Varsani ................ C07K 14/005 424/185.1 |
| 8,163,557 B2 * | 4/2012 | Varsani ................ C07K 14/005 424/186.1 |

FOREIGN PATENT DOCUMENTS

| WO | WO 00/09671 A | 2/2000 |
| WO | WO 03/068993 A | 8/2003 |
| WO | WO 03/097673 A | 11/2003 |
| WO | WO 2006/119516 A | 11/2006 |
| WO | WO 2010/147268 A | 12/2010 |
| WO | WO 2010/149752 A | 12/2010 |
| WO | WO 2011/077371 A | 6/2011 |
| ZA | WO 2011/077371 * | 6/2011 ........... A61K 39/295 |

OTHER PUBLICATIONS

Varsani et al. (Journal of Virology, 2003, p. 8386-8393).*
Mach et al. (Journal of Pharmaceutical Sciences, 2006, vol. 95, p. 2195-2206).*
Varsani, Arvind et al.: "Chimeric Human Papillomavirus Type 16 (HPV-16) L1 Particles Presenting the Common Neutralizing Epitope for the L2 Minor Capsid Protein of HPV-6 and HPV-16", *Journal of Virology*, vol. 77, No. 15, Aug. 2003, pp. 8386-8396.
Kondo, Kazunari et al.: "Modification of Human Papillomavirus-Like Particle Vaccine by Insertion of the Cross-Reactive L2-Epitopes", *Journal of Medical Virology*, vol. 80, pp. 841-846.
Kim, Hyoung Jin et al.: "One-step chromatographic purification of human papillomavirus type 16 L1 protein from *Saccharomyces cerevisiae*", *Protein Expression and Purification*, vol. 70, 2010, pp. 68-74.
Kim, Hyoung Jin et al.: "A Method for Removing Contaminating Protein during Purification of Human Papillomavirus Type 18 L1 Protein from *Saccharomyces cerevisiae*", *Archives of Pharmacal Research*, vol. 32, No. 12, 2009, pp. 1759-1766.
Rommel, Oliver et al.: "Heparan Sulfate Proteoglycans Interact Exclusively with Conformationally Intact HPV L1 Assemblies: Basis for a Virus-Like Particle ELISA", *Journal of Medical Virology*, vol. 75, 2005, pp. 114-121.
Embers, Monica, E. et al.: "Protective Immunity to Rabbit Oral and Cutaneous Papillomaviruses by Immunization with Short Peptides of L2, the Minor Capsid Protein", *Journal of Virology*, vol. 76, No. 19, Oct. 2002, pp. 9798-9805.
Gambhira, Ratish et al.: "Protection of Rabbits against Challenge with Rabbit Papillomavirus by Immunization with the N Terminus of Human Papillomarvirus Type 16 Minor Capsid Antigen L2", *Journal of Virology*, vol. 81, No. 21, Nov. 2007, pp. 11585-11592.
Kawana, Kei et al.: "Safety and immunogenicity of a peptide containing the cross-neutralization epitope of HPV16 L2 administered nasally in healthy volunteers", *Vaccine*, vol. 21, 2003, pp. 4256-4260.
Kondo, Kazunari et al,: "Neutralization of HPV16, 18, 31 and 58 pseudovirons with antisera induced by immunizing rabbits with synthetic peptides representing segments of the HPV16 minor capsid protein L2 surface region", *Virology*, vol. 358, 2007, pp. 266-272.
Slupetzky, Katharina et al.: "A papillomavirus-like particle (VLP) vaccine displaying HPV16 L2 epitopes induces cross-neutralizing antibodies to HPV11", *Vaccine*, vol. 25, 2007, pp. 2001-2010.

(Continued)

*Primary Examiner* — Agnieszka Boesen
(74) *Attorney, Agent, or Firm* — Haug Partners LLP

(57) ABSTRACT

This invention relates to a chimaeric human papillomavirus (HPV) virus like particle (VLP) having a diameter of about 30 nm. The invention further relates to methods of treatment and/or prophylaxis of HPV infection and/or cervical cancer by administration of the chimaeric HPV VLP of the invention to a subject.

13 Claims, 18 Drawing Sheets

(56) References Cited

OTHER PUBLICATIONS

Schellenbacher, Christina et al.: "Chimeric L1-L2 Virus-Like Particles as Potential Broad-Spectrum Human Papillomavirus Vaccines", *Journal of Virology*, vol. 83, No. 19, Oct. 2009, pp. 10085-10095.

Biemelt, Sophia et al.: "Production of Human Papillomavirus Type 16 Virus-Like Particles in Transgenic Plants", *Journal of Virology*, vol. 77, No. 17, Sep. 2003, pp. 9211-9220.

Christensen, Neil D. et al.: "Hybrid Papillomavirus L1 Molecules Assemble into Virus-like Particles That Reconstitute Conformational Epitopes and Induce Neutralizing Antibodies to Distinct HPV Types", *Virology*, vol. 291, 2001, pp. 324-334.

Rubio, Ivonne et al.: "Potent anti-HPV immune responses induced by tandem repeats of the HPV16 L2 (20-38) peptide displayed on bacterial thioredoxin", *Vaccine*, vol. 27, 2009, pp. 1949-1956.

Johnson, Katherine M. et al.: "Role of Heparan Sulfate in Attachment to and Infection of the Murine Female Genital Tract by Human Papillomavirus", *Journal of Virology*, vol. 83, No. 5, Mar. 2009, pp. 2062-2074.

Kim. Hyoung Jin et al.: "The Choice or Resin-Bound Ligand Affects the Structure and Immonogenicity of Column-Purified Human Papillomaviras Type 16 Virus-Like Particles", *PloS ONE*, Apr. 2012, vol. 7, Issue 4, pp. 1-12.

Pineo C., Plant production and immunogenic characterisation of Human papillomavirus chimaeric vaccines, Thesis presented for the degree of Master of Science in the Department of Molecular and Cell Biology, University of Cape Town, dated Aug. 2011. (Confirmation letter from the Deputy Director-Research & Learning Services at the Univerity of Cape Town).

English Translation of the Second Office Action issued in corresponding Japanese Application dated May 30, 2017.

* cited by examiner

SEQ ID NO: 1 – Amino acid sequence of HPV-16 L1

| | | | | | | |
|---|---|---|---|---|---|---|
| MSLWLPSEAT | VYLPPVPVSK | VVSTDEYVAR | TNIYYHAGTS | RLLAVGHPYF | PIKKPNNNKI | 60 |
| LVPKVSGLQY | RVFRIHLPDP | NKFGFPDTSF | YNPDTQRLVW | ACVGVEVGRG | QPLGVGISGH | 120 |
| PLLNKLDDTE | NASAYAANAG | VDNRECISMD | YKQTQLCLIG | CKPPIGEHWG | KGSPCTNVAV | 180 |
| NPGDCPPLEL | INTVIQDGDM | VDTGFGAMDF | TTLQANKSEV | PLDICTSICK | YPDYIKMVSE | 240 |
| PYGDSLFFYL | RREQMFVRHL | FNRAGAVGEN | VPDDLYIKGS | GSTANLASSN | YFPTPSGSMV | 300 |
| TSDAQIFNKP | YWLQRAQGHN | NGICWGNQLF | VTVVDTTRST | NMSLCAAIST | SETTYKNTNF | 360 |
| KEYLRHGEEY | DLQFIFQLCK | ITLTADVMTY | IHSMNSTILE | DWNFGLQPPP | GGTLEDTYRF | 420 |
| VTSQAIACQK | HTPPAPKEDP | LKKYTFWEVN | LKEKFSADLD | QFPLGRKFLL | QAGLKAKPKF | 480 |
| TLGKRKATPT | TSSTSTTAKR | KKRKL | | | | 505 |

Fig. 15

SEQ ID NO: 2 – Human-codon optimised HPV-16 L1 nucleotide sequence

| | | | | | | |
|---|---|---|---|---|---|---|
| atgtccctgt | ggctgcccag | cgaggccacc | gtgtacctgc | ccccgtgcc | cgtgagcaag | 60 |
| gtggtgagca | ccgatgagta | cgtggcccgg | accaacatct | actaccacgc | cggcacctcc | 120 |
| agactgctgg | ccgtgggcca | ccctacttc | cccatcaaga | agcccaacaa | caacaagatc | 180 |
| ctggtgccca | aggtgagcgg | cctgcaatac | cgggtgttca | gaatccacct | gcccgacccc | 240 |
| aataagttcg | gcttccccga | caccagcttc | tacaaccccg | acacccagag | actggtgtgg | 300 |
| gcctgcgtgg | gcgtggaggt | gggcagaggc | cagcctctgg | gcgtgggcat | cagcggccac | 360 |
| cctctgctga | acaagctgga | cgacaccgag | aacgccagcg | cctacgccgc | caacgccggc | 420 |
| gtggataaca | gagaatgcat | cagcatggac | tacaagcaga | cccagctgtg | cctcatcggc | 480 |
| tgcaagcccc | ccatcggcga | gcactgggc | aagggcagcc | cctgcaccaa | cgtggccgtg | 540 |
| aatcctggcg | actgtcctcc | cctggaactc | atcaacaccg | tgatccagga | cggcgacatg | 600 |
| gtggacaccg | gcttcggcgc | catggacttc | accaccctcc | aggccaataa | gagcgaggtg | 660 |
| cccctggaca | tctgcaccag | catctgcaag | taccccgact | acatcaagat | ggtgagcgag | 720 |
| ccctacggcg | atagcctgtt | cttctacctg | cggcgggagc | agatgttcgt | gcggcacctg | 780 |
| ttcaacagag | ccggcgccgt | gggcgagaac | gtgcccgacg | acctgtacat | caagggcagc | 840 |
| ggcagcaccg | ccaacctggc | cagcagcaac | tacttcccta | cccccagcgg | ctccatggtg | 900 |
| accagcgacg | cccagatctt | caacaagccc | tactggctcc | agagagccca | gggccacaac | 960 |
| aatggcatct | gctggggcaa | ccagctgttc | gtgaccgtgg | tggataccac | ccggagcacc | 1020 |
| aacatgtccc | tgtgcgccgc | catcagcacc | agcgagacca | cctacaagaa | caccaacttc | 1080 |
| aaggagtacc | tgaggcacgg | cgaggagtac | gacctccagt | tcatcttcca | gctgtgcaag | 1140 |
| atcaccctca | ccgccgacgt | gatgacctac | atccacagca | tgaacagcac | catcctggag | 1200 |
| gactggaact | tcggcctgca | gcccctcct | ggcggcaccc | tggaggacac | ctacagattc | 1260 |
| gtgaccagcc | aggccatcgc | atgccagaag | cacaccctc | ccgcccctaa | ggaggacccc | 1320 |
| ctgaagaagt | acaccttctg | ggaggtgaac | ctgaaggaga | agttcagcgc | cgacctggac | 1380 |
| cagttccctc | tgggcagaaa | gttcctgctg | caagccggcc | tgaaggccaa | gcctaagttc | 1440 |
| accctgggca | agagaaaggc | cacccccacc | acaagcagca | ccagcaccac | cgccaagcgg | 1500 |
| aagaagcgca | agctgtgata | g | | | | 1521 |

Fig. 16

SEQ ID NO: 3 – L2(108-120) epitope

LVEETSFIDA GAP          13

Fig. 17

SEQ ID NO: 4 – L2(56-81) epitope

```
GGLGIGTGSG TGGRTGYIPL GTRPPT                                              26
```

Fig. 18

SEQ ID NO: 5 – L2(17-36) epitope

```
QLYKTCKQAG TCPPDIIPKV                                                    20
```

Fig. 19

SEQ ID NO: 6 – L2 BPV(1-88) epitope

```
MSARKRVKRA SAYDLYRTCK QAGTCPPDVI PKVEGDTIAD KILKFGGLAI YLGGLGIGTW         60
STGRVAAGGS PRYTPLRTAG STSSLASI                                           88
```

Fig. 20

SEQ ID NO: 7 – Human-codon optimised L2(108-120) nucleotide sequence

```
ctggtggagg agaccagctt catcgacgcc ggagccccg c                             41
```

Fig. 21

SEQ ID NO: 8 – Human-codon optimised L2(56-81) nucleotide sequence

```
ggcggcctgg gcatcggcac cggcagcggc accgggggca ggaccggcta catccccctg        60
ggcaccagac cccccacc                                                      78
```

Fig. 22

SEQ ID NO: 9 – Human-codon optimised L2(17-36) nucleotide sequence

```
cagctgtaca agacctgcaa gcaggccggc acctgccccc ctgacatcat ccccaaggtg        60
```

Fig. 23

SEQ ID NO: 10 – Human-codon optimised L2 BPV(1-88) nucleotide sequence

```
atgagcgccc ggaagcgggt gaagcgggcc agcgcctacg acctgtaccg gacctgcaag    60
caggccggca cctgccccc tgacgtgatc cccaaggtgg agggcgacac aatcgccgac    120
aagatcctga agttcggcgg cctggccatc tacctgggcg gcctgggcat tggcacctgg   180
tccaccggca gagtggccgc tggaggaagc cctagataca ccccctgcg gaccgccgc    240
agcacaagca gcctggccag catctgatga                                    270
```

Fig. 24

SEQ ID NO: 22 – HPV 16 L1/L2(108-120) chimaeric polypeptide

```
MSLWLPSEAT VYLPPVPVSK VVSTDEYVAR TNIYYHAGTS RLLAVGHPYF PIKKPNNNKI    60
LVPKVSGLQY RVFRIHLPDP NKFGFPDTSF YNPDTQRLVW ACVGVEVGRG QPLGVGISGH   120
PLLNKLDDTE NASAYAANAG VDNRECISMD YKQTQLCLIG CKPPIGEHWG KGSPCTNVAV   180
NPGDCPPLEL INTVIQDGDM VDTGFGAMDF TTLQANKSEV PLDICTSICK YPDYIKMVSE   240
PYGDSLFFYL RREQMFVRHL FNRAGAVGEN VPDDLYIKGS GSTANLASSN YFPTPSGSMV   300
TSDAQIFNKP YWLQRAQGHN NGICWGNQLF VTVVDTTRST NMSLCAAIST SETTYKNTNF   360
KEYLRHGEEY DLQFIFQLCK ITLTADVMTY IHSMNSTILE DWNFGLQPPP GGTLVEETSF   420
IDAGAPACQK HTPPAPKEDP LKKYTFWEVN LKEKFSADLD QFPLGRKFLL QAGLKAKPKF   480
TLGKRKATPT TSSTSTTAKR KKRKL                                         505
```

Fig. 25

SEQ ID NO: 23 – HPV 16 L1/L2(56-81) chimaeric polypeptide

```
MSLWLPSEAT VYLPPVPVSK VVSTDEYVAR TNIYYHAGTS RLLAVGHPYF PIKKPNNNKI    60
LVPKVSGLQY RVFRIHLPDP NKFGFPDTSF YNPDTQRLVW ACVGVEVGRG QPLGVGISGH   120
PLLNKLDDTE NASAYAANAG VDNRECISMD YKQTQLCLIG CKPPIGEHWG KGSPCTNVAV   180
NPGDCPPLEL INTVIQDGDM VDTGFGAMDF TTLQANKSEV PLDICTSICK YPDYIKMVSE   240
PYGDSLFFYL RREQMFVRHL FNRAGAVGEN VPDDLYIKGS GSTANLASSN YFPTPSGSMV   300
TSDAQIFNKP YWLQRAQGHN NGICWGNQLF VTVVDTTRST NMSLCAAIST SETTYKNTNF   360
KEYLRHGEEY DLQFIFQLCK ITLTADVMTY IHSMNSTILE DWNFGLQPPP GGTGGLGIGT   420
GSGTGGRTGY IPLGTRPPTP LKKYTFWEVN LKEKFSADLD QFPLGRKFLL QAGLKAKPKF   480
TLGKRKATPT TSSTSTTAKR KKRKL                                         505
```

Fig. 26

SEQ ID NO: 24 – HPV 16 L1/L2(17-36) chimaeric polypeptide

```
MSLWLPSEAT VYLPPVPVSK VVSTDEYVAR TNIYYHAGTS RLLAVGHPYF PIKKPNNNKI    60
LVPKVSGLQY RVFRIHLPDP NKFGFPDTSF YNPDTQRLVW ACVGVEVGRG QPLGVGISGH   120
PLLNKLDDTE NASAYAANAG VDNRECISMD YKQTQLCLIG CKPPIGEHWG KGSPCTNVAV   180
NPGDCPPLEL INTVIQDGDM VDTGFGAMDF TTLQANKSEV PLDICTSICK YPDYIKMVSE   240
PYGDSLFFYL RREQMFVRHL FNRAGAVGEN VPDDLYIKGS GSTANLASSN YFPTPSGSMV   300
TSDAQIFNKP YWLQRAQGHN NGICWGNQLF VTVVDTTRST NMSLCAAIST SETTYKNTNF   360
KEYLRHGEEY DLQFIFQLCK ITLTADVMTY IHSMNSTILE DWNFGLQPPP GGTQLYKTCK   420
QAGTCPPDII PKVPAPKEDP LKKYTFWEVN LKEKFSADLD QFPLGRKFLL QAGLKAKPKF   480
TLGKRKATPT TSSTSTTAKR KKRKL                                         505
```

Fig. 27

SEQ ID NO: 25 – HPV 16 L1/L2 BPV(1-88) chimaeric polypeptide

```
MSLWLPSEAT VYLPPVPVSK VVSTDEYVAR TNIYYHAGTS RLLAVGHPYF PIKKPNNNKI      60
LVPKVSGLQY RVFRIHLPDP NKFGFPDTSF YNPDTQRLVW ACVGVEVGRG QPLGVGISGH     120
PLLNKLDDTE NASAYAANAG VDNRECISMD YKQTQLCLIG CKPPIGEHWG KGSPCTNVAV     180
NPGDCPPLEL INTVIQDGDM VDTGFGAMDF TTLQANKSEV PLDICTSICK YPDYIKMVSE     240
PYGDSLFFYL RREQMFVRHL FNRAGAVGEN VPDDLYIKGS GSTANLASSN YFPTPSGSMV     300
TSDAQIFNKP YWLQRAQGHN NGICWGNQLF VTVVDTTRST NMSLCAAIST SETTYKNTNF     360
KEYLRHGEEY DLQFIFQLCK ITLTADVMTY IHSMNSTILE DWNFGLQPPP GGTMSARKRV     420
KRASAYDLYR TCKQAGTCPP DVIPKVEGDT IADKILKFGG LAIYLGGLGI GTWSTGRVAA     480
GGSPRYTPLR TAGSTSSLAS I                                              501
```

Fig. 28

SEQ ID NO: 26 – Human-codon optimised DNA nucleotide sequence encoding the HPV 16 L1/L2(108-120) chimaeric polypeptide

```
atgagcctgt ggctgcccag cgaggccacc gtgtacctgc ccccgtgcc cgtgagcaag      60
gtggtgagca ccgatgagta cgtggcccgg accaacatct actaccacgc cggcacctcc    120
agactgctgg ccgtgggcca ccctacttc cccatcaaga agcccaacaa caacaagatc    180
ctggtgccca aggtgagcgg cctgcaatac cgggtgttca gaatccacct gcccgacccc    240
aataagttcg gcttccccga caccagcttc tacaaccccg acacccagag actggtgtgg    300
gcctgcgtgg gcgtggaggt gggcagaggc cagcctctgg gcgtgggcat cagcggccac    360
cctctgctga caagctgga cgacaccgag aacgccagcg cctacgccgc caacgccggc    420
gtggataaca gagaatgcat cagcatggac tacaagcaga cccagctgtg cctcatcggc    480
tgcaagcccc ccatcggcga gcactgggc aagggcagcc cctgcaccaa cgtggccgtg    540
aatcctggcg actgtcctcc cctggaactc atcaacaccg tgatccagga cggcgacatg    600
gtggacaccg gcttcggcgc catggacttc accaccctcc aggccaataa gagcgaggtg    660
cccctggaca tctgcaccag catctgcaag taccccgact acatcaagat ggtgagcgag    720
ccctacggcg atagcctgtt cttctacctg cggcgggagc agatgttcgt gcggcacctg    780
ttcaacagag ccggcgccgt gggcgagaac gtgcccgacg acctgtacat caagggcagc    840
ggcagcaccg ccaacctggc cagcagcaac tacttcccta cccccagcgg ctccatggtg    900
accagcgacg cccagatctt caacaagccc tactggctcc agagagccca gggccacaac    960
aatggcatct gctggggcaa ccagctgttc gtgaccgtgg tggataccac ccggagcacc   1020
aacatgtccc tgtgcgccgc catcagcacc agcgagacca cctacaagaa caccaacttc   1080
aaggagtacc tgaggcacgg cgaggagtac gacctccagt tcatcttcca gctgtgcaag   1140
atcaccctca ccgccgacgt gatgacctac atccacagca tgaacagcac catcctggag   1200
gactggaact cggcctgca gccccctcct ggcggcaccc tggtggagga ccagcttc      1260
atcgacgccg agccccgc atgccagaag cacacccctc ccgccctaa ggaggacccc     1320
ctgaagaagt acaccttctg ggaggtgaac ctgaaggaga gttcagcgc cgacctggac    1380
cagttccctc tgggcagaaa gttcctgctg caagccggcc tgaaggccaa gcctaagttc    1440
accctgggca agagaaaggc cacccccacc acaagcagca ccagcaccac cgccaagcgg    1500
aagaagcgca agctgtgata g                                              1521
```

Fig. 29

SEQ ID NO: 27 — Human-codon optimised DNA nucleotide sequence encoding the HPV 16 L1/L2(56-81) chimaeric polypeptide

```
atgagcctgt ggctgcccag cgaggccacc gtgtacctgc ccccgtgcc cgtgagcaag      60
gtggtgagca ccgatgagta cgtggcccgg accaacatct actaccacgc cggcacctcc    120
agactgctgg ccgtgggcca ccctactc cccatcaaga agcccaacaa caacaagatc      180
ctggtgccca aggtgagcgg cctgcaatac cgggtgttca gaatccacct gcccgacccc    240
aataagttcg gcttccccga caccagcttc tacaaccccg acacccagag actggtgtgg    300
gcctgcgtgg gcgtggaggt gggcagaggc cagcctctgg gcgtgggcat cagcggccac    360
cctctgctga caagctgga cgacaccgag aacgccagcg cctacgccgc caacgccggc    420
gtggataaca gagaatgcat cagcatggac tacaagcaga cccagctgtg cctcatcggc    480
tgcaagcccc ccatcggcga gcactggggc aagggcagcc cctgcaccaa cgtggccgtg    540
aatcctggcg actgtcctcc cctggaactc atcaacaccg tgatccagga cggcgacatg    600
gtggacaccg gcttcggcgc catggacttc accaccctcc aggccaataa gagcgaggtg    660
cccctggaca tctgcaccag catctgcaag tacccgact acatcaagat ggtgagcgag    720
ccctacggcg atagcctgtt cttctacctg cggcgggagc agatgttcgt gcggcacctg    780
ttcaacagag ccggcgccgt gggcgagaac gtgcccgacg acctgtacat caagggcagc    840
ggcagcaccg ccaacctggc cagcagcaac tactcccta ccccagcgg ctccatggtg      900
accagcgacg cccagatctt caacaagccc tactggctcc agagagccca gggccacaac    960
aatggcatct gctggggcaa ccagctgttc gtgaccgtgg tggataccac ccggagcacc   1020
aacatgtccc tgtgcgccgc catcagcacc agcgagacca cctacaagaa caccaacttc   1080
aaggagtacc tgaggcacgg cgaggagtac gacctccagt tcatcttcca gctgtgcaag   1140
atcaccctca ccgccgacgt gatgacctac atccacagca tgaacagcac catcctggag   1200
gactggaact tcggcctgca gccccctcct ggcggacag gcggcctggg catcggcacc   1260
ggcagcggca ccggggcag gaccggctac atccccctgg gcaccagacc ccccaccccc   1320
ctgaagaagt acaccttctg ggaggtgaac ctgaaagaga agttcagcgc cgacctggac   1380
cagttccctc tgggccggaa gttcctgctc caggctgggc tgaaggccaa gcccaagttc   1440
accctgggca gcggaaggc cacccccacc acctccagca ccagcaccac cgccaagcgg   1500
aagaaacgga agctgtgatg a                                              1521
```

Fig. 30

SEQ ID NO: 28 — Human-codon optimised DNA nucleotide sequence encoding the HPV 16 L1/L2(17-36) chimaeric polypeptide

```
atgagcctgt ggctgcccag cgaggccacc gtgtacctgc ccccgtgcc cgtgagcaag      60
gtggtgagca ccgatgagta cgtggcccgg accaacatct actaccacgc cggcacctcc    120
agactgctgg ccgtgggcca ccctactc cccatcaaga agcccaacaa caacaagatc      180
ctggtgccca aggtgagcgg cctgcaatac cgggtgttca gaatccacct gcccgacccc    240
aataagttcg gcttccccga caccagcttc tacaaccccg acacccagag actggtgtgg    300
gcctgcgtgg gcgtggaggt gggcagaggc cagcctctgg gcgtgggcat cagcggccac    360
cctctgctga caagctgga cgacaccgag aacgccagcg cctacgccgc caacgccggc    420
gtggataaca gagaatgcat cagcatggac tacaagcaga cccagctgtg cctcatcggc    480
tgcaagcccc ccatcggcga gcactggggc aagggcagcc cctgcaccaa cgtggccgtg    540
aatcctggcg actgtcctcc cctggaactc atcaacaccg tgatccagga cggcgacatg    600
gtggacaccg gcttcggcgc catggacttc accaccctcc aggccaataa gagcgaggtg    660
cccctggaca tctgcaccag catctgcaag tacccgact acatcaagat ggtgagcgag    720
ccctacggcg atagcctgtt cttctacctg cggcgggagc agatgttcgt gcggcacctg    780
ttcaacagag ccggcgccgt gggcgagaac gtgcccgacg acctgtacat caagggcagc    840
ggcagcaccg ccaacctggc cagcagcaac tactcccta ccccagcgg ctccatggtg      900
accagcgacg cccagatctt caacaagccc tactggctcc agagagccca gggccacaac    960
aatggcatct gctggggcaa ccagctgttc gtgaccgtgg tggataccac ccggagcacc   1020
aacatgtccc tgtgcgccgc catcagcacc agcgagacca cctacaagaa caccaacttc   1080
aaggagtacc tgaggcacgg cgaggagtac gacctccagt tcatcttcca gctgtgcaag   1140
atcaccctca ccgccgacgt gatgacctac atccacagca tgaacagcac catcctggag   1200
gactggaact tcggcctgca gcctcctcct ggcggcaccc agctgtacaa gacctgcaag   1260
caggccggca cctgcccccc tgacatcatc cccaaggtgc agccccaa agaggacccc   1320
ctgaagaagt acaccttctg ggaagtgaac ctgaaagaga agttcagcgc cgatctggac   1380
cagttccccc tcggccggaa gttcctgctc caggctggcc tgaaggccaa gcccaagttc   1440
accctgggca gaggaaggc cacccccacc acaagcagca ccagcaccac cgccaagcgg   1500
aagaaacgga agctgtgatg a                                              1521
```

Fig. 31

SEQ ID NO: 29 – Human-codon optimised DNA nucleotide sequence encoding the HPV 16 L1/L2 BPV(1-88) chimaeric polypeptide

```
atgagcctgt ggctgcccag cgaggccacc gtgtacctgc cccccgtgcc cgtgagcaag      60
gtggtgagca ccgatgagta cgtggcccgg accaacatct actaccacgc cggcacctcc     120
agactgctgg ccgtgggcca cccctacttc cccatcaaga agcccaacaa caacaagatc     180
ctggtgccca aggtgagcgg cctgcaatac cgggtgttca gaatccacct gcccgacccc     240
aataagttcg gcttccccga caccagcttc tacaaccccg acacccagag actggtgtgg     300
gcctgcgtgg gcgtggaggt gggcagaggc cagcctctgg gcgtgggcat cagcggccac     360
cctctgctga acaagctgga cgacaccgag aacgccagcg cctacgccgc caacgccggc     420
gtggataaca gagaatgcat cagcatggac tacaagcaga cccagctgtg cctcatcggc     480
tgcaagcccc ccatcggcga gcactggggc aagggcagcc cctgcaccaa cgtggccgtg     540
aatcctggcg actgtcctcc cctggaactc atcaacaccg tgatccagga cggcgacatg     600
gtggacaccg gcttcggcgc catggacttc accaccctcc aggccaataa gagcgaggtg     660
cccctggaca tctgcaccag catctgcaag taccccgact acatcaagat ggtgagcgag     720
ccctacggcg atagcctgtt cttctacctg cggcgggagc agatgttcgt gcggcacctg     780
ttcaacagag ccggcgccgt gggcgagaac gtgcccgacg acctgtacat caagggcagc     840
ggcagcaccg ccaacctggc cagcagcaac tacttcccta cccccagcgg ctccatggtg     900
accagcgacg cccagatctt caacaagccc tactggctcc agagagccca gggccacaac     960
aatggcatct gctggggcaa ccagctgttc gtgaccgtgg tggataccac ccggagcacc    1020
aacatgtccc tgtgcgccgc catcagcacc agcgagacca cctacaagaa caccaacttc    1080
aaggagtacc tgaggcacgg cgaggagtac gacctccagt tcatcttcca gctgtgcaag    1140
atcaccctca ccgccgacgt gatgacctac atccacagca tgaacagcac catcctggag    1200
gactggaact tcggcctgca gcctccccct ggcggcacca tgagcgcccg gaagcgggtg    1260
aagcgggcca gcgcctacga cctgtaccgg acctgcaagc aggccggcac ctgcccccct    1320
gacgtgatcc ccaaggtgga gggcgacaca atcgccgaca agatcctgaa gttcggcggc    1380
ctggccatct acctgggcgg cctgggcatt ggcacctggt ccaccggcag agtggccgct    1440
ggaggaagcc ctagatacac ccccctgcgg accgccggca gcacaagcag cctggccagc    1500
atctgatga                                                            1509
```

Fig. 32

HPV CHIMAERIC PARTICLE

This is application is a 371 of PCT/IB2012/056912 filed on Dec. 3, 2012, published on Jun. 6, 2013 under publication number WO 2013/080187 A and claims priority benefits of South African Patent Application Number 2011/08841 filed Dec. 1, 2011, the disclosure of which is incorporated herein by reference.

BACKGROUND OF THE INVENTION

This invention relates to a chimaeric human papillomavirus (HPV) virus like particle (VLP) having a diameter of about 30 nm and a method of treatment and/or prophylaxis of HPV infection and/or cervical cancer by administration of the chimaeric HPV VLP of the invention.

Cervical cancer is primarily caused by HPV infection and is the third most common cancer among women worldwide (Ferlay et al., 2010). As a result, HPV vaccine development is a priority for preventative cancer research. The L1 major capsid protein is the antigen of choice for prophylactic vaccines, as it is immunodominant and self-assembles into VLPs which are structurally and immunologically similar to authentic virions. Vaccination with VLPs elicits high titres of neutralisation antibodies (NAb) in both animals and humans and two multivalent HPV L1 VLP-based prophylactic vaccines have been licensed and are highly effective in the prevention of vaccine-type HPV-16 and 18 infections and associated disease (Schiller et al., 2008).

Despite the high efficacy of current L1 VLP-based HPV vaccines, the type-specificity (Brown et al., 2009; Wheeler et al., 2009), the lack of therapeutic efficacy (FUTURE II Study Group, 2007; Hildersheim et al., 2007) and the high cost of vaccines (Schiller et al., 2008) have limited their widespread application, particularly in developing countries with >80% of the cervical cancer burden (Parkin and Bray, 2006). Therefore, there is an urgent need for affordable second generation HPV vaccines, which broaden protection to include multiple oncogenic HPV types, and improve the therapeutic efficacy to clear established HPV infections and cancerous lesions.

Broad-spectrum prophylactic HPV vaccines can be developed using cross neutralising L2 epitopes. The L2 epitopes can be incorporated into surface regions of L1 to create L1/L2 chimaeras displaying the L2 peptide on the surface of assembled L1 (WO 03/097673; Kawana et al., 1999, 2003; Slupetzky et al., 2007; Kondo et al., 2007, 2008).

The use of plant expression systems for the large-scale production of foreign antigens has been proposed as a cost-effective alternative for vaccine production (Fischer et al., 2004), with a definitive trend toward the use of transient expression for high-level protein expression and optimisation (Rybicki, 2009). Several groups have expressed HPV-16 L1 in plants (Biemelt et al., 2003; WO 2006/119516; Maclean et al., 2007).

A practical limitation of plant systems is low yields of recombinant protein, potentially a result of protein instability or low-level expression (Fischer et al., 2004; Obembe et al., 2011). It is estimated that plant-expressed recombinant protein yields need to be greater than 1% of the total soluble protein (TSP) to be economically viable (Fischer et al., 2004). This is particularly problematic for the expression of recombinant proteins using nuclear-transformed transgenic plants, as these systems are often associated with low yields of recombinant protein (Rybicki, 2009).

HPV-16 L1 has been expressed transgenicaily in nuclear-transformed potato and tobacco plants, but low expression levels of HPV-16 L1 (<1% TSP) have consistently reported and the elicited immune responses were relatively weak (Biemelt et al., 2003; Varsani et al., 2003b; Varsani et al., 2006a).

However, human codon-optimisation of the L1 gene and targeting to the chloroplast have significantly improved HPV-16 L1 expression in both transgenic and *Agrobacterium*-mediated transient tobacco expression systems to up to about 17% TSP (Maclean et al., 2007).

A recent development in plant-derived HPV vaccines was the expression of the first HPV-16 L1 chimaera in plants. The L1/E6/E7 chimaera consisted of HPV-16 L1 C-terminally fused to several E6 and E7 epitopes and it was expressed in transgenic tomatoes (Paz De la Rosa et al., 2009). However, yields were low (0.05-0.1% TSP) and therefore not commercially viable.

WO 2011/077371 describes a method for producing chimaeric HPV L1 polypeptides with increased expression levels relative to HPV L1 protein in an insect, plant or yeast expression system. Although human codon-optimised L1/L2 chimaeras produced from HPV L1 and BPV L2 (amino acids 1-88) in plants formed VLPs of about 55 nm, the other HPV L1/L2 chimaeras were only able to form capsomeres of approximately 17 nm in diameter.

Although capsomeres are stable at room temperature, they are only able to induce 20 to 40-fold lower humoral immune responses in comparison to VLPs (Thönes et al., 2008). It would therefore be beneficial to develop a chimaeric VLP comprising L1 and L2 which is expressed at commercially viable levels in an expression system. Such a chimaeric VLP would be easier to purify and is likely to be more immunogenic than a chimaeric capsomere.

SUMMARY OF THE INVENTION

According to a first aspect of the invention there is provided a chimaeric human papillomavirus (HPV) virus like particle (VLP) having a size of about 30 nm in diameter, the chimaeric HPV VLP comprising a chimaeric HPV 16 L1/L2 polypeptide encoded by a human codon-optimised nucleotide sequence, the chimaeric HPV 16 L1/L2 polypeptide further comprising an HPV L1 polypeptide that includes an HPV L2 peptide of between about 13 amino acids to about 26 amino acids inserted from residue 414 of the HPV 16 L1 polypeptide, and wherein the amino acids of the inserted HPV L2 peptide replace the corresponding amino acids of the HPV 16 L1 polypeptide.

For example, the inserted HPV L2 peptide may be a 13 amino acid LVEETSFIDAGAP peptide (SEQ ID NO: 3) encoded by a human codon-optimised nucleotide sequence as set forth in SEQ ID NO: 7, or a 20 amino acid QLYK-TCKQAGTCPPDIIPKV peptide (SEQ ID NO: 5) encoded by a human codon-optimised nucleotide sequence as set forth in SEQ ID NO: 9, or a 26 amino acid GGLGIGTGS-GTGGRTGYIPLGTRPPT peptide (SEQ ID NO: 4) encoded by a human codon-optimised nucleotide sequence as set forth in SEQ ID NO: 8.

Preferably the inserted HPV L2 peptide is the 13 amino acid LVEETSFIDAGAP peptide (SEQ ID NO: 3) encoded by a human codon-optimised nucleotide sequence as set forth in SEQ ID NO: 7.

The HPV type 16 L1 protein may further be encoded by a nucleotide sequence modified to be nuclear localisation signal deficient.

Preferably, the HPV-16 L1/L2 polypeptide comprises an amino acid sequence as set out in SEQ ID NO: 22, SEQ ID NO: 23 or SEQ ID NO: 24, or a variant or derivative thereof.

Preferably, the HPV-16 L1 polypeptide is as set out in SEQ ID NO: 1 and the HPV-16 L1 polypeptide is encoded by a human-codon optimised HPV-16 L1 polynucleotide sequence as set out in SEQ ID NO: 2.

The approximately 30 nm diameter, chimaeric HPV VLP may be a plant expressed chimaeric HPV VLP purified from a plant expression system. Preferably, the expressed chimaeric VLP may be targeted to the chloroplast of the plant.

According to a further aspect of the invention, there is provided a pharmaceutical composition comprising a 30 nm diameter chimaeric HPV VLP according to the invention and a pharmaceutically acceptable carrier.

The composition may also comprise an adjuvant.

According to a further aspect of the invention, there is provided a method of producing a chimaeric HPV VLP having a size of about 30 nm in diameter, the method comprising the steps of:

(i) providing a chimaeric human codon-optimised nucleotide sequence encoding a chimaeric HPV 16 L1/L2 polypeptide, the chimaeric HPV 16 L1/L2 polypeptide comprising an HPV 16 L1 polypeptide having an HPV L2 peptide of between about 13 amino acids to about 26 amino acids inserted from residue 414 of the chimaeric HPV 16 L1/L2 polypeptide, wherein the amino acids of the inserted HPV L2 peptide replace the corresponding amino acids of the HPV 16 L1 polypeptide;

(ii) cloning the chimaeric human codon-optimised nucleotide sequence into an expression vector adapted to express a polypeptide in a plant;

(iii) transforming or infiltrating a plant cell with the expression vector of step (ii);

(iv) expressing the chimaeric HPV 16 L1/L2 polypeptide in the plant cell of step (iii) such that the expressed chimaeric HPV 16 L1/L2 polypeptide assembles into a chimaeric HPV VLP having a uniform shape and a diameter of about 30 nm; and (v) recovering the chimaeric HPV VLP from the plant cell.

The expression vector preferably includes promoters and other regulatory sequences, or the like, that are operably linked to the coding sequence of the expression vector.

Preferably, the expression vector of step (ii) is adapted to target a chloroplast of a plant cell and in step (iv) the expressed chimaeric HPV protein is targeted to the plant chloroplast.

Step (iii) may further include introducing into a plant cell a suppressor protein adapted to inhibit post-transcriptional gene silencing in a plant. Preferably, the suppressor protein is the NSs protein of the tomato spotted wilt virus or the p19 of tomato bushy stunt virus.

For example, the inserted HPV L2 peptide may be a 13 amino acid LVEETSFIDAGAP peptide (SEQ ID NO: 3) encoded by a human codon-optimised nucleotide sequence as set forth in SEQ ID NO: 7, or a 20 amino acid QLYKTCKQAGTCPPDIIPKV peptide (SEQ ID NO: 5) encoded by a human codon-optimised nucleotide sequence as set forth in SEQ ID NO: 9, or a 26 amino acid GGLGIGTGSGTGGRTGYIPLGTRPPT peptide (SEQ ID NO: 4) encoded by a human codon-optimised nucleotide sequence as set forth in SEQ ID NO: 8.

Preferably the inserted HPV L2 peptide is the 3 amino acid LVEETSFIDAGAP peptide (SEQ ID NO: 3) encoded by a human codon-optimised nucleotide sequence as set forth in SEQ ID NO: 7.

According to a further aspect of the invention, there is provided an approximately 30 nm diameter, chimaeric HPV VLP according to the invention for use in a method of preventing and/or treating HPV infection and/or cervical cancer in a subject.

More specifically, the chimaeric HPV VLP may be for use in a method of eliciting an immune response in the subject, such as a neutralising antibody and/or CTL response. Preferably, the chimaeric HPV VLP is for use in eliciting a cross-protective immune response to multiple HPV types in the subject.

According to a further aspect of the invention, there is provided a use of a regularly shaped, approximately 30 nm diameter, chimaeric HPV VLP according to the invention in the manufacture of a medicament for use in a method of preventing and/or treating HPV infection and/or cervical cancer in a subject.

More specifically, the medicament may be for use in a method of eliciting an immune response in the subject, such as a neutralising antibody and/or CTL response. Preferably, the medicament is for use in eliciting a cross-protective immune response to multiple HPV types in the subject.

According to a further aspect of the invention, there is provided a method of preventing and/or treating HPV infection and/or cervical cancer in a subject, the method comprising a step of administering a prophylactically or therapeutically effective amount of a uniformly shaped, approximately 30 nm diameter, chimaeric HPV VLP according to the invention to the subject.

More specifically, the method may comprise eliciting an immune response in the subject, such as a neutralising antibody and/or CTL response. Preferably, the method comprises eliciting a cross-protective immune response to multiple HPV types in the subject.

The subject is preferably a human.

(+)=plant-derived HPV-16 L1. The black arrows indicate the position of the L1/L2 chimaeras (~56 kDa) and the grey arrow indicates degraded protein.

Figure 3:
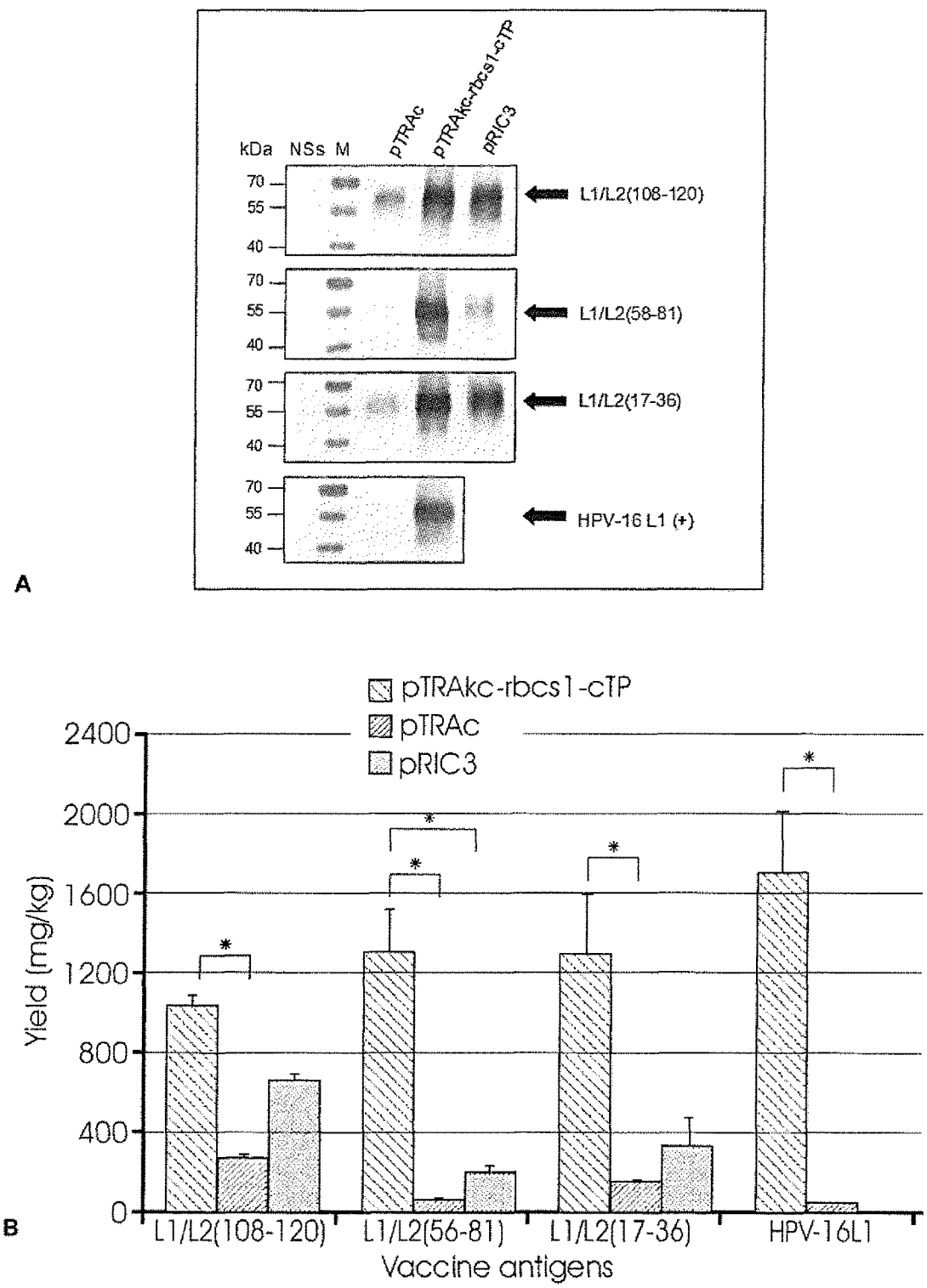

FIG. 3 *a*) shows a Western blot of the L1/L2 chimaeras expressed using 3 plant expression vectors: pTRAc, pTRAkc-rbcs1-cTP and pRIC3. Chimaeras were co-expressed with NSs, extracted 5 dpi and detected with CamVir1. HPV-16 L1 was expressed as a positive expression control for pTRAc and pTRAkc-rbcs1-cTP (pRIC3 construct not available) and the negative expression control was NSs-infiltrated plants. M=protein marker with the size of the protein indictated in kDa on the left. The black arrows indicate the L1/L2 chimaeras or HPV-16 L1 (~56 kDa); and b) shows comparison of the L1/L2 chimaeras expressed using 3 plant expression vectors: pTRAc, pTRAkc-rbcs1-cTP and pRIC3. The error bars indicate the standard deviation.

Figure 4:
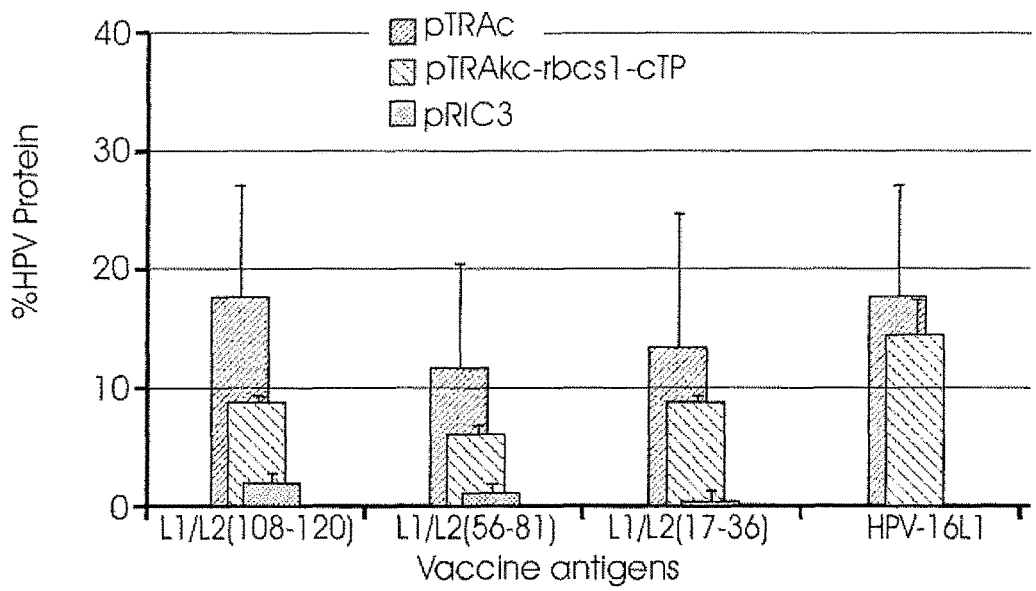

FIG. 4 shows assembly of L1/L2 chimaeras expressed using 3 different plant expression vectors: pTRAc, pTRAkc-rbcs1-cTP and pRIC3. Proteins were co-expressed with the NSs silencing suppressor and extracted 5 dpi. Chimaeras assembled into higher-ordered structures such as capsomeres or VLPs (detected by conformational-specific H16.V5 MAb) is expressed as a percentage of the total chimaera protein (detected by the linear-specific H16.J4 MAb). HPV-16 L1 was expressed as a positive expression control and the negative expression control was NSs-infiltrated plants. The error bars indicate the standard deviation.

Figure 5:
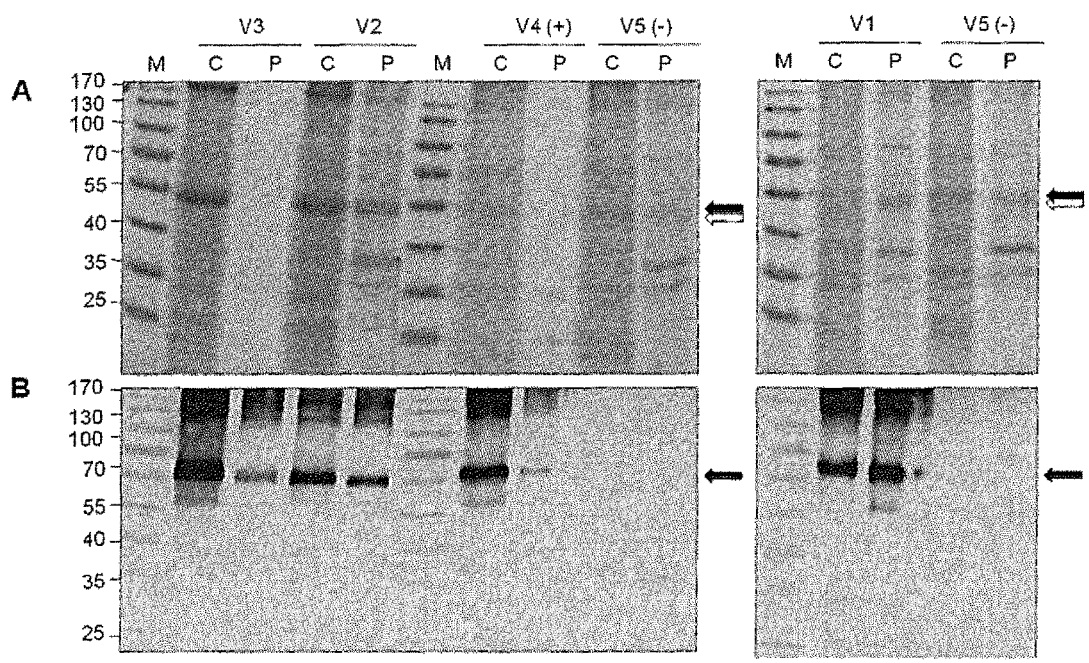

FIG. 5 shows purity of the plant-produced vaccine antigens. A) Coomassie-stained protein gel. B) Western blot detection of HPV antigens. M=Protein marker with size in kDa indicated on the left. C=clarified crude plant extract. P=purified antigen. V1=L1/L2(108-120), V2=L1/L2(56-81), V3=L1/L2(17-36), V4 (+)=HPV-16 L1 and V5 (−)=NSs-infiltrated plant extract. The black arrows indicate the HPV antigens and the white arrows indicate the plant protein Rubisco.

Figure 6:
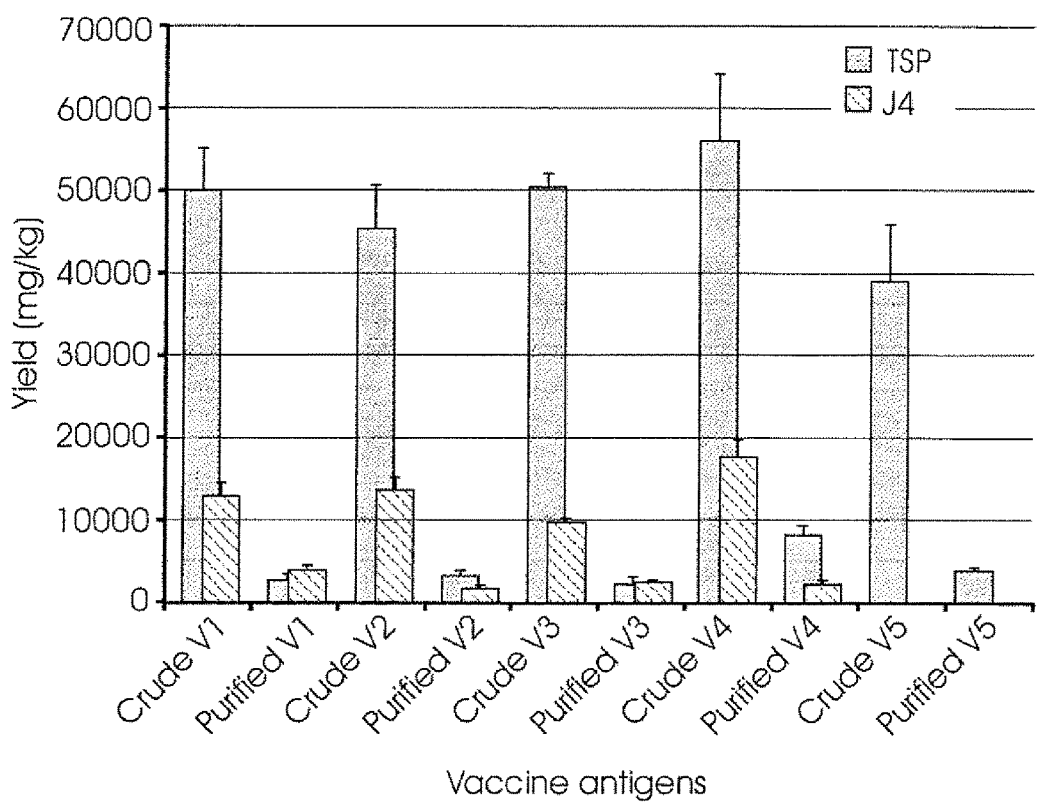

FIG. 6 shows total soluble protein (TSP) and total HPV protein in the crude and purified samples. TSP was determined using the Lowry assay and HPV protein was detected with H16 . . . 14 (linear epitope-specific). V1: L1/L2(108-120), V2: L1/L2(56-81), V3: L1/L2(17-36), V4: HPV-16 L1 (positive control), V5: NSs plant extract (negative control). The error bars indicate the standard deviation.

Figure 7:
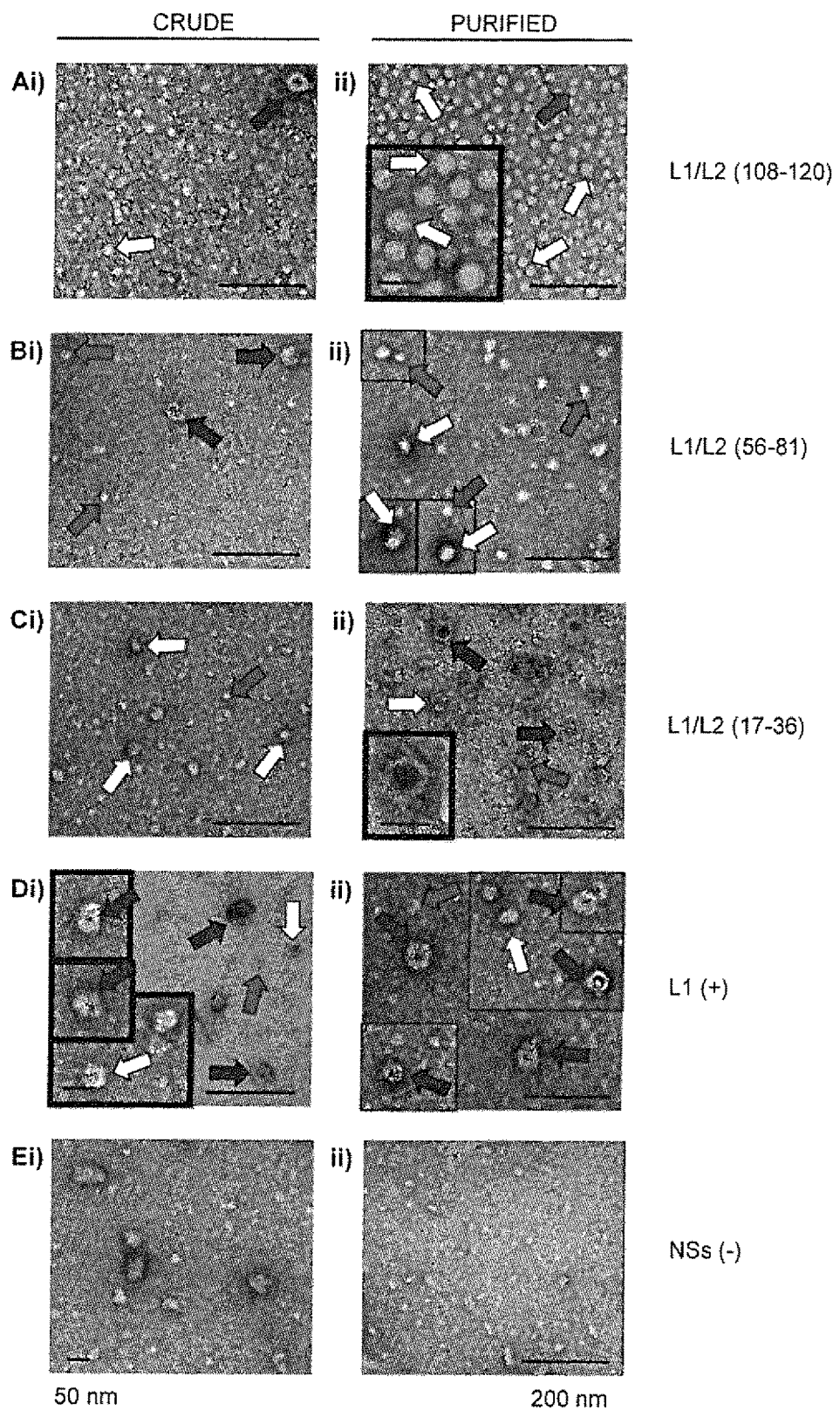

FIG. 7 shows transmission electron micrographs of CamVir1-immunotrapped crude and purified vaccine antigens A) V1: L1/L2(108-120), B) V2: L1/L2(56-81), C) V3: L1/L2(17-36), D) V4: HPV-16 L1 (positive control), E) V5: NSs plant extract (negative control). Grids were viewed on a Zeiss 912 Omega Cryo EFTEM. Left scale bar=50 nm, right scale bar=200 nm. Light grey arrows indicate HPV-16 capsomeres (~10 nm), white arrows represent capsomere aggregates or small VLPs (~30 nm) and dark grey arrows indicate full-sized VLPs (~55 nm).

Figure 8:
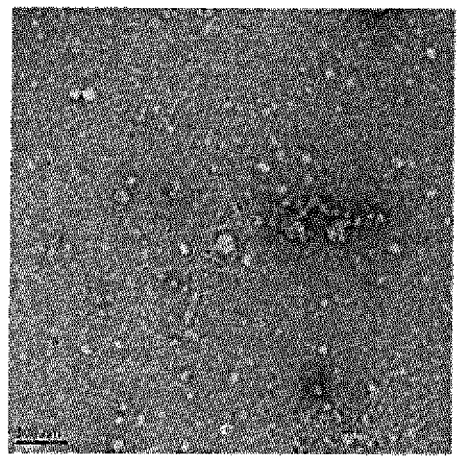

FIG. 8 shows a transmission electron micrograph of CamVir1-immunotrapped crude vaccine antigen L1/L2(56-81). Grids were viewed on a Zeiss 912 Omega Cryo EFTEM. Scale bar=100 nm.

Figure 9:
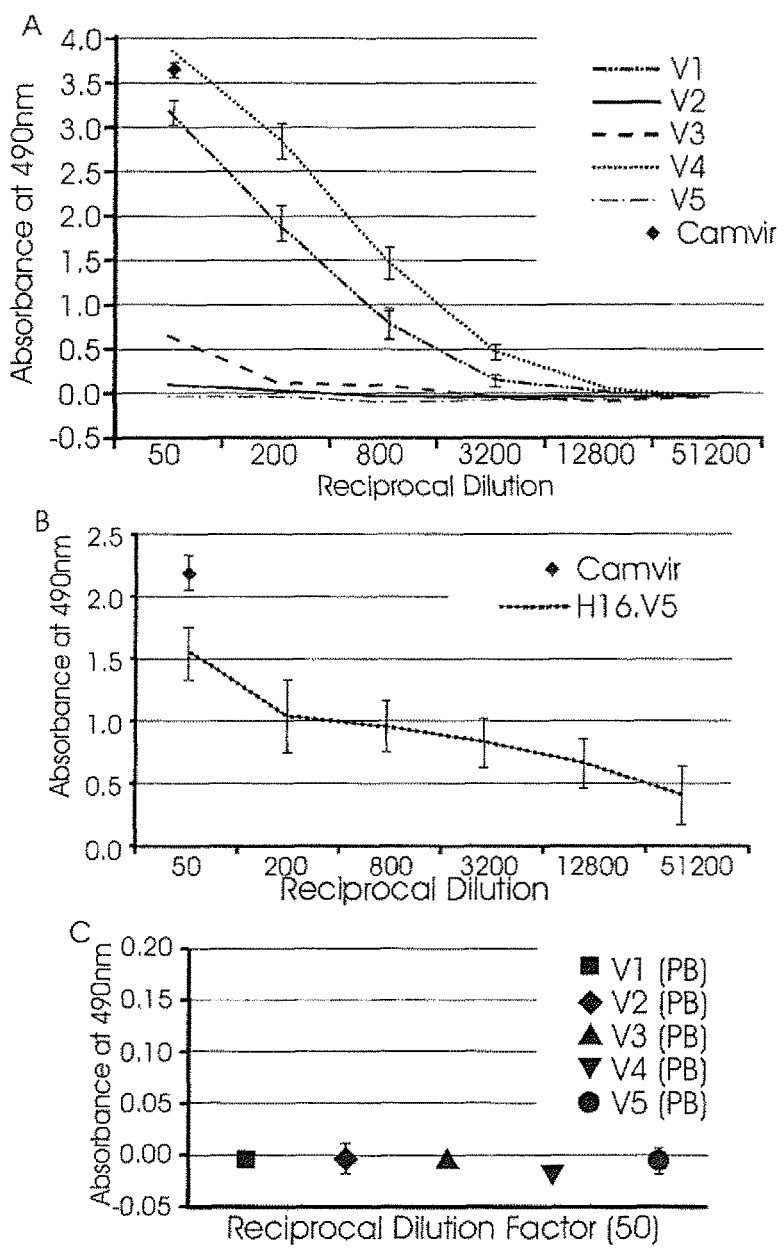

FIG. 9 shows a direct ELISA of mouse sera using insect cell-produced HPV-16 L1 as the coating antigen. V1=L1/L2(108-120), V2=L1/L2(56-81), V3=L1/L2(17-36), V4=HPV L1 (+vaccine control), V5=plant extract (−vaccine control). A) Titration of the mouse antisera for all the vaccines. B) Graph showing the values obtained for the ELISA positive control MAbs H16.V5 and CamVir1. C) Vaccine pre-bleed absorbance values at 1:50 dilution. Markers represent the mean value of triplicate samples and error bars indicate the standard deviation.

Figure 10:
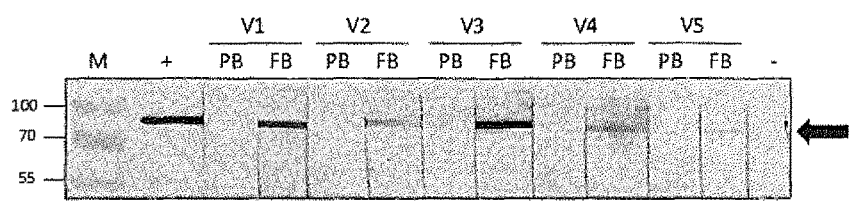

FIG. 10 shows a western blot detection of *E. coli*-expressed His-tagged HPV-16 L2 by mouse sera at a dilution of 1:100. M=protein marker with the protein size in kDa. V1=L1/L2(108-120), V2=L1/L2(56-81), V3=L1/L2(17-36), V4=HPV L1 (+vaccine control), V5=plant extract (−vaccine control). PB=pre-bleed sera. FB=final bleed sera. For the western blot controls: +ve=mouse anti-H is (1:2000; Serotec), −ve=no primary antibody. The black arrow indicates L2 (~80 kDa).

Figure 11:
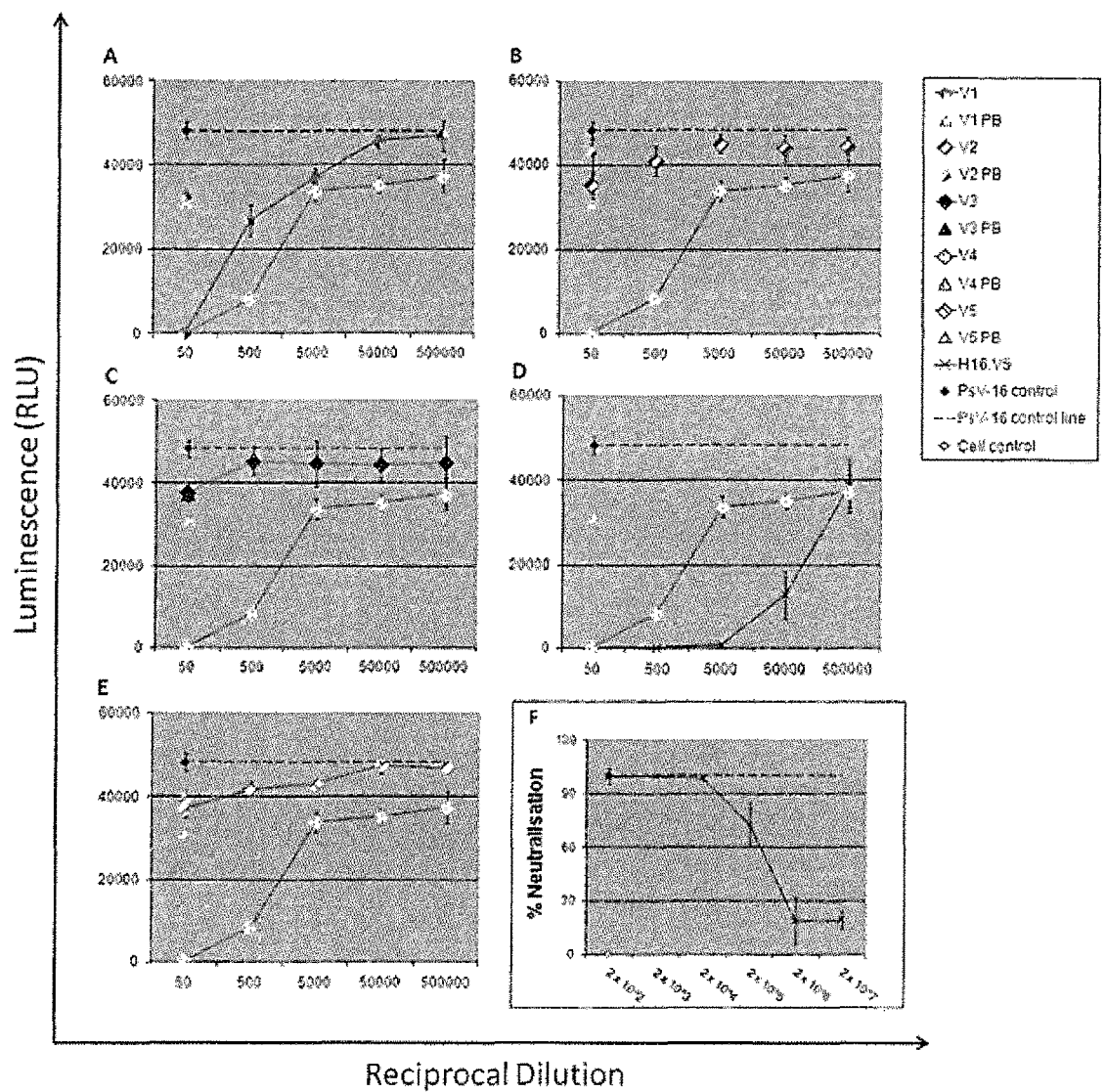

FIG. 11 shows a HPV-16 PsV neutralisation assay. Pooled sera from mice vaccinated with V1-V5 were tested for their ability to neutralise HPV-16 PsVs. A) V1=L1/L2(108-120), B) V2=L1/L2(56-81), C) V3=L1/L2(17-36), D) V4=HPV-16 L1 (+ve vaccine control), E) V5=NSs-infiltrated plant extract (−ve vaccine control). F) H16.V5=+ve neutralisation control. Cell control=−ve infection/SEAP expression control. PsV control=+ve infection/SEAP expression control. Samples were assayed in triplicate and error bars indicate the standard deviation.

Figure 12:
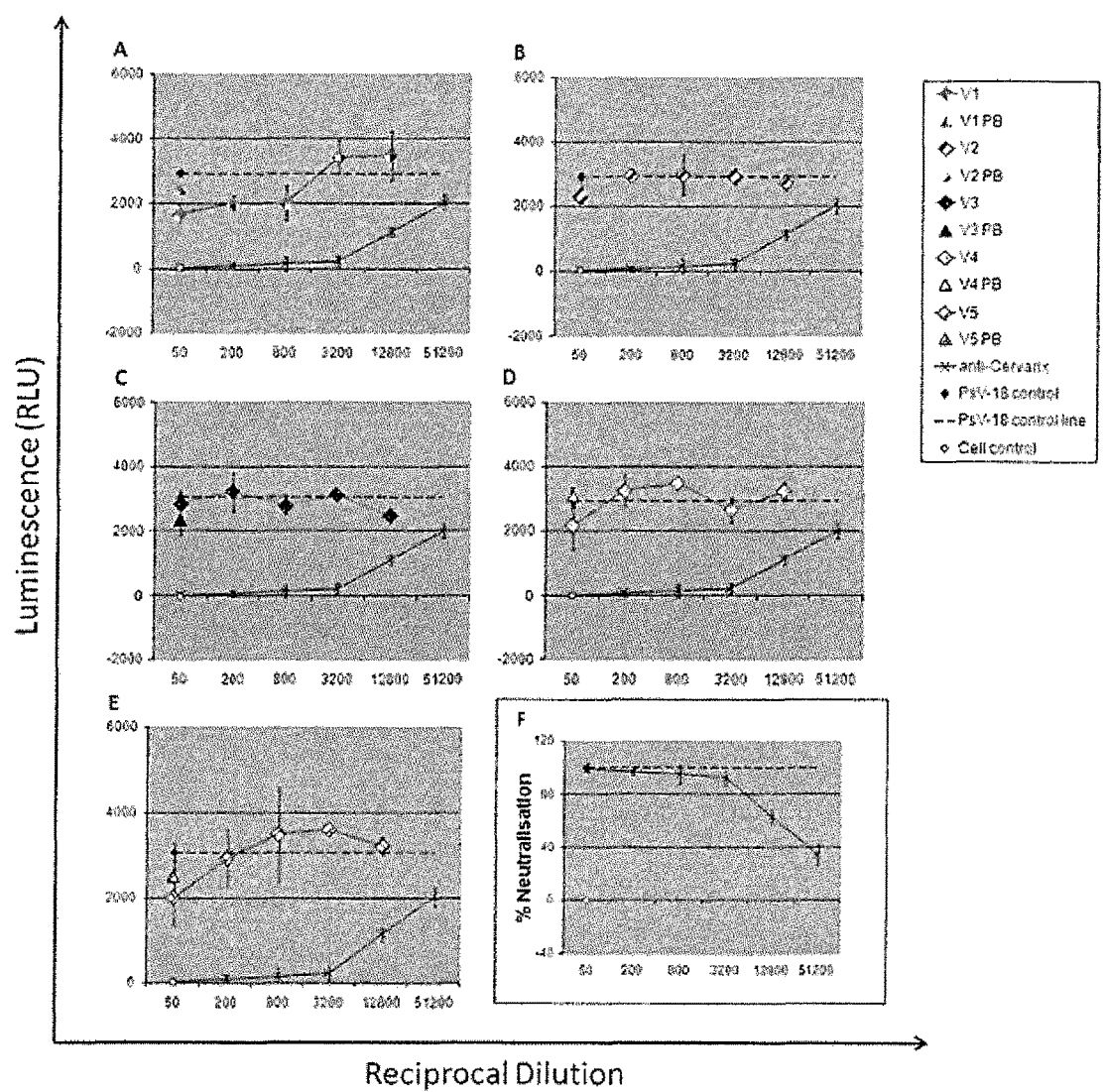

FIG. 12 shows a HPV-18 PsV neutralisation assay. A) V1=L1/L2(108-120), B) V2=L1/L2(56-81), C) V3=L1/L2(17-36), D) V4=HPV-16 L1, E) V5=NSs-infiltrated plant extract (−ve vaccine control). F) Rabbit anti-Cervarix sera=+ve neutralisation control.

Figure 13:
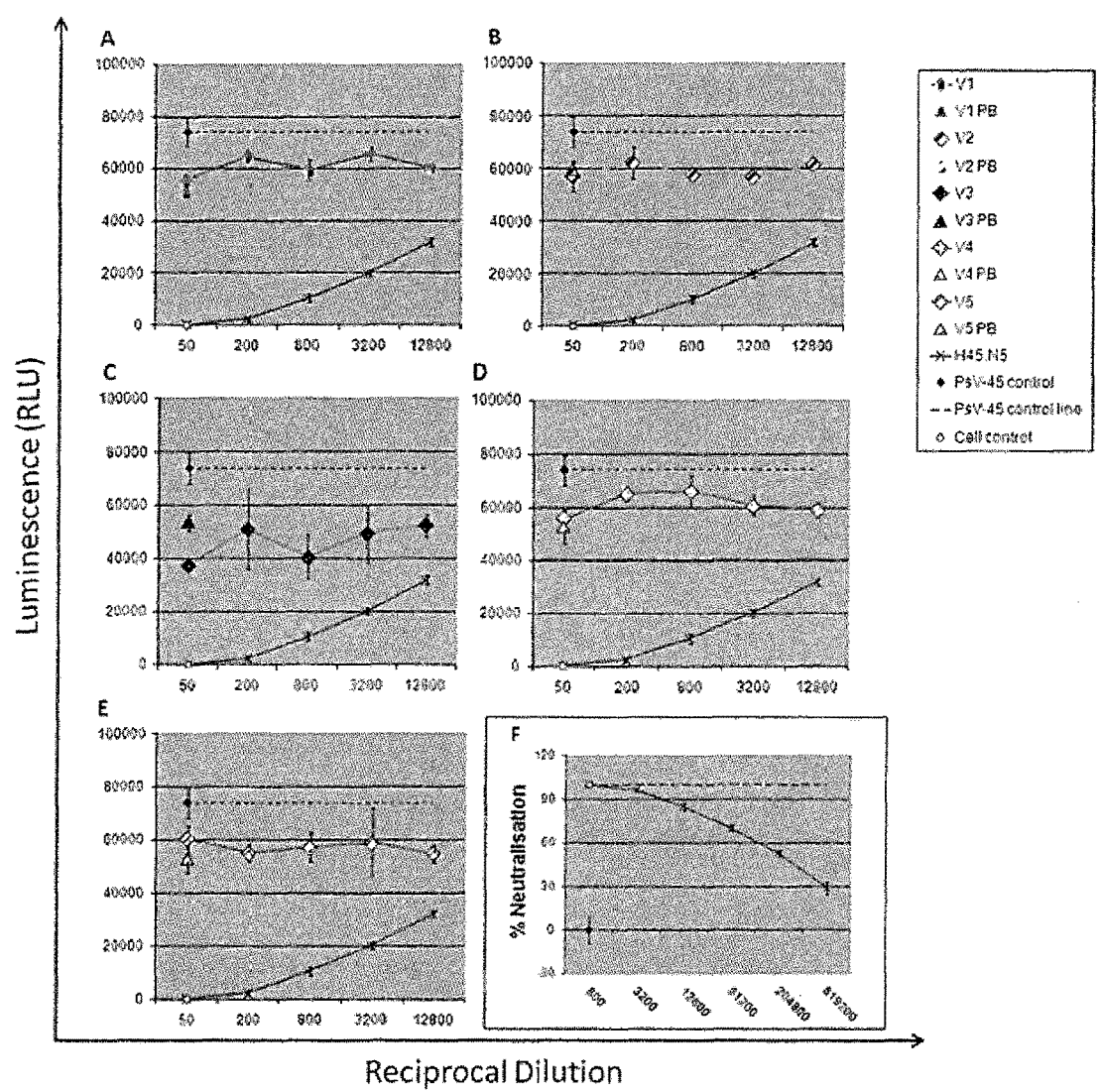

FIG. 13 shows a HPV-45 PsV neutralisation assay. A) V1=L1/L2(108-120), B) V2=L1/L2(56-81), C) V3=L1/L2(17-36), D) V4=HPV-16 L1, E) V5=NSs-infiltrated plant extract (−ve vaccine control). F) H45.N5=+ve neutralisation control.

Figure 14:
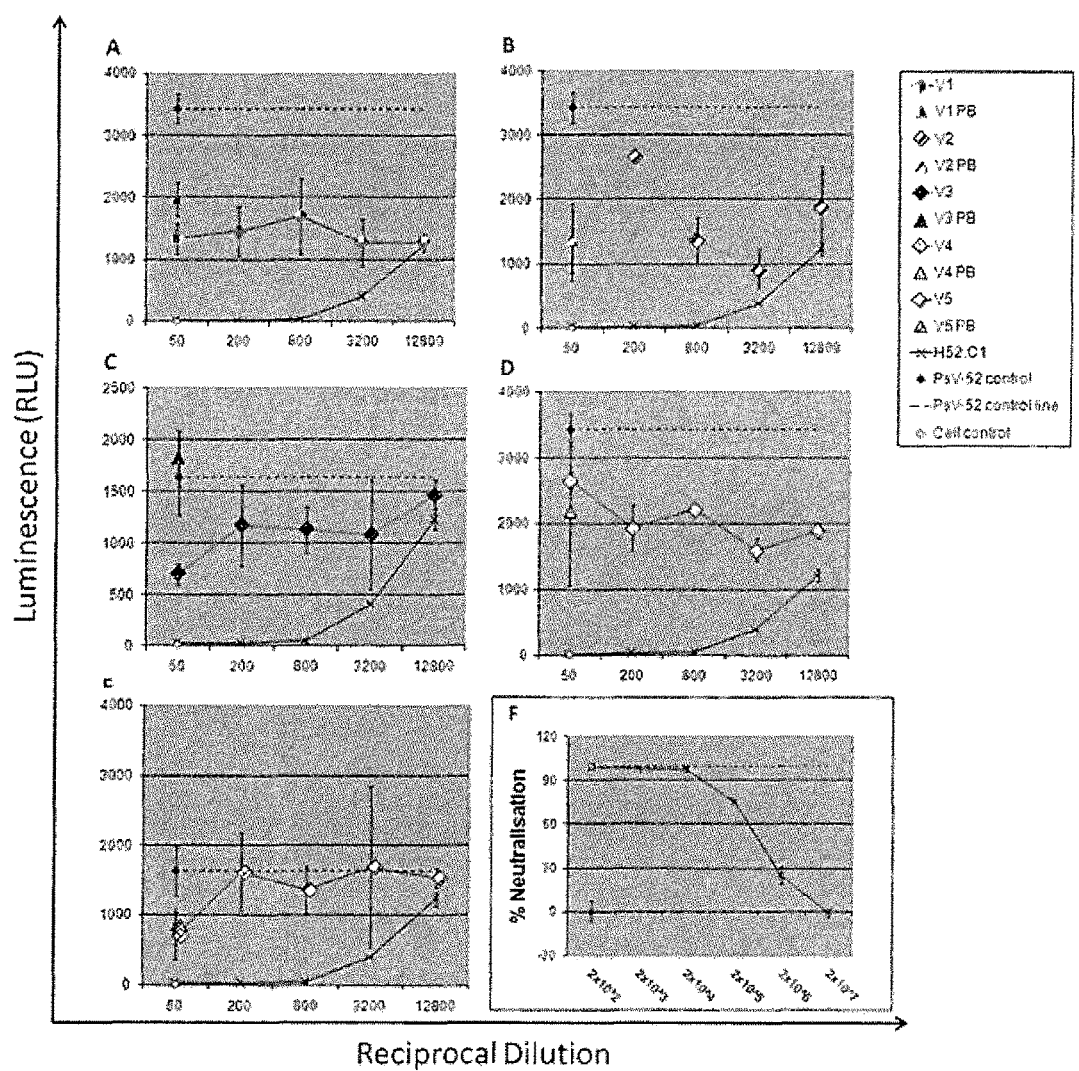

FIG. 14 shows a HPV-52 PsV neutralisation assay. A) V1=L1/L2(108-120), 8) V2=L1/L2(56-81), C) V3=L1/L2(17-36), D) V4=HPV-16 L1, E) V5=NSs-infiltrated plant extract (−ve vaccine control). F) H52.C1=+ve neutralisation control.

FIG. 15 shows the amino acid (SEQ ID NO: 1) of HPV-16 L1.

FIG. 16 shows the human-codon optimised nucleotide sequences (SEQ ID NO: 2) of HPV-16 L1.

FIG. 17 shows the amino acid sequence (SEQ ID NO: 3) of the L2 (108-120) epitope which was inserted into the HPV L1 sequence.

FIG. 18 shows the amino acid sequence (SEQ ID NO: 4) of the L2 (56-81) epitope which was inserted into the HPV L1 sequence.

FIG. 19 shows the amino acid sequence (SEQ ID NO: 5) of the L2 (17-36) epitope which was inserted into the HPV L1 sequence.

FIG. 20 shows the amino acid sequence (SEQ ID NO: 6) of the L2 BPV (1-88) epitope which was inserted into the HPV L1 sequence.

FIG. 21 shows the human-codon optimised DNA nucleotide sequence (SEQ ID NO: 7) of L2 (108-120) which was inserted into the HPV L1 sequence.

FIG. 22 shows the human-codon optimised DNA nucleotide sequence (SEQ ID NO: 8) of L2 (56-81) which was inserted into the HPV L1 sequence.

FIG. 23 shows the human-codon optimised DNA nucleotide sequence (SEQ ID NO: 9) of L2 (17-36) which was inserted into the HPV L1 sequence.

FIG. 24 shows the human-codon optimised DNA nucleotide sequence (SEQ ID NO: 10) of L2 BPV (1-88) which was inserted into the HPV L1 sequence.

FIG. 25 shows the amino acid sequence (SEQ ID NO: 22) of the HPV 16 L1/L2(108-120) chimaeric polypeptide.

FIG. 26 shows the amino acid sequence (SEQ ID NO: 23) of the HPV 16 L1/L2(56-81) chimaeric polypeptide.

FIG. 27 shows the amino acid sequence (SEQ ID NO: 24) of the HPV 16 L1/L2(17-36) chimaeric polypeptide.

FIG. 28 shows the amino acid sequence (SEQ ID NO: 25) of the HPV 16 L1/L2 BPV(1-88) chimaeric polypeptide.

FIG. 29 shows the human-codon optimised DNA nucleotide sequence (SEQ ID NO: 26) encoding the HPV 16 L1/L2(108-120) chimaeric polypeptide.

FIG. 30 shows the human-codon optimised DNA nucleotide sequence (SEQ ID NO: 27) encoding the HPV 16 L1/L2(56-81) chimaeric polypeptide.

FIG. 31 shows the human-codon optimised DNA nucleotide sequence (SEQ ID NO: 28) encoding the HPV 16 L1/L2(17-36) chimaeric polypeptide.

FIG. 32 shows the human-codon optimised DNA nucleotide sequence (SEQ ID NO: 29) encoding the HPV L1/L2 BPV(1-88) chimaeric polypeptide.

DETAILED DESCRIPTION OF THE INVENTION

The present invention will now be described more fully hereinafter with reference to the accompanying figures, in which some, but not all embodiments of the invention are shown.

The invention as described should not to be limited to the specific embodiments disclosed and modifications and other embodiments are intended to be included within the scope of the invention. Although specific terms are employed herein, they are used in a generic and descriptive sense only and not for purposes of limitation.

Terms used herein have their meaning recognised in the art unless otherwise indicated.

The current invention provides a chimaeric human papillomavirus (HPV) virus like particle (VLP) having a regular shape and a size of about 30 nm in diameter and a method of treatment and/or prophylaxis of HPV infection and/or cervical cancer by administration of the chimaeric HPV VLP of the invention. In particular, the regularly shaped and 30 nm diameter chimaeric HPV VLP comprises a HPV type 16 L1 protein into which a HPV L2 peptide of between about 13 amino acids and about 26 amino acids encoded by a human codon-optimised nucleotide sequence has been inserted at amino acid residue 414, thereby replacing the corresponding HPV L1 amino acids.

The L1 major capsid protein spontaneously self-assembles into virus-like particles (VLPs), which form the basis of the current prophylactic HPV vaccines (Schiller et al., 2008). Recombinant VLPs have been expressed in several diverse host systems including mammalian, insect, yeast, bacteria and plants.

The HPV-16 L1 C-terminal helix 4 (h4) plays a role in VLP assembly and is located between residues 414-426 (Varsani of al., 2003a). The removal of these motifs results in capsomere formation and prevents further self-assembly into VLPs (Bishop of al., 2007). Furthermore, there are disulphide bonds between highly conserved cysteine residues 175 and 428, and mutations of these cysteines results in the formation of capsomeres rather than VLPs (L1 of al., 1998; McCarthy et al., 1998; Sapp et al., 1998; Fligge et al., 2001; Varsani et al., 2006b). However, in this study, it was shown that insertion of a HPV L2 peptide of between about 13 amino acids and about 26 amino acids encoded by a human codon-optimised nucleotide sequence, when inserted at amino acid residue 414, thereby replacing the corresponding HPV L1 amino acids, was able to successfully assemble into small, regularly shaped chimaeric VLPs of about 30 nm in diameter.

Commercial HPV vaccines (currently expressed in yeast or insect cells) are expensive (Schiller et al., 2008), partially as a result of costly production and purification protocols. In addition, complicated purification methods and extensive pre-treatment can affect the stability and recovery of assembled L1 protein and denatured L1 does not induce neutralising antibodies. As a result, the production of vaccine antigens using low-cost expression systems and simple production and purification processes remain high priorities in any commercial protein production system.

The invention will be described by way of the following examples which are not to be construed as limiting in any way the scope of the invention.

EXAMPLES

Example 1

Transient Plant Expression of L1 Chimaeras

Methods and Materials
Plant Expression Vectors

Three binary *Agrobacterium* plant expression vectors were used to optimize HPV chimaera expression: pTRAc and pTRAkc-rbcs1-cTP (provided by Prof. Rainer Fischer; Fraunhofer Institute for Molecular Biology and Applied Ecology, Germany) and the Bean yellow dwarf geminivirus (BeYDV) vector pRIC3 (created by Richard Halley-Stott). Two are non-replicative vectors which target the expressed protein to either the cytoplasm (pTRAc) or chloroplast (pTRAkc-rbcs1-cTP) (Maclean et al., 2007), and the third is a self-replicating cytoplasm-targeting vector (pRIC3). The pRIC3 vector is a third-generation pRIC vector (Regnard et al., 2010), which has been reduced in size and has shown similar amplification of transgene expression in planta.

Figure 1:
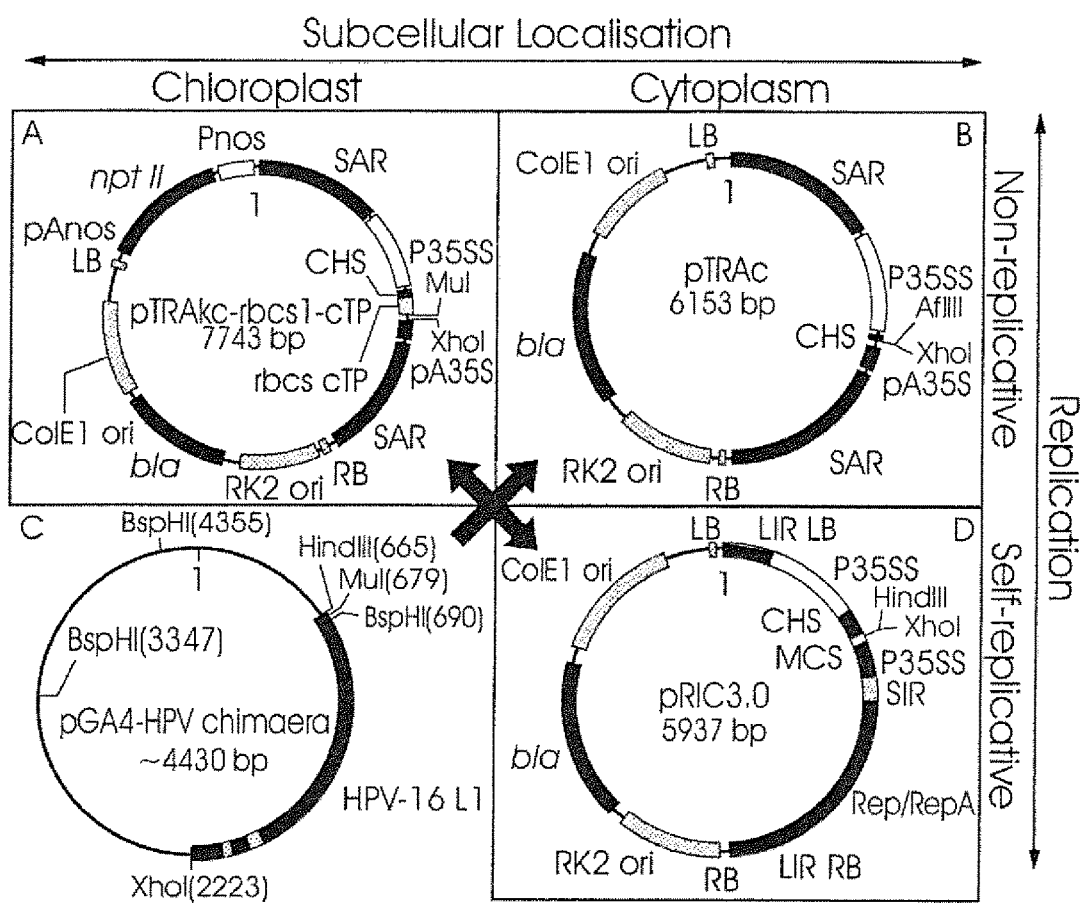
FIG. 1 shows plasmids used to create the HPV chimaera plant expression constructs. C) HPV chimaera genes from pGA4 constructs were directionally subcloned into the *Agrobacterium* plant expression vectors: A) pTRAkc-rbcs1-cTP, B) pTRAc and D) pRIC3. The vector elements necessary for plant expression are shown in the figure. P3555: CaMV 35S promoter containing duplicated transcriptional enhancer, CHS: chalcone synthase 5′ untranslated region, pA35S: CaMV 35S polyadenylation signal for foreign gene expression, ColE1ori: *E. coli* origin of replication, RK2ori: *Agrobacterium* origin of replication, b/a: ampicillin/carbenicillin-resistance gene, and LB/RB: left and right borders for T-DNA integration. The pTRAc vector contains SAR: tobacco Rb7 scaffold attachment regions flanking the expression cassette. In addition, the pTRAkc-rbcs1-cTP vector contains npt II: the kanamycin-resistant gene, Pnos/pAnos: promoter/polyadenylation signal of the nopaline synthase gene and rbcs1-cTP: *Solanum tuberosum* chloroplast-transit peptide sequence of the Rubisco small-subunit gene rbcS1. The pRIC3 vector contains LIR: BeYDV long intergenic region, SIR: BeYDV short intergenic region, and Rep/RepA: BeYDV rep gene.

The vectors contain a number of elements necessary for protein expression in plants (FIG. 1). The pTRAkc-rbcs1-cTP vector (FIG. 1A) is a derivative of pTRAc (FIG. 1B), and contains the chloroplast-transit peptide sequence of the potato rbcS1 gene. The pRIC3 (FIG. 1D) contains the BeYDV replication-associated proteins necessary for self-replication (Regnard et al., 2010).

Synthesis of the L1 Chimaeras

The four HPV-16 L1/L2 chimaeras used in this study are described in Table 1. The chimaeras consist of a South African HPV-16 L1 isolate gene sequence (SALT: GenBank accession no. AY177679) with an L2 epitope located in the h4 helix at aa 414 (denoted the "F-position"). These chimaeric genes were designed by Dr Inga Hitzeroth (Plant Vaccine Group, UCT), human codon-optimised and synthesized in silica by GENEART AG (Regensburg, Germany) using high throughput gene assembly. Synthesized L2 epitope sequences replaced the L1 sequence in the F-position and were not simply inserted into the L1 protein.

TABLE 1

Summary of the HPV-16 L1 chimaeric constructs

| Construct | Inserted epitope | L1 position of epitope | Sequence substitution (aa) |
|---|---|---|---|
| L1/L2 (108-120) | HPV-16 L2 aa 108-120 | F-position aa 414-426 | 13 |
| L1/L2 (56-81) | HPV-16 L2 aa 56-81 | aa 414-439 | 26 |

TABLE 1-continued

Summary of the HPV-16 L1 chimaeric constructs

| Construct | Inserted epitope | L1 position of epitope | Sequence substitution (aa) |
|---|---|---|---|
| L1/L2 (17-36) | HPV-16 L2 aa 17-36 | aa 414-433 | 20 |
| L1/L2 BPV (1-88) | BPV-1 L2 aa 1-88 | aa 414-505 | 88 |

Subcloning of the L1 Chimaera Genes

The HPV-16 L1/L2, chimaera sequences were excised from pGA4 vectors using 3' XhoI and either 5' BspHI, MluI or HindIII restriction enzyme (RE) sites that flank the chimaeric genes (FIG. 1C). The HPV genes were directionally subcloned into the plant expression vectors, using MluI and XhoI for pTRAc (FIG. 1B), MluI and XhoI for pTRAkc-rbcs1-cTP (FIG. 1A), and XhoI for pRIC3 (FIG. 1D). DH5-α chemically competent E. coli cells (E.cloni™, Lucigen) were transformed with the chimaera plasmid constructs and recombinants were selected using ampicillin resistance (100 µg/ml). The pTRAc HPV-16 L1/L2 chimaera constructs L1/L2(108-120), L1/L2(56-81) and L1/L2(17-36) were provided by Mark Whitehead (Plant Vaccine Group, UCT). The plasmid constructs used in this study are summarized in Table 2.

TABLE 2

Agrobacterium expression constructs used in this study

| Plant Expression Vector | Chimaeras tested | Plasmid replication | Subcellular localisation | Source |
|---|---|---|---|---|
| pTRAc | L1/L2 | Non-replicative | Cytoplasm | M. Whitehead |
| pTRAkc-rbcs1-cTP | L1/L2 | Non-replicative | Chloroplast | This study |
| pRIC3 | L1/L2 | Self-replicative | Cytoplasm | This study |

Identification of Recombinant L1 Chimaeras

L1 chimaera recombinant clones were screened by colony PCR, using pTRAc vector-specific primers and chimaera-specific primers binding to different L2 epitopes (Table 3). PCR was performed using GoTaq Flexi DNA Polymerase kit (Promega) as per the manufacturer's instructions using 1 µM of each primer in a final MgCl$_2$ concentration of 3 mM.

TABLE 3

Primers used in PCR and sequencing of the HPV chimaeras

| Primer target | Chimaera detected | Primer name | Primer sequence | PCR product (kb) |
|---|---|---|---|---|
| pTRAc vector | All chimaeas | pTRAc Fwd | 5'-CATTTCATTTGG AGAGGACACG-3' (SEQ ID NO: 11) | ~1.7 |
| | | pTRAc Rvs | 5'-GAACTACTCACA CATTATTCTGG-3' (SEQ ID NO: 12) | |
| L1/L2 chimaeras | All chimaeras | ModNew Fwd | 5'-CGACGACCTGTA CATCAAGG-3' (SEQ ID NO: 13) | — |
| | L1/L2 (108-120) | VEET Rvs | 5'-GATGAAGCTGGT CTCCTCC-3' (SEQ ID NO: 14) | 0.41 |
| L1/L2 (56-81) | | SAF2 Rvs | 5'-GGATGTAGCCG GTCCTGC-3' (SEQ ID NO: 15) | 0.44 |
| L1/L2 (17-36) | | QLYK Rvs | 5'-ACCTTGGGGAT GATGICAGG-3' (SEQ ID NO: 16) | 0.44 |
| L1/L2 BPV(1-88) | | SALIBPV Rvs | 5'-TATCTAGGGCTT CCTCCAGC-3' (SEQ ID NO: 17) | 0.56 |

Colony PCR Using Vector-specific Primers

The pTRAc vector-specific primers (designed by Mark Whitehead) bind upstream and downstream of the multiple cloning site (MCS) to detect the gene insertions. The PCR profile consisted of an initial denaturation step at 95° C. for 3 min, followed by 25 cycles at 95° C. for 30 s, 59° C. for 30 s and 72° C. for 3 min, and a final elongation step at 72° C. for 3 min. PCR products were separated on a 0.8% TBE agarose gel and detected using ethidium bromide.

Colony PCR Using Epitope-specific Primers

HPV L2 epitope-specific primers (designed by Marieta Burger) were used to verify the correct chimaera insert in recombinant pTRAkc-rbcs1-cTP and pRIC3 clones. The PCR profile consisted of an initial denaturation step at 95° C. for 2 min, followed by 25 cycles at 95° C. for 30 s, 55° C. (L1/L2 chimaeras) for 20 s and 72° C. for 30 s, and a final elongation step at 72° C. for 3 min. PCR products were separated on a 1.2% TBE agarose gel and detected using ethidium bromide.

Restriction Enzyme Digestion

Recombinants were verified by restriction enzyme digestion using RE sites which flank the 1.5 kb chimaera gene insert (EcoRI/XhoI for pTRAkc-rbcs1-cTP clones, or HindIII/XhoI for pRIC3 clones), Recombinant DNA (~500 µg) was digested for 1-2 hrs at 37° C., using 1 U enzyme per reaction as per manufacturer's instructions (Roche/Fermentas). Digested DNA was separated on a 0.8% TBE agarose gel and stained with ethidium bromide.

Sequencing of L1 Chimaeras

The HPV chimaera gene insert in pTRAkc-rbcs1-cTP recombinants were sequenced using the pTRAc vector-specific primers. Sequences were aligned with the HPV chimaera sequences using DNAMAN multiple alignment software.

Agrobacterium Transformation

Agrobacterium tumefaciens GV3101::pMP90RK cells were made electrocompetent using the method described by Shen and Forde (1989). Transformation of Agrobacterium was performed as described by Maclean et al. (2007) and recombinant clones were screened by antibiotic selection (50 µg/ml Carbenicillin, 50 µg/ml Rifampicin and 30 µg/ml Kanamycin). Successful transformation was confirmed by colony PCR and restriction enzyme digestion (as described above).

Agroinfiltration of N. benthamiana

A. tumefaciens recombinant chimaera cultures, as well as A. tumefaciens LBA4404 cultures containing the pBIN-NSs plasmid encoding the tomato spotted wilt virus (TSWV) NSs silencing suppressor (Takeda et al., 2002), were prepared for infiltration as described by Maclean et al. (2007).

The *Agrobacterium* cells were diluted in infiltration media (10 mM $MgCl_2$, 10 mM MES, 3% sucrose and 150 µM acetosyringone in water, pH 5.6) to give a final $OD_{800}$ of 0.25 for individual *Agrobacterium* chimaera strains and a combined $OD_{600}$ of 0.5 for the constructs co-infiltrated with *A. tumefaciens* LBA4404 (pBIN-NSs). The strains were incubated at 22° C. for 2 hrs to allow for expression of the vir genes prior to infiltration.

Six-week old *N. benthamiana* leaves were agroinfiltrated by injecting the bacterial suspension into the abaxial air spaces from the ventral side of the leaf (Maclean et al., 2007). The plants were grown under conditions of 16 hr light, 8 hr dark at 22° C. for the desired time period. Chimaera expression time trials were conducted 1-9 days post-infiltration (dpi), and chimaeras were either co-expressed with or without the NSs silencing suppressor. Separate plants were used for each chimaera, and separate leaves on the same plant were infiltrated with either pTRAc, pTRAkc-rbcs1-cTP or pRIC3 chimaera constructs for the comparative vector expression.

Protein Extraction from Plants

Leaf discs, cut using the cap of an eppendorf tube, were harvested from agroinfiltrated leaves (~10 mg per disc, 3 discs per construct) and ground in liquid nitrogen. Leaf material was resuspended in 250 µl per disc of 1.5M NaCl high salt PBS (HS PBS) extraction buffer containing protease inhibitor (EDTA-fee Complete Protease Inhibitor; Roche). The crude plant extract was clarified twice by centrifugation at 13,000 rpm for 5 min and the supernatant was stored at −20° C.

Western Blot Detection of Plant-expressed L1 Chimaeras

The plant extracts were incubated at 95° C. for 5 min in loading buffer (Sambrook et al., 1989), separated by a 10% SDS-PAGE gel and transferred onto a nitrocellulose membrane by semi-dry electroblotting. The membrane was blocked in blocking buffer for 30 min at room temperature (5% skim milk, 0.1% Tween-20 in 1×PBS, pH 7.6) and incubated overnight at 4° C. in anti-L1 primary antibody, diluted in blocking buffer. HPV-16 L1 protein was detected with either mouse monoclonal (MAb) CamVir1 (1:10000; Abcam, UK), which binds to the L1 linear epitope GFGAMDF located at aa 230-236 (McLean et al, 1990), or H16.J4 (1:2500) which binds a linear epitope located at aa 261-280 within the FG loop of the L1 protein (Christensen et al., 1996). Both binding sites are not destroyed by the L2 epitope insertions.

Membranes were washed with blocking buffer for 4×15 min, and incubated in secondary goat-anti-mouse-alkaline phosphatase conjugate (1:10000; Sigma) diluted in blocking buffer for 2 hrs at room temperature. Membranes were finally washed with wash buffer (0.1% Tween-20 in 1×PBS, pH 7.6) for 4×15 min and developed with Nitro blue tetrazolium chloride/5-broma-4-chloro-3-indoyl phosphate substrate (NBT/BCIP substrate; Roche). Chimaera expression was compared by measuring the density of the bands detected on anti-L1 western blots using GeneTools (SYN-GENE).

Chimaera Quantification by Capture ELISA

The L1 chimaeras extracted from *N. benthamiana* were quantified by capture ELISA using a modified polyvinyl alcohol (PVA)-blocking ELISA method (Studentsov et al., 2002). Briefly, a 96-well Maxisorp microtitre plate was coated with 1:2000 mouse anti HPV-16 L1 MAb (either CamVir1 or H16.J4) overnight at 4° C. and blocked with PVA. Plant extract was added to the wells and incubated for 1 hr at 37° C. This was followed by a washing step and the addition of rabbit anti-HPV-16 polyclonal serum (1:1000).

The plate was incubated overnight at 4° C. and HPV-16 L1 protein was detected with swine anti-rabbit horseradish peroxidase (HRP) conjugate (1:5000; DAKO) and 1.2-phenylenediamine dihydrochloride substrate (OPD; DAKO; Denmark).

The commercial HPV vaccine Cervarix was used as a positive ELISA control and as a HPV-16 L1 VLP standard. Each sample was analysed in triplicate and quantified using the Cervarix standard curve. The amount of chimaera protein present in each sample (mg) was expressed as chimaera per kilogram of plant tissue (mg/kg).

Total soluble protein (TSP) for each crude leaf extract was determined using the Lowry protein assay (Biorad DC Protein Assay; Microplate Assay Protocol) as per the manufacturer's instructions using a Bovine plasma gamma globin IgG protein standard (Bio-Rad). The relative chimaera yield was calculated where the ELISA-quantified chimaera protein (mg) was expressed as a percentage of TSP, in order to account for differences in leaf tissue mass and protein extraction efficiency.

Statistical Analysis of Chimaera Expression Yields

Statistical differences in chimaera expression using the different plant expression vectors were determined using ANOVA and the Fischer LSD Post Hoc test. Differences were reported at statistically significant at $p<0.01$.

Chimaera Assembly

Assembly of the HPV proteins into higher-order immunogenic structures was assessed using a H16.J4 and H16.V5 capture ELISA as described above. The H16.J4 MAb binds to a L1 linear epitope comprising of aa 261-280 (Christensen et al., 1996) and thus gives the total HPV protein present in the plant extract. H16.V5 binds to a conformational L1 epitope (Christensen et al., 1996, 2001) containing essential aa 260-290 and specifically binding L1 residues Phe-50, Ala-266, and Ser-282 (White et al., 1999), thus it was used for the detection of assembled HPV protein. In order to compare the assembly of chimaeras expressed using different vectors, the amount of assembled HPV protein was expressed as a percentage of the total HPV protein.

Results

Verification of 1.1 Chimaera Clones

The L1 chimaeras (Table 1) were successfully cloned into the pTRAkc-rbcs1-cTP and pRIC3 plant expression vectors and transformed into *E. coli* and *Agrobacterium* GV3101.

The pTRAkc-rbcs1-cTP recombinant clones were screened by colony PCR using pTRAc-specific primers binding upstream and downstream of the MCS, or chimaera-specific primers binding to different L2 epitopes. All chimaeras produced fragments of the expected size as predicted in Table 3.

Clones were further verified by restriction enzyme (RE) digestion using EcoRI and XhoI RE sites which flank the chimaera gene insert. As expected, all chimaeras contained a 1.5 kb gene insert, Clones were sequenced and individual chimaeras were confirmed using DNAMAN multiple sequence alignment software.

The pRIC3 recombinant clones were similarly verified by colony PCR using the chimaera epitope-specific primers and HindIII/XhoI restriction enzyme digestion. All chimaeras produced the 0.2-0.6 kb chimaera-specific PCR bands described in Table 3 and the 1.5 kb gene fragment in the RE digests. Thus all the HPV chimaeras were successfully subcloned into the pTRAkc-rbcs1-cTP and pRIC3 plant expression vectors.

Optimisation of L1 Chimaera Expression in *N. benthamiana* Co-expression with the NSs Silencing Suppressor Chloroplast-targeted HPV-16 L1/L2 expression in *N. bethamiana* was examined in a 1-9 day post-infiltration (dpi) time trial. Chimaeras were expressed either with (+) or without (−) the NSs silencing suppressor protein to examine its effects on chimaera expression. Expression was analysed by western blotting using the anti-L1 MAb CamVir1. All the L1/L2 chimaeras were detected, with the predicted ~56 kDa L1 band (FIG. 2), although L1/L2 (108-120) runs higher than the other chimaeras.

All chimaeras showed a prolonged increase in expression when co-infiltrated with the silencing suppressor protein NSs (FIG. 2 A-D), suggesting it was effective in preventing post-translational gene silencing and enhancing protein accumulation in plants. ELISA detection using the linear-epitope specific MAb H16.J4 confirmed the results, with up to a 16-fold increase in L1/L2 yields (data not shown). Chimaera expression without NSs was detected 1-3 dpi and peaks 3-5 dpi, while chimaeras co-expressed with NSs was detected at 3 dpi and expression peaked at 5-7 dpi. There was a small decrease in expression between 5-9 dpi, suggesting there is a slow decline in expression levels (ELISA results, data not shown). As a result, all chimaeras were co-expressed with NSs in further experiments.

Several high molecular bands were detected for the L1/L2 (17-36) chimaera, suggesting the chloroplast signal sequence (cTP) may not have been cleaved or the chimaera may have been glycosylated. However, L1/L2 (17-36) analysed on subsequent western blots did not display these high molecular weight bands, suggesting the protein was partially denatured in FIG. 2C.

The L1/L2 chimaera containing the BPV L2 aa 1-88 epitope had low expression levels in comparison to the chimaeras containing HPV-16 L2 epitopes. The bands on the L1/L2 BPV (1-88) western blots were only visible after 16 hours of development (FIG. 2D), in comparison to the 15 min development time required for the other chimaeras (FIG. 2A-C). ELISA quantification estimated L1/L2 BPV (1-88) achieved maximum yields of 40 mg/kg plant tissue, while high expression yields of 1000-4600 mg/kg were estimated for the other L1/L2 chimaeras (data not shown). In addition, the L1/L2 BPV(1-88) plant extract contained a characteristic ~45 kDa band (FIG. 2D) associated with L1 degradation, suggesting L1/L2 BPV(1-88) is unstable in this expression system. These results were confirmed by several L1/L2 BPV(1-88) western blots from different time trials.

Effect of Chloroplast Targeting on L1/L2 Chimaera Yield

Targeting of HPV proteins to the chloroplast can significantly improve plant expression yields (Maclean et al., 2007). To determine the importance of chloroplast-targeting, the pTRAc (cytoplasmic-targeting) and the pTRAkc-rbcs1-cTP (chloroplast-targeting) L1/L2 chimaera constructs were co-infiltrated with pBIN-NSs in *N. benthamiana* in a 3-9 dpi time trial. The L1/L2 BPV(1-88) chimaera was not included in this study, as it shows very low expression in *N. bethamiana* when compared to the other L1/L2 chimaeras.

Western blots and ELISA data consistently demonstrated low expression for the cytoplasm-targeted L1/L2 chimaeras, with maximum expression of chimaeras 3 dpi and yields of 20-45 mg/kg plant tissue (data not shown). Expression of cytoplasm-targeted L1/L2(108-120), L1/L2(56-81) and L1/L2(17-36) was weakly detected in comparison to the chloroplast-targeted L1/L2(108-120) chimaera diluted 3× prior to loading and included as a positive control. Comparison of chimaera yields indicates that L1/L2 chimaera expression was increased 40-80 fold when targeted to the chloroplast. Taking these results into consideration, further chimaera expression studies were done using the pTRAkc-rbcs1-cTP vector.

Optimisation Using the Self-replicative pRIC3 Plant Expression Vector

In an attempt to improve chimaera yields, particularly for the low-expressing L1/L2 BPV(1-88), the plant expression vector pRIC3 (self-replicative, cytoplasm-targeting vector) was compared to pTRAkc-rbcs1-cTP (non-replicative chloroplast-targeting vector) in a 3-9 dpi time trial in the presence of NSs.

Maximum chimaera yields for both vectors were obtained 3-5 dpi. The three L1/L2 chimaeras containing the HPV-16 L2 epitopes aa 108-120, 56-81 and 17-36 were better expressed using the chloroplast-targeting pTRAkc-rbcs-cTP vector compared to the self-replicative pRIC3 vector. L1/L2 BPV(1-88) was not highly expressed for either vector and degradation was visible for both constructs.

ELISA quantification shows the self-replicative pRIC3 vector did not improve expression yields for the majority of the chimaeras. Yields were up to 3-fold higher using the pTRAkc-rbcs1-cTP vector, suggesting that chloroplast-targeting is more effective in the high-expression of chimaeras than the pRIC3 vector, which ultimately targets the expressed protein to the cytoplasm. The L1/L2 BPV(1-88) expression levels were similar to the NSs negative control, suggesting plants are not a viable system for the production of L1/L2 BPV(1-88) and the expression of L1/L2 BPV(1-88) was not pursued further.

The results from the expression optimization using the pTRAkc-rbcs1-cTP and pRIC3 vectors are summarised in Table 4. The L1/L2(108-120), L1/L2(56-81) and L1/L2(17-36) were highly-expressed. The parameters shown to maximise expression in the preliminary time trials are: co-expression with NSs, extraction 5 dpi and use of the pTRAkc-rbcs-cTP vector to target the expressed L1/L2 protein to the chloroplast.

TABLE 4

Summary of L1 chimaera expression and optimization

| | Maximum chimaera expression | | | | |
|---|---|---|---|---|---|
| Chimaera | Extraction (dpi) | Vector | Yield (mg/kg) | Yield (% TSP) | Fold increase (pTRAkc-rbcs1-cTP vs. pRIC3) |
| L1/L2(108-120) | 5 | pTRAkc-rbcs1-cTP | 600 | 3.7 | 1.8 |
| L1/L2(56-81) | 5 | pTRAkc-rbcs1-cTP | 280 | 1.7 | 2.4 |
| L1/L2(17-36) | 5 | pTRAkc-rbcs1-cTP | 440 | 2.9 | 1.8 |
| L1/L2 BPV(1-88) | 5 | pTRAkc-rbcs1-cTP | — | — | — |

Comparative Vector Expression of L1/L2 Chimaeras

Three high-expressing L1/L2 chimaeras were chosen as vaccine antigens for the mouse immunogenicity studies: L1/L2(108-120), L1/L2(56-81) and L1/L2(17-36). A final expression study including three biological repeats was performed to confirm the L1/L2 results and obtain statistically valid data. All three vectors (pTRAc, pTRAkc-rbcs1-cTP and pRIC3) were directly compared for expression of each of the L1/L2 vaccine antigens, HPV-16 L1 was included as a positive control (pTRAc and pTRAkc-rbcs1-cTP constructs were available) and NSs-infiltrated plants served as the negative control. Chimaeras were co-expressed with NSs and extracted 5 dpi.

Effect of Expression on Plants

Examination of the infiltrated leaves prior to extraction 5 dpi suggested that the self-replicative pRIC3 vector had adverse effects on the health of the plant. Leaves infiltrated with pRIC3 were yellow/brown in colour and necrosis of the leaf tissue was visible in the infiltrated areas. This was observed to a lesser degree in the pTRAc leaves, which also targeted chimaeras to the plant cytoplasm. The pTRAkc-rbcs-cTP leaves appeared to be the healthiest, resembling the leaves of the NSs-infiltrated negative control and the uninfiltrated leaves, suggesting accumulation of the chimaras in the chloroplast has less of an impact on plant health (results not shown). Infiltration appears to have no observable effect on plant health, as the NSs-infiltrated leaf looked similar to the uninfiltrated leaf (excluding the syringe injection markings). These results were consistently observed for all the time trials.

Western Blot Detection of the HPV Proteins

HPV protein was detected by anti-L1 western blotting (FIG. 3a). The NSs-infiltrated plant extract (negative control) was not detected and plant-derived HPV-16 L1 (positive control) was detected using the chloroplast-targeting vector. Expression using the different vectors was directly compared with pTRAkc-rbcs1-cTP consistently giving the highest expression yields, followed by pRIC3, and then pTRAc.

ELISA Quantification of the HPV Proteins

Capture ELISA was used to quantify the HPV chimaeras using CamVir1. The L1/L2 chimaera and HPV-16 L1 yields are shown in FIG. 3b. Statistical differences in chimaera expression using the 3 plant expression vectors were determined using ANOVA and the Fischer LSD Post Hoc test. Differences were reported at statistically significant at $p<0.01$.

Chloroplast-targeted expression of the L1/L2 chimaeras and HPV-16 L1 using pTRAkc-rbcs1-cTP gave significantly higher yields than the NSs-infiltrated negative control ($p=0.000$-$0.002$), and the cytoplasm-targeting pTRAc vector ($p=0.000$-$0.004$). In addition, pTRAkc-rbcs1-cTP significantly improved L1/L2(56-81) expression compared to pRIC3=$0.006$). The pRIC3 vector did not statistically improve expression of any of the chimaeras compared to pTRAc.

In comparison to the optimization experiments (FIG. 2, Table 4), the comparative time trial demonstrated similar trends in chimaera expression. The chloroplast-targeted L1/L2 chimaeras gave the highest yields (1040-1310 mg/kg; 2-3% TSP), improving chimaera expression by up to 28-fold in comparison to the cytoplasm-targeting vector pTRAc (50-260 mg/kg; <1% TSP) and up to 7-fold in comparison to the self-replicative vector pRIC3 (190-660 mg/kg; <1% TSP).

Cytoplasm-targeted chimaera yields were improved up to 4-fold using the self-replicative vector pRIC3 in comparison to the non-replicative pTRAc vector. This suggests self-replication of the vector improves chimaera expression, although targeting to the chloroplast appears to be a superior strategy to increase chimaera expression in plants.

Although chloroplast-targeted HPV-16 L1 demonstrated higher average yields (1710 mg/kg, 4% TSP), the differences between the L1/L2 chimaeras and L1 were not statistically significant, indicating the L2 epitope substitutions do not appear to affect the expression and accumulation of recombinant protein in chloroplasts. However, western blotting (3a) and ELISA expression data (FIG. 3b) consistently revealed higher levels of cytoplasm-localised L1/L2(108-120) and L1/L2(17-36) than L1/L2(56-81), suggesting L1/L2(108-120) and L1/L2(17-36) chimaeras with shorter L2 sequence replacements (13 and 20 aa respectively) may be better expressed and have a greater stability than L1/L2 (56-81) with a 26 aa sequence replacement.

Assembly of the HPV Proteins

Chimaera assembly into higher-order structures such as capsomeres or VLPs was assessed using H16.J4 (linear epitope-specific MAb) and H16.V5 (conformational epitope-specific MAb) capture ELISA. The amount of V5-detected conformational HPV protein was expressed as a percentage of the J4-detected total HPV protein for each of the vector constructs (FIG. 4).

A low percentage of the expressed chimaeras assembled into H16.V5-detected higher-order structures. The NSs plant extract, used as a negative control, did not bind H16.J4 or H16.V5 MAb (data not shown). The low-expressing pTRAc chimaeras appear to have the highest proportion of assembled protein (11-18%), followed by the high-expressing pTRAkc-rbcs1-cTP chimaeras (5-9%). The pRIC3 chimaeras did not contain a high percentage of assembled protein (<2%). Although the pTRAkc-rbcs1-cTP chimaeras did not contain the highest percentage of assembled protein, higher expression yields results in up to 40× and 4× more assembled protein than pTRAc and pRIC3 respectively. This provides further evidence that pTRAkc-rbcs1-cTP is the best vector to use for the production of immunogenic L1/L2 chimaeras.

Discussion

Optimisation of L1 Chimaera Transient Expression in Plants

Figure 2:
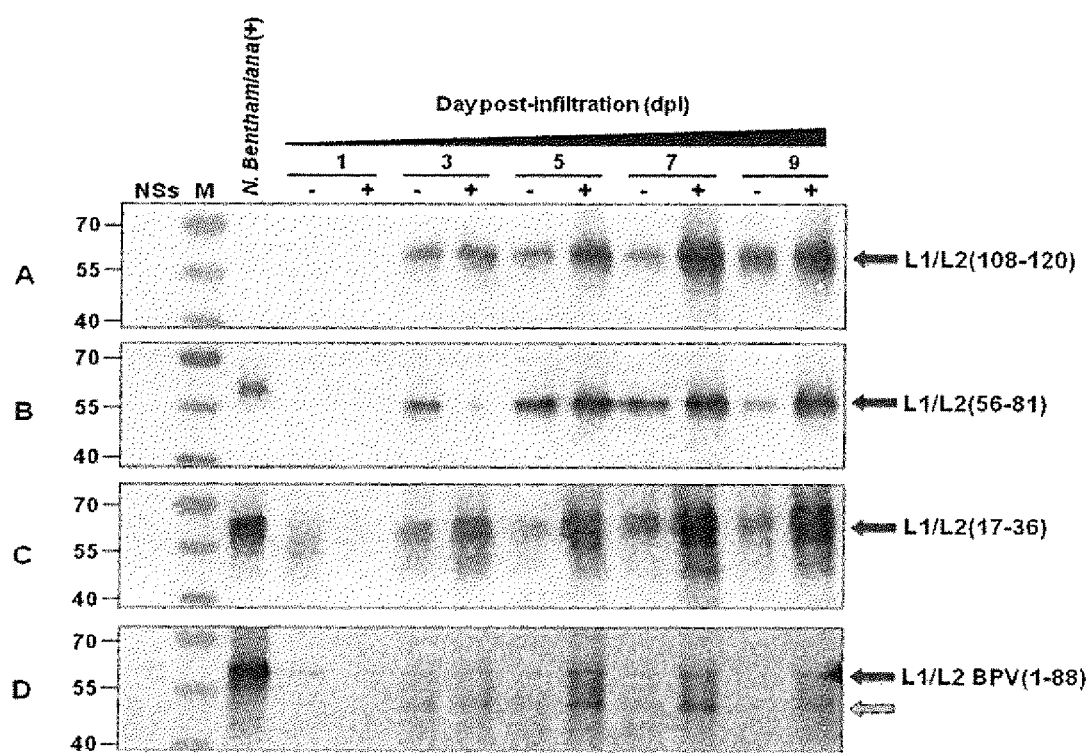
FIG. 2 shows chloroplast-targeted L1/L2 chimaera expression time trial 1-9 days post-infiltration (dpi) in *N. benthamiana*, either with (+) or without (−) the NSs silencing suppressor. The L1/L2 chimaeras A) L1/L2(108-120), B) L1/L2(56-81), C) L1/L2(17-36) and D) L1/L2 BPV (1-88) in crude leaf extracts were detected by CamVir1 western blot analysis. M=protein marker with the size in kDa indicated on the left. NSs negative control=pBIN-NSs infiltrated crude plant extract (5 dpi). Positive controls: *N. benthamiana*

All of the L1 chimaeras were successfully expressed in plants using an *Agrobacterium*-mediated transient system (FIG. 2). Several methods were used to optimize chimaera expression in plants; including use of a NSs silencing suppressor, use of an agroinfiltration-delivered self-replicative viral vector and targeting of the expressed protein to the chloroplast.

Co-expression with the NSs Silencing Suppressor

*Agrobacterium*-mediated transient expression typically peaks 60-72 hours (~3 days) post-infiltration and then declines rapidly as a result of triggering post-transcriptional gene silencing (PTGS) in the host plant (Voinnet, 2001). PTGS is an adaptive anti-viral plant defense mechanism, where foreign RNA molecules are recognized and degraded in a sequence-specific manner (Heins, 2000; Sijen and Kooter, 2000). As a counter-defensive strategy, many plant viruses have evolved proteins that suppress various steps of the mechanism (Voinnet, 2001). Although PTGS responses reduce transgene mRNA accumulation in the plant cytoplasm and limit the efficiency of *Agrobacterium*-mediated transient expression (de Carvalho et al., 1992; Van Blokland et al., 1994), co-expression of proteins with viral silencing suppressors has been shown to repress PTGS responses and allow high level transient expression, resulting in higher yields (50-fold in some instances) and prolonged expression of the transgene (Voinnet et al., 2003).

Co-infiltration with the tomato spotted wilt virus (TSWV) silencing suppressor NSs suppresses PTGS and increases transient expression (Takeda et al., 2002). This effect was similarly observed in the transient expression of the L1/L2 chimaeras (FIG. 2). Chimaeras typically displayed maximum expression levels 3-5 dpi without the presence of viral silencing suppressors. However, co-expression with NSs displayed a prolonged increase in the expression of the chimaeras, whereby expression levels were increased by up to 16-fold and peaked 5-7 dpi.

The Use of a Self-replicative BeYDV Vector

Cytoplasmic HPV-16 L1 yields have been improved by 50% using a self-replicative pRIC vector (Regnard et al., 2010). As a result, a third-generation pRIC3 vector was examined as a potential strategy to improve chimaera yields. Three L1/L2 chimaeras were examined: L1/L2(108-120), L1/L2(56-81) and L1/L2(17-36). All chimaeras demonstrated higher expression levels using pRIC3 (self-replicative vector), in comparison to pTRAc (non-replicative vector), suggesting transgene amplification improves L1/L2 yields in the plant cytoplasm (FIG. 3a and b). However, chloroplast-targeting was more effective in the high-level accumulation of L1/L2 chimaeras (FIG. 3b) and visible necrosis of the leaf tissue was observed in pRIC3-infiltrated leaves, suggesting the self-replication of the vector negatively affects plant health.

Chloroplast-targeting of L1 Chimaeras

L1 chimaeras were targeted to the chloroplast using the pTRAkc-rbcs1-cTP vector. The chloroplast transit peptide (cTP) is fused to the expressed chimaera and is cleaved by the chloroplast stromal processing peptidase (SPP) upon entry into the organelle (Robinson and Ellis, 1984). There are several factors responsible for the high level accumulation of protein in chloroplasts: (a) protection from cellular proteases, (b) different protein hydrolyzing machinery in the plastids and (c) protective plasmid-specific chaperones which assist in the correct folding of L1 and thus improve protein stability (Fernández-San Millán et al., 2008). In this study, chloroplast-targeting was highly effective and increased L1/L2 chimaera yields by 40 to 80-fold in comparison to chimaeras targeted to the cytoplasm (FIG. 3a).

The chloroplast-targeted chimaeras detected in the anti-L1 western blots produced bands of ~56 kDa (FIG. 2), suggesting the signal peptide was effectively removed from the accumulated protein. Although L1/L2(108-120) runs higher than the other chimaeras on the western blot (FIG. 2), this phenomenon in not caused by insufficient cleavage of the signal peptide, as the cytoplasm-localised L1/L2(108-120) expressed with pTRAc, and insect cell-expressed L1/L2(108-120) analysed in parallel (data not shown), showed a similar banding pattern.

Higher molecular weight bands of ~65 kDa were detected for L1/L2(17-36) chimaeras (FIG. 2), possibly as a result of glycosylation or insufficient denaturation of chimaeras. A glycosylated form of HPV-16 L1 produced in baby hamster kidney cells (BHK) was described by McLean et al. (1990), whereby CamVir1 detected 2 bands for L1: the 56 kDa L1 major band and a minor band of ~64 kDa. The additional band was subsequently removed from cell lysates when infected in the presence of the N-glycosylation inhibitor tunicamycin. Although plants do contain glycosylation pathways (Rybicki, 2009), subsequent western blots displayed a single ~56 kDa band, suggesting the L1/L2(17-36) chimaeras were partially denatured in initial experiments rather than glycosylated (FIG. 3a).

Direct Comparison of Plant Expression Vectors

Two strategies have increased plant-expressed L1 yields to a maximum of 530-550 mg/kg (i) targeting the protein to the chloroplast (Maclean et al., 2007) or (ii) the use of an agroinfiltration-delivered self-replicative BeYDV-derived expression vector (Regnard et al., 2010). This was the first study which directly compared these strategies using the L1-based chimaeras. Chimaera expression levels using the plant expression vector pRIC3 (self-replicative, cytoplasm-targeting vector) was directly compared to pTRAkc-rbcs1-cTP. Expression using the pTRAc (non-replicative, cytoplasm-targeting vector) was included for comparative purposes and HPV-16 L1 was used as a positive control (FIG. 3a and b).

Chloroplast-targeting produced the highest yields for the majority of chimaeras (FIG. 3a and b) and improved L1/L2 chimaera expression by up to 7-fold relative to pRIC3, and 28-fold relative to pTRAc, both which target the expressed protein to the cytoplasm (FIG. 3b). Statistical analysis revealed that the chloroplast-targeted L1/L2 yields were significantly higher than the cytoplasm-targeted L1/L2 yields (p<0.01). However, yield differences between chloroplast-targeted chimaeras and chimaeras expressed using the self-replicative pRIC3 vector were only significant for L1/L2(56-81). These results provide evidence that pTRAkc-rbcs1-cTP is the best vector to use for the high-level production of HPV chimaeras.

Expression of the L1/L2 Chimaeras

Highly-expressed L1/L2 Chimaeras Containing the HPV-16 L2 Epitopes

The L1/L2(108-120), L1/L2(56-81) and L1/L2(17-36) chimaeras were highly-expressed, with yields up to 20-fold higher than the other chimaeras (Table 4). As a result, these three L1/L2 chimaeras were chosen as vaccine antigens for the mouse immunogenicity studies.

Chloroplast-targeted L1/L2 chimaeras consistently demonstrated the highest chimaera yields of ~1200 mg/kg plant tissue (2-3% TSP). Although HPV-16 L1 demonstrated higher yields than the L1/L2 chimaeras, the differences were not statistically significant (FIG. 3b). This indicates that the L2 epitopes do not significantly affect the expression and accumulation of HPV protein in chloroplasts. Furthermore, the chimaera yields are ~2-fold higher than published HPV-16 L1 yields produced using an *Agrobacterium*-mediated tobacco expression system (Maclean et al., 2007; Regnard et al., 2010) and the production of these chimaeras is commercially viable (>1% TSP; Fischer et al., 2004).

Assembly into higher-order structures is associated with a lower susceptibility to proteolysis (Chen et al., 2000) and it was hypothesized that the high accumulation of L1/L2 may be as a result of assembly. The conformational-specific H16.V5 MAb binds assembled protein (Christensen et al., 1996) and can be used to detect assembly into higher-order structures (Carter at al., 2003; Wang et al. 2003; Ryding et al., 2007). All plant-expressed L1/L2 chimaeras and the HPV-16 L1 control appeared to contain a low proportion of assembled protein (<20% TSP), suggesting majority of the protein exists as unassembled L1 monomers. However, both the L1/L2(56-81) and L1/L2(17-36) chimaeras contain L2 sequences overlapping the L1 C-terminal region aa 428-483 shown to be critical for the binding of H16.V5 (Varsani et al., 2006b), suggesting this MAb may not be suitable for detection of chimaera assembly and cannot be used for comparable quantification.

Instability of the L1/L2 Chimaera with the BPV L2 Aa 1-88 Epitope

The L1/L2 BPV(1-88) chimaera had low expression levels in comparison to the chimaeras containing the HPV-16 L2 epitopes (FIG. 2). ELISA quantification estimated expression levels were similar to the NSs negative control, although L1/L2 BPV(1-88) was detected on western blots probed with H16.J4 MAb and showed low yields of 40 mg/kg plant tissue (FIG. 2, ELISA data not shown). In addition, the chloroplast-targeted L1/L2 BPV(1-88) was partially degraded (FIG. 2D), which has been previously described in several HPV L1 expression studies (Hagensee et al., 1993; Sasagawa et al., 1995; Li et al., 1997; Kohl et al., 2007).

These results provide evidence that L1/L2 BPV(1-88) is not well-expressed, neither is it stable in the present plant expression system. The L1/L2 BPV(1-88) chimaera contains the largest L2 sequence replacement and the 88 residue epitope replaced the entire C-terminal region of L1 (Table 1). The HPV L1 C-terminal region plays a role in VLP assembly (Zhou et al., 1991b; Varsani et al., 2006b; Bishop et al., 2007), and deletion of the C-terminal region prevents assembly into higher-order structures which are less susceptible to degradation (Chen et al., 2000). Sequence replacement of the L1 C-terminal region with foreign epitope sequences is not an effective strategy for HPV chimaera expression and plants are not a viable system for L1/L2 BPV(1-88) expression.

Example 2

Purification and Assembly of HPV Antigens

Methods and Materials

Large-scale Transient Expression and Extraction of Antigens

*N. benthamiana* plants (2-4 weeks old) were vacuum-infiltrated with *A. tumefaciens* LBA4404 (pBIN-NSs) encoding the NSs silencing suppressor protein and the *Agrobacterium* GV3101 strain encoding HPV-16 L1 or the L1/L2 chimaeras, as described by Maclean et al. (2007). The plants were grown for 5 days in 16 hr light, 8 hr dark, at 22° C.

The infiltrated leaves were harvested, weighed and ground in liquid nitrogen using a mortar and pestle. PBS extraction buffer, containing 0.5M NaCl and protease inhibitor (Roche Complete EDTA-free), was added at a ratio of 1:4 (w/v) and samples were homogenized in a Waring blender for 10 min on ice. The homogenate was sonicated on ice for 6×20 s intervals of sonication and rest (Macrotip sonication; Level 8; Heat Systems—Ultrasonics, Inc. Sonicator Cell Disruptor Model W-225 R), and the lysate was filtered through a double layer of Miracloth (CALBIOCHEM). The crude extract was clarified twice by centrifugation at 13,000 rpm for 10 min. Pellets were resuspended in 1 ml PBS and stored at −70° C. The supernatant and pellet were examined by western blotting to check for localization of the HPV antigen to the supernatant.

Pilot Purification of HPV Antigens

Several methods were examined for the purification of plant-expressed L1 vaccine antigens. Size-based methods such as cross-flow microfiltration and ultracentrifugation using sucrose and caesium chloride density gradients were tested, as well as single-step cation-exchange and heparin chromatography for the rapid purification of L1 and L1-based chimaeras. L1 protein extracted in PBS containing 0.5M NaCl was diluted 10× in low-salt PBS (LS PBS: 10 mM NaCl PBS, pH 7.4) prior to chromatography, to allow L1 binding to the columns. Ultrafiltration was utilized to concentrate antigens and desalt chromatography fractions for downstream application in mouse immunogenicity studies.

Overall, purification using heparin chromatography and diafiltration using Macrosep® ultrafiltration spin tubes were the best strategies to obtain partially-purified L1 and L1-based chimaeras, and these methods were used to prepare the vaccine antigens for subsequent mouse immunological experiments.

Purification of Vaccine Antigens

Sample Preparation

HPV-16 L1 and L1-based chimaeras were expressed in *N. bethamiana* and extracted as described above in Example 1 using LS PBS as the extraction buffer. The double-clarified crude supernatant for L1/L2(108-120), L1/L2(56-81), L1/L2 (17-36), HPV-16 L1 and the NSs-infiltrated plant extract (Vaccines 1-5 respectively) was filtered through a 0.22 μm Millipore filter prior to chromatography to remove any debris.

Heparin Chromatography

Chromatography was performed using an ÄKTA Explorer System 10. The procedure was followed as recommended in the GE Healthcare column instruction manual and a flow rate of 0.5 ml/min was maintained. The column was equilibrated with 10 column volumes (cv) of low salt wash buffer (LS PBS: 10 mM NaCl PBS) prior to loading the sample. The crude extract (10-20 ml) was loaded on a pre-packed 1 ml HiTrap Heparin cation-exchange column (GE Healthcare, Amersham Biosciences AB, Sweden) and the column was washed with 10 cv of LS PBS wash buffer. The elution profile for each HPV antigen was optimized in a pilot experiment using a linear ionic strength gradient, whereby 10 cv of 0-100% of a high salt PBS (HS PBS) elution buffer containing 1.5M NaCl was applied to the column. Once it had been established that all antigens eluted when <50% HS PBS was applied to the column, a 50% step elution gradient (0.75M NaCl) was applied for purification of the vaccine antigens. The step elution gradient was 10 cv of 50% HS PBS, followed by 10 cv of 100% HS PBS. The column was finally washed with 5 cv of distilled water and 5 cv of 20% ethanol. Fractions (1 ml) were collected and analyzed by western dot blots.

Western Dot Blot Detection of Purified HPV Antigens

The dot blots were performed as described above in Example 1. CamVir1 (1:10000) was used to detect L1 and Cervarix was used as a positive control. Eluted fractions containing a high concentration of purified antigen were pooled and stored at −70° C. For the NSs-infiltrated plant extract (V5: negative control), the fractions which corresponded with the eluted protein peak were pooled and tested on the L1 positive control vaccine (V4) dot blot, to confirm it did not contain L1.

Desalting of Purified Antigen Samples by Ultrafiltration

The purified antigens in the 50% HS PBS elution buffer (0.75M NaCl), were desalted prior to mouse vaccinations. Ultafiltration spin tubes with 10 kDa MWCO filter (Macrosep® Centrifugal Devices, 10K Omega, PALL Life Sciences) were used to concentrate and desalt the purified L1 fractions rapidly by centrifuging the samples at 7000 g for 15-30 min. The retentate containing the L1 antigens was diluted in LS PBS and re-concentrated by ultrafiltration several times as per the manufacturer's instructions until the samples contained a NaCl concentration similar to that found in commercial PBS (~0.15M NaCl). Both the retentate and filtrate fractions were examined, Analysis of Antigen Purity

Coomassie Staining and Western Blot Detection of HPV Antigens to Assess Purification The crude extract and purified sample for each of the vaccine antigens was compared by Coomassie staining and western blot analysis. Samples were prepared as described in Example 1 above and equal volumes were loaded into two 10% SDS-PAGE protein gels. One gel was stained with Coomassie solution overnight at room temperature and destained 2×2 hr at 37° C. The other gel was blotted onto nitrocellulose membrane and probed with CamVir1.

Total Soluble Protein Quantification

The negative control vaccine (V5: NSs-infiltrated plant extract) cannot be quantified by anti-L1 western blotting. As a result, the amount of total soluble protein (TSP) was determined for each vaccine antigen using the Biorad Lowry protein assay (described in above in Example 1) to ascertain that the TSP was similar for all vaccines.

Detection of HPV Antigens by Capture ELISA to Determine Enrichment of Antigen Relative to the TSP A capture ELISA was performed as described in Example 1, using the linear epitope-specific monoclonal antibody (MAb) H16.J4. The HPV antigen yields determined by ELISA were compared to corresponding TSP yields in both the crude and purified samples to determine antigen enrichment.

Western Blot Quantification of Purified Vaccine Antigens

A dilution series of the vaccine Cervarix (containing 40 ug/ml of insect cell-produced HPV-16 L1) was used to quantify the plant-produced HPV antigens (V1-4). Several dilutions of the antigen were analyzed to ensure quantification occurred within the linear range of the standard curve. Equal volumes of purified antigens and Cervarix dilutions were loaded into 10% SDS-PAGE gels, proteins were blotted onto nitrocellulose membrane and the HPV antigens were detected with CamVir1 (1:10000).

Densitometry (GeneTools, Syngene, Synoptics Ltd) was used to quantify the antigens (as done by Aires et al., 2006; Bazan et al., 2009) and the amount of HPV protein present in the samples was determined using the standard curve generated by the Cervarix dilution series. Quantified HPV antigens were stored at −70° C.

Cytoplasmic Expression and Extraction of Antigens

In order to establish whether small virus like particles are also formed when chimaeric HPV L1/L2 proteins are targeted to the cytoplasm, as opposed to the chloroplasts, N. benthamiana plants were infiltrated with recombinant Agrobacterium harbouring pRIC L1/L2 (108-120); L1/L2 (56-81) and L1/L2 (17-36) together with the silencing suppressor NSs using the methods described above. After 3 to 5 days the infiltrated leaves were harvested, ground up and cell debris was removed by centrifugation.

Structural Analysis by Transmission Electron Microscopy

Aliquots of the purified vaccine antigens were pre-treated as if they were being prepared for mouse vaccinations. The antigens were defrosted overnight at 4° C., resuspended in PBS to the required concentration and incubated at 37° C. for 30 min.

To determine the effect of purification, the pre-treated purified antigens and the crude plant extracts for each antigen were diluted 10× in PBS, immunotrapped using CamVir1 (1:1000), a linear epitope-specific HPV-16 L1 antibody which binds both L1 monomers and assembled L1 protein (McLean et al., 1990), and captured on glow-discharged carbon-coated copper grids. The proteins were negatively stained with 2% uranyl acetate and viewed on a Zeiss 912 Omega Cryo EFTEM.

Results

Purification of Plant-expressed HPV Antigens

Detection of HPV Antigens in the Clarified Extract

The localisation of L1 and the L1/L2 chimaeras to the clarified supernatant was confirmed by western blot analysis. The Coomassie-stained protein gel indicated the abundant presence of Rubisco in the supernatant and the removal of several contaminating proteins present in the pellet (data not shown).

Pilot Purification of HPV Antigens

Purification using size-based techniques was largely unsuccessful and not reproducible between the vaccine antigens, as the L1/L2 chimaeras appear to assemble into a variety of structures in contrast to L1. In addition, protein degradation was detected and thus purification using chromatography was examined as an alternative method.

Although cation-exchange chromatography using the HiTrap SPFF or POROS 50HS column was unsuccessful in the purification of the L1-based chimaeras, heparin affinity chromatography purified all the vaccine antigens. The concentration and removal of salt in the chromatography fractions was examined using two ultrafiltration-based methods, either by cross-flow filtration or centrifugation spin columns. Although cross-flow ultrafiltration was effective, the method was costly with regard to time and significant protein degradation was detected, resulting in the preferential use of spin columns. Thus, heparin chromatography and centrifugation ultrafiltration were considered the best strategies to purify the vaccine antigens for subsequent mouse immunological experiments.

Purification Using Heparin Chromatography

Vaccine antigens were purified from the clarified crude plant supernatant by heparin chromatography using a high NaCl gradient for elution of the HPV antigens. The step elution gradient was optimised for each HPV antigen using a linear 0-100% 1.5M NaCl gradient. All HPV antigens eluted between 0.45-0.75M NaCl (data not shown). As a result, a 50% (0.75M NaCl) step gradient was used to purify the vaccine antigens for the mouse immunogenicity study. Detection of the purified HPV antigens in the eluate fractions was determined using CamVir1 dot blots.

An absorbance peak was detected when the HS PBS elution buffer was applied to the column and these fractions contained the purified HPV antigens. The chromatograms for the other vaccine antigens were similar, including the graph for the NSs-infiltrated plant extract (negative control). This indicates that the HPV antigens were co-purified with other contaminating plant proteins.

The fractions containing the partially-purified HPV antigens (or co-eluted plant proteins for the negative control) were pooled and then desalted using ultrafiltration spin columns. Western dot blots indicated that the HPV antigens were successfully retained and concentrated (data not shown).

Purity of the Vaccine Antigens

The purity of the vaccine antigens was examined by comparing the purified sample to the crude plant extract. This was done using Coomassie staining, to indicate total protein present in the samples (FIG. 5A), and western blot analysis, to detect the HPV antigens and indicate the loss in antigen yield (FIG. 5B). Note that the L1/L2(108-120) chimaera (V1) runs higher than the other L1/L2 chimaeras (V2-3) and the L1 control (V4).

FIG. 5 shows the purified samples were enriched with L1 as a result of the purification procedure. The Coomassie-stained gel shows a large decrease in the total protein in the purified samples, while the western blot results indicate that there is only a small decrease in antigen yield after purification. The L1 antigen was not detected in the negative control (V5: NSs-infiltrated plant extract).

Samples were only partially-purified, as additional Coomassie-stained protein bands were detected in FIG. 5A for purified antigens V1 and V3 (more concentrated than V2 and V4), thus demonstrating that the purified samples contain several contaminating plant proteins. Also, although the NSs negative control (V5) was not detected on the western blot, several similar Coomassie bands were seen in the purified NSs sample.

Enrichment of HPV Antigens in Purified Samples

The TSP of the purified antigens was determined to: (a) ensure that the TSP was similar for the NSs negative control (containing plant proteins which were co-purified with the HPV antigens) in comparison to the other vaccine antigens, and (b) to determine HPV antigen enrichment after purification. The TSP for the purified HPV vaccine antigens (V1-4) was similar, however the TSP for the NSs plant extract negative control (V5) was almost 2-fold higher, possibly as a result of more eluate fractions being pooled or greater ultrafiltration concentration (data not shown). As a result, it was diluted accordingly in 1×PBS.

Capture ELISA, using the linear-specific H16.J4 MAb was used to estimate the amount of HPV antigen present in the crude and purified samples. To determine the effect of purification on the TSP and the enrichment of HPV antigens, the H16.J4-detected HPV yield was directly compared to the TSP yield for both the crude and purified samples (FIG. 6).

FIG. 6 demonstrates that purification of the plant extracts reduced both the TSP and total HPV protein, as expected. However, relative to the TSP, there is up to a 5-fold enrichment of HPV antigen in purified samples (V1-4), suggesting that heparin chromatography is effective in removing a large proportion of contaminating protein. The NSs-infiltrated plant extract (V5) showed a similar decrease in TSP with purification and the amount of TSP in the "purified" negative control lies within the levels obtained for the HPV vaccine antigens (V1-4).

Western Blot Quantification of Purified HPV Antigens

HPV antigens were quantified by western blotting using densitometry and the commercial vaccine Cervarix as the standard (data not shown). Some L1 protein degradation, visible as a ~45 kDa band, was detected in some of the purified antigen batches, particularly after several freeze-thaw cycles. However, only the full-length 56 kDa L1 band was quantified in the samples prepared for mouse immunogenicity studies.

Structural Analysis of Purified Vaccine Antigens

The structural assembly of L1 and the L1/L2 chimaeras produced in the choloroplasts of plants in both the crude and purified samples was analysed by immunocapture transmission electron microscopy (FIG. 7). The structural assembly of the L1/L2 chimaeras produced in the cytoplasm were analysed by immonocapture transmission electron microscopy from crude samples (FIG. 8). Antigen purification resulted in the removal of contaminating background protein, particularly for L1/L2(108-120) and the negative control (FIGS. 7A and E respectively). In comparison to the negative control (NSs-infiltrated plant extract), all the HPV antigens appeared to contain secondary HPV structures, either capsomeres (~10 nm), capsomere aggregates, small VLPs (~30 nm) or full-sized VLPs (55 nm).

Purified L1/L2(108-120) assembled into small chimaeric VLPs (cVLP) which were regular in shape but varied in size (~30 nm), while L1/L2(56-81) only appeared to contain capsomeres and some aggregates, although VLP-like structures were visible in the crude extract. Purified L1/L2(17-36) contained a mixed population of amorphous cVLPs and a high proportion of capsomere aggregates in contrast to the crude extract, suggesting purification promoted the formation of higher-order structures. Purified V4, the HPV-L1 positive control, assembled into distinct VLPs (~50 nm), as described in previous studies (Biemelt et al., 2003; Maclean et al., 2007).

Discussion

Stringent purification is necessary for the commercial production of vaccines, although the stability of L1 is negatively affected by multiple purification steps. Heparin affinity chromatography can be utilized to selectively purify assembled L1, and a purification strategy using a one-step chromatography method would be ideal for the rapid and cost-effective production of HPV vaccines. This study reports the purification of plant-expressed HPV-16 L1 and three L1/L2 chimaeras using heparin chromatography for subsequent immunogenicity studies in mice.

Optimisation of LAM Chimaera Purification

HPV-16 L1 and the L1-based chimaeras were localized to the crude extract supernatant and were purified using a variety of methods. Although size-dependent purification methods have been used to purify plant-expressed HPV L1 (Biemelt et al., 2003; Maclean et al., 2007; Fernández-San Millán et al., 2008), these methods were inefficient for L1/L2 chimaera purification and were non-reproducible between antigens. The L1-based chimaeras were broadly detected in several fractions using both sucrose and CsCl density gradient ultracentrifugation, indicating that the L1/L2 chimaeras assembled into heterologous higher-order structures, such as capsomeres, aggregates and VLPs. Furthermore, the extent of assembly appeared to differ between the chimaeras and the L1 positive control. This was confirmed by transmission electron microscopy (FIG. 7), which showed distinct differences between the different L1/L2 chimaeras and the L1 control.

Chromatography was the next strategy to selectively purify HPV L1; either on the basis of surface charge, or by affinity for the proteoglycan heparin. The use of cation-exchange chromatography for the purification of yeast-expressed HPV L1 has been demonstrated using P-11 phosphocellulose (Kim et al., 2009, 2010) or a POROS 50HS column (Cook et al., 1999). In contrast, the plant-expressed L1/L2 chimaeras were not purified efficiently using either the strong cation-exchange HiTrap SPFF column or the POROS 50HS column. The majority of L1/L2 protein did not bind to either column, although a small proportion of protein bound strongly and irreversibly to the POROS 50HS resin. This phenomenon has been described by Cook et al. (1999), whereby 10% of HPV-11 L1 did not bind the resin and 45-65% could not be recovered without stripping the POROS 50HS column using 0.5M NaOH.

As a result, cation-exchange chromatography was not pursued further, although the reason for the poor purification of L1/L2 chimaeras is not clear. There are two HPV-16 L1 basic C-terminal regions which contain positively charged residues: aa 473-488 and 492-505 (Zhou et al., 1991b; Sun et al., 1995, 2010). The L2 sequence insertions did not overlap the major basic regions in the C-terminal of L1 and replaced a maximum of 26 residues at aa 414-439. A possible explanation is that the overall surface charge of L1 was affected, either by the amino acid composition of the inserted L2 epitopes, or by differences in protein assembly. In addition, the crude plant extract may have contained several contaminating proteins which bound more strongly to the columns and out-competed HPV L1 binding.

Purification of the Vaccine Antigens

Vaccine antigens were purified using heparin chromatography (described by Joyce et al., 1999; Bazan et al., 2009; Johnson et al., 2009; Kim et al., 2009, 2010) for subsequent immunogenicity studies in mice. Heparin reversibly bound both the L1 and L1/L2 chimaeras in a similar manner (data not shown), and all antigens eluted with 0.75M NaCl. This is comparable to other studies where heparin-bound HPV-16 L1 eluted between 0.5-1.2M NaCl (Bazan et al., 2009; Kim et al., 2010; Baek et al., 2011).

Heparin selectively purifies assembled L1 protein by binding to a conformational motif which is not present on the C-terminal of L1 (Fleury et al., 2009) and is unaffected by the L2 sequence replacements. This is particularly beneficial for vaccine production, as denatured L1 does not elicit the production of neutralising antibodies (Kirnbauer et al., 1992; Suzich et al., 1995; Breitburd et al., 1995). Furthermore, Kim et al. (2010) demonstrated that purification of HPV-16 L1 using heparin chromatography gave high recovery yields (~60%) and produced immunogenic VLPs (25-65 nm in diameter).

The purity of the heparin-purified samples was examined by Coomassie staining and western blot detection of L1 using CamVir1 (FIG. 5). The purified samples were enriched with L1 or L1/L2 chimaeras, as there was a significant decrease in total protein with a relatively small decrease in antigen yield when compared to the crude samples. This was confirmed by H16.J4 capture ELISA and TSP assays (FIG. 6).

Samples were partially-purified and contained several contaminating plant proteins (V1 and V2, FIG. 5A), also present in the purified negative control (V5, FIG. 5A). Contaminants were also observed in the purification of yeast-expressed HPV-16 L1 using heparin chromatography (Kim et al., 2010). As a result, a single step method using heparin chromatography is not sufficient to obtain highly-purified HPV L1 and 121/L2 chimaeras. Kim et al. (2010) demonstrated that co-purified contaminating proteins from yeast were not completely removed by additional cation-exchange and hydrophobic interaction chromatography steps, suggesting many of the contaminants have similar isoelectric points and hydrophobicity profiles to L1. Furthermore, the additional chromatographic steps reduced L1 recovery to ~10%. However, pure HPV-16 L1 was obtained by ammonium sulphate precipitation of yeast-expressed HPV-16 prior to heparin chromatography, a method which should be examined in further purification studies using plant-expressed HPV L1-based proteins.

Western Blot Quantification of Antigens

The purified antigens were quantified by western blot analysis (discussed by Heidebrecht et al., 2009) using densitometry to measure the intensity of the CamVir1-detected L1 bands and the commercial vaccine Cervarix as the HPV-16 L1 standard (data not shown).

L1 degradation was detected in some of the batches of purified antigen, particularly after several freeze-thaw cycles. This was seen at high concentrations of V1, V2 and V4. However, the majority of the antigen proteins were not degraded and only the full-sized 56 kDa L1 band was quantified to ensure mice were immunized with similar doses of full-length antigen. Other groups have reported similar HPV-16 L1 degradation patterns when expressed in insect cells (Kirnbauer et al., 1992), yeast (Cook et al., 1999) and bacteria (Zhang et al., 1998). A consideration for future purification studies is the salt concentration of the extraction and diafiltration buffers, as VLP disassembly occurs in low-salt conditions (Murata et al., 2009). Increasing the salt concentration to 0.5 or 1M NaCl may stabilizes VLPs (Mach et al., 2006) and reduce degradation observed in the purified samples.

Assembly of the Vaccine Antigens

The assembly of plant-derived HPV-16 L1 and the L1/L2 chimaeras produced in the chloroplasts of plant cells was analysed using immunocapture electron microscopy (FIG. 7). Purification appeared to remove some background protein and all the plant-expressed L1/L2 chimaeras and the L1 positive control assembled into higher-order structures such as capsomeres, aggregates and VLPs.

Plant-expressed HPV-16 L1 VLPs are typically ~55 nm in diameter when localised to the tobacco chloroplasts (Maclean et al., 2007; Fernández-San Millán et al., 2008; Lenzi et al., 2008). In this study, HPV-16 L1 assembled into full-sized VLPs (~50 nm, FIG. 7 Dii).

Assembly of chimaeras into VLPs appears to be affected by the length of the L2 epitope, with L1/L2(108-120), L1/L2(17-36) and L1/L2(56-81) containing 13, 20 and 26 residue epitope replacements respectively. Plant-expressed L1/L2(108-120), with the shortest L2 epitope, successfully assembled into distinct cVLPs of about ~30 nm in diameter, which is smaller than L1 VLPs (Chen et al., 2000) FIG. 7A). In contrast, L1/L2(17-36) predominantly formed capsomere aggregates, although the presence of larger amorphous VLP-like structures suggest there may be partial-assembly of small cVLPs (FIG. 7C). Finally, L1/L2(56-81) with the longest L2 epitope predominantly assembled into capsomeres (FIG. 7B).

L1/L2(108-120) has also been expressed in insect cells and the CsCl-purified chimaera was shown to assemble into amorphous VLPs and capsomere aggregates (Varsani et al., 2003a), rather than discrete cVLPs of ~30 nm diameter.

Chimaeras targeted to the cytoplasm as a result of infiltration of plants using the pRIC expression vector resulted in the formation of detectable L1/L2(56-81) VLPs (FIG. 8). This indicates that the chimaeric VLPs described herein can also be formed in the cytoplasm of plants.

Example 3

Immunogenicity of L1/L2 Chimaeras

In this study, mice were immunized with plant-derived L1 and three L1/L2 chimaera candidate vaccines containing the cross-neutralising L2 epitopes aa 108-120, 56-81 and 17-36. The immunogenicity of the chimaeras was analysed with respect to chimaera assembly and their ability to elicit anti-L1, anti-L2 and protective NAb against homologous HPV-16 and heterologous HPV-18, 45 and 52 PsVs was investigated.

Methods and Materials

Immunisation of Mice

Female C57/BL6 mice from the South African Vaccine Producers Animal Unit (Johannesburg, South Africa) were maintained under Biosafty Level 2 (BSL-2) conditions in the Animal Unit in the Health Science Faculty, University of Cape Town. Permission for this study was granted by the Research Ethics Committee, University of Cape Town (AEC 008/037).

Mice (7-8 weeks old) were immunised to test humoral antibody responses to plant-derived HPV-16 L1/L2 candidate vaccines. The controls included plant-expressed HPV-16 L1 (positive control) and NSs-infiltrated plant extract (negative control). The L1/L2(108-120) chimaera (published as SAF; Varsani et al., 2003a) has been shown by our laboratory to illicit anti-L1 responses and thus served as an additional positive control. The vaccination details are shown in Table 5.

TABLE 5

Plant-derived vaccine antigens used in the immunogenicity study

| Vaccine | Vaccine No. (*n = 10) | Group No. (*n = 5) | Antigen dose (μg) | †TSP (mg/ml) |
|---|---|---|---|---|
| L1/L2(56-81) | V2 | G3 & G4 | 10 | 0.14 |
| L1/L2(17-36) | V3 | G5 & G6 | 10 | 0.09 |
| HPV-16 L1 (+) | V4 | G7 & G8 | 10 | 0.33 |
| Plant extract (−) | V5 | G9 & G10 | N/A | 0.16 |

*n = number of mice
†TSP = total soluble protein

The purified vaccine antigens were adjusted to contain a 10 μg dose in 100 μl Dulbecco's PBS (DPBS; Sigma). The total soluble protein (TSP) in each vaccine was assessed using a Bradford protein assay as discussed in Example 1 above to ensure the negative vaccine control contained a similar TSP in comparison to the other HPV vaccines (Table 5). The vaccine was prepared by homogenization of the vaccine antigen in Freund's Incomplete Adjuvant (FIA) in a 1:1 volume ratio using the syringe-extrusion technique (Koh et al., 2006).

Mice were divided up into 2 groups of 5 mice per vaccine and were subcutaneously injected into the right flank, left flank or the inguinal site. Pre-bleeds were taken 12 days prior to vaccination (Day 0) and mice were boosted on Day 13, 27, 41 and 48 (approximately every 2 weeks, except for Day 48 when it was decided to boost rather than obtain a test bleed) before obtaining the final bleeds at Day 62 (~9 weeks post-vaccination). Serum was isolated and stored at −70° C.

ELISA Detection of Anti-L1 Antibodies in Mouse Sera

Preparation of the Insect Cell-Produced HPV-16

Insect cell-produced HPV-16 L1 was used as an ELISA antigen to detect anti-L1 antibodies in the mouse sera. Insect cell-expressed L1 was used instead of plant-expressed L1 to avoid the background detection of antibodies against contaminating plant proteins. *Spodoptera frugiperda* (Sf-9) cells were grown shaking in SF90011 serum-free medium (Gibco) at 27° C. and infected at a multiplicity of infection (MOI) of 1.0 and a cell density of $1 \times 10^6$ cells/ml. Cells were harvested after 96 hrs by centrifugation (1000×g for 5 min) and pellets were washed with DPBS and stored at −70° C.

HPV-16 L1 was extracted by resuspending cells to $4 \times 10^6$ cells/ml in high-salt PBS (0.8M NaCl 1×PBS) containing protease inhibitor (Roche Complete EDTA-free) and sonicating on ice for 5×20 s intervals of sonication and rest (Microtip sonication; Level 5; Heat Systems—Ultrasonics, Inc. Sonicator Cell Disruptor Model W-225 R). The cell lysate was clarified by centrifugation (5000 g for 5 min) to remove cell debris and the centrifugation step was repeated using the supernatant. The commercial vaccine Cervarix (20 μg HPV-16 L1) was used as a HPV-16 L1 standard for western blot quantification of HPV-16 L1 (as described above) and L1 was detected with CamVir1 (1:10000; Abcam®).

ELISA Detection of Anti-L1 Antibodies

The anti-L1 antibody titre was determined by direct RASA. A 96-well Maxisorp microtitre plate (Nunc) was coated with 100 μl/well (30 ng) of insect cell-produced HPV-16 L1 antigen diluted in 1×PBS and incubated overnight at 4° C. Plates were blocked with blocking buffer (1% skim milk in 1×PBS; 200 ul/well) for 2 hrs at room temperature and then washed 4× with PBS.

Mouse sera were pooled into vaccines (10 mice/vaccine) for analysis. Final bleed mouse sera were diluted in blocking buffer in a 4-fold series in triplicate, ranging from a dilution of 1:50 to 1:51200. Pooled pre-bleed sera were tested at 1:50 dilution and served as a negative control. Diluted sera was added to the wells (100 μl/well) and incubated for 2 hrs at room temperature. Positive controls wells contained 1:50 dilution of anti-L1 antibodies; both CamVir1 (Abcam®), which binds both linear and conformational epitopes (McLean et al., 1990), and H16.V5 MAb, which binds specifically to conformational epitopes (Christensen et al., 1996). Blank wells with no antibody were included as a background control.

After a 4×PBS washing step, goat anti-mouse horseradish peroxidase conjugate (1:2000; Sigma) diluted in blocking buffer was added to the wells (100 ul/well) and incubated for 1 hr at 37° C. Plates were washed 4× with PBS (200 μl/well) and 100 ul of O-phenylenediamine dihydrochloride (OPD) (DAKO; Denmark) was added per well. Plates were developed in the dark for 30 min at room temperature, the reaction was stopped with 0.5M $H_2SO_4$ and the absorbance at 490 nm was detected. The anti-L1 binding titres were expressed as a reciprocal of the maximum serum dilution which produces higher absorbance readings than that of the corresponding pre-bleed serum diluted at 1:50.

Statistical Analysis

A two-tailed, non-paired t-test was used to calculate statistical significance of the final bleed anti-L1 response, as compared to the negative control vaccine (p=0.01). One-way Analysis of Varience (ANOVA) was used to compare the vaccines and the Fisher LSD, Turkey HSD and Bonferroni tests were used to determine the significance (p=0.01).

Western Blot Detection of Anti-L2 Antibodies

Preparation of *E. coli*-produced HPV-16 L2

His-tagged HPV-16 L2 protein produced using the pProEX htb vector in *E. coli* (provided by David Mutepfa) was used for the western blot detection of anti-L2 antibodies in mouse sera. *E. coli* cultures were grown shaking at 37° C. to an $OD_{500}$ of 0.6 and then induced by the addition of 0.6 mM iso-propyl-β-thiogalactoside (IPTG). After 3 hrs, cells were harvested by centrifugation (3800 g for 15 min at 4° C.) and the pellet was retained and weighed.

The inclusion bodies were extracted by resuspension of the cells in 4 volumes of lysis buffer (50 mM Tris pH 8.5, 5 mM β-mercaptoethanol) and phenylmethanesulfonyl fluoride (PMSF) and lysozyme (Roche) was added to a final concentration of 0.4 mM and 0.08 μg/μl respectively. The cells were incubated on ice for 20 min, Triton-X was added to 1% and cells were further incubated for 20 min at 37° C. until the solution was viscous. DNase and RNase were added to 4 μg/ml and 40 μg/ml respectively and cells were incubated for 30 min at room temperature until viscosity cleared.

The inclusion bodies were collected by centrifugation at 13,000 rpm in a microcentrifuge for 15 min at 4° C. and the pellet resuspended in 1 ml lysis buffer (2.5 mM Tris pH 8.0, 3.125 mM β-mercaptoethanol, 0.2 mM EDTA, 0.0025% Triton-X) and left to lyse for 10 min at room temperature. The sample was centrifuged at 13,000 rpm for 15 min at 4° C. and pellets were washed 4× with PBS. The pellet was resuspended in 1 volume PBS of the weight of pellet, quantified by Coomassie staining using a bovine serum albumin (BSA) standard and stored at −20° C.

Western Blot Detection of Anti-L2 Antibodies

The *E. coli*-produced HPV-16 L2 antigen was incubated at 95° C. for 5 min in 5× loading buffer and was loaded into a 10% SDS-PAGE gel. Instead of using a 10-well comb, a 2-well comb was used: a small well for the protein marker and a large well consisting of the 9 wells fused together, thus producing a single wide well which allowed the protein to spread equally across the width.

E. coli-expressed His-tagged HPV-16 L2 antigen (2.5 mg) was separated on a 10% SDS-PAGE gel (Sambrook et al., 1989) and transferred onto a nitrocellulose membrane by semi-dry electroblotting as described in Example 1 above. The western blotting protocol was then modified, whereby the portion of the membrane between 55-130 kDa containing the L2 protein (~80 kDa) was divided into 12 similar-sized strips to probe with different sera. The membrane strips were transferred into individual wells in a 25-well tissue culture plate and incubated in blocking buffer for 4 hrs at room temperature.

Individual pre-bleed and final bleed mouse sera were pooled into vaccines (10 mice per vaccine) and the membrane strips were probed with positive control mouse anti-His antibody (1:2000, Serotech) or pooled mouse sera diluted 1:100 in blocking buffer. Sera were added to different wells and incubated with shaking overnight at room temperature. The strips were then washed 4×10 min with blocking buffer and probed with secondary goat anti-mouse IgG antibody conjugated to alkaline phosphatase (1:5000; Sigma) for 2 hrs at room temperature. The individual strips were washed again for 4×10 min with wash buffer and then developed with NBT/BCIP (Roche).

Densitometry (GeneTools, Syngene, Synoptics, Ltd) was used to measure the absorbance intensity of each L2 band. Values were normalized for non-specific background absorbance using the value associated with the negative control vaccine. Sera with L2 bands having absorbance values >2× the value observed in the HPV-16 L1 final bleeds elicited an anti-L2 response.

HPV Pseudovirion Neutralisation Assays

Preparation for the Neutralisation Assays

The protocols used for the HPV pseudovirion (PsV) neutralisation assays are taken from Dr John Schiller's Lab of Cellular Oncology technical files and the HPV L1/L2 pSheLL plasmids and the pYSEAP reporter plasmid were kindly provided by Dr John Schiller.

The pYSEAP plasmid was checked using a SaiI and BamHI restriction enzyme digest (as described in Example 1 above). The HPV L1/L2 pSheLL plasmids were similar in size and have similar restriction enzyme sites, thus the plasmids were sequenced to confirm their identity using two sets of pSheLL vector-specific primers which bind upstream and downstream of the HPV L1 and L2 genes (Table 6). Sequences were aligned with the HPV L1/L2 pSheLL plasmid sequence and HPV L1 or L2 gene sequences using DNAMAN sequence analysis software.

TABLE 6 pSheLL vector-specific sequencing primers

| Sequencing target | Primer | Sequence | $T_m$ (° C.) | Size (nt) |
|---|---|---|---|---|
| HPV L1 | L1 Fwd | TGACCTTATGGGAC TTTCCTAC (SEQ ID NO 18) | 56.3 | 22 |
|  | L1 Rvs | CACCATAAGCAGCCACAAT (SEQ ID NO 19) | 55.5 | 19 |
| HPV L2 | L2 Fwd | TACCACCACGAACAAGCAC (SEQ ID NO 20) | 57.5 | 19 |
|  | L2 Rvs | AAGCCATACGGGAAGCAA (SEQ ID NO 21) | 55.4 | 18 |

Endotoxin-free plasmid DNA (NucleoBond® Xtra Midi EF, Macherey-Nagel) was prepared from E. coli cultures grown under the appropriate antibiotic selection for both the pYSEAP plasmid and HPV-16, 18, 45 and 52 pSheLL plasmids (Table 7) and DNA was stored at −70° C.,

TABLE 7

HPV PsV neutralisation assay plasmid vectors used in this study

| Plasmid | HPV type | Gene of interest | Size (bp) | Antibiotic resistance |
|---|---|---|---|---|
| p16 SheLL | HPV-16 | L1 & L2 | 10827 | Ampicillin (100 μg/ml) |
| p18 SheLL | HPV-18 | L1 & L2 | 10723 | Ampicillin (100 μg/ml) |
| p45 SheLL | HPV-45 | L1 & L2 | 10814 | Ampicillin (100 μg/ml) |
| p52 SheLL | HPV-52 | L1 & L2 | 10725 | Ampicillin (100 μg/ml) |
| pYSEAP | — | SEAP | 5297 | Blasticidin (75 μg/ml) |

Transfection of HEK293TT Cells

The HEK293TT cell line was kindly provided by Dr John Schiller. HPV PsVs were produced as described in the "Production of Papillomaviral Vectors (Pseudoviruses)" protocol revised in June 2010.

HEK293TT cells were cultured in complete high glucose Dulbecco's Modified Eagle Medium (cDMEM) containing 1% GlutaMAX™ (Gibco) and 10% fetal calf serum (Gibco). The cDMEM media was supplemented with 1% non-essential amino acids (Gibco), 100 units/ml penicillin (Gibco), 100 μg/ml streptomycin (Gibco), 10 μg/ml Fungin™ (invivoGen) and 250 μg/ml Hygromycin B (Roche) to select for the TT antigen (cDMEM-Ab). The thawing and passaging of cells was done as described in the protocol.

Cells were pre-plated in cDMEM (without antibiotics or Hygromycin 8) in a 175 cm² flask to reach 50-70% confluence the following day. On the day of transfection, fresh cDMEM was added to the cells and aliquots of endotoxin-free plasmid DNA were thawed on ice. The transfection mix was prepared as follows: 175 ul FuGene6 (Roche) was added to 5.7 ml DMEM with GlutaMAX (serum-free media) in white-capped conical tubes (Sterilin) and incubated for 5 min at room temperature. A total of 40 ug DNA was added (20 ug of each plasmid), the mixture was incubated for a further 30 min at room temperature and then added dropwise to the cells. Flasks were incubated for 40-48 hrs at 37° C. in a 5% $CO_2$ humidified incubator and the medium was changed 6 hrs post-transfection (cDMEM).

Extraction of Pseudovirions

Pseudovirions were harvested 40-48 hrs post-transfection. Cells were collected by trypsinisation with 0.05% Trypsin-EDTA (Gibco) and inactivated by the addition of cDMEM. The cells were transferred to a conical-bottomed polystyrene Sterilin tube (as pseudovirions adsorb non-specifically to polypropylene tubes), counted and centrifuged at 1200 rpm×8 min. The pellet was washed with 0.5 ml DPBS (Invitrogen) and resuspended in 1.5 pellet volumes of DPBS-Mg (DPBS with an additional 9.5 mM $MgCl_2$) to achieve a high cell density of >100×10⁶ cells/ml.

10% Brij-58 (Sigma) was added to the resuspended pellet to a final concentration of 0.5% (w/v) and both Benzonase (Sigma) and Plasmid-Safe™ ATP-dependent DNase (Epicentre) were added to 0.5% (v/v) and 0.2% (v/v) respectively. Using Chris Buck's "Improved Maturation of HPV and Polyomavirus" protocol, sterile ammonium sulphate (1M, pH 9.0) was added to a final concentration of 25 mM to promote the formation of intermolecular L1 disulphide bonds. The mixture was incubated at 37° C. for 15 min to allow lysis and then transferred to the preferred temperature for pseudovirion maturation overnight (25° C. for HPV-16 and 18, 37° C. for HPV-45 and 52).

The matured lysate was chilled on ice for 5 min and the final NaCl concentration of the lysate was adjusted to 850 mM and incubating on ice for a further 10 min. The lysate was clarified by centrifuging 3000×g for 10 min at 4° C. The supernatant was collected and the pellet was re-extracted by resuspending in an equal pellet volume of high salt DPBS (0.8M NaCl) and re-centrifuging. The supernatants were pooled, re-centrifuged and transferred into white-capped polystyrene tubes and kept on ice.

Purification of Pseudovirions

PsV are purified by Optiprep density gradient centrifugation. Optiprep (60% w/v iodixanol solution; Sigma) was diluted in DPBS to a 46% (w/v) Optiprep stock solution, and supplemented with 0.625M NaCl to a final concentration of 0.8M NaCl, $CaCl_2$ to 0.9 mM, $MgCl_2$ to 0.5 mM and KCl to 2.1 mM. High salt DPBS (0.8M NaCl) was used to dilute the stock solution to 27%, 33% and 39% Optiprep, and the 3-step gradient was prepared by underlaying the Optiprep dilutions (27-39%) in 1.5 ml steps in thin wall 5 ml polyallomer ultracentrifuge tubes (Beckman). The gradient was left to diffuse at room temperature for 4 hrs. Double-clarified cell supernatant was layered onto the linearized Optiprep gradient and centrifuged in a Beckman SW55ti rotor at 50,000 rpm (234,000×g) for 3.5 hrs at 16° C. The bottom of the tube was punctured with a syringe needle and fractions were collected in white-capped polystyrene tubes: the first fraction was ~0.75 ml, fraction 2-11 was ~0.25 ml each and fraction 12 contained the remainder of the gradient.

The protocol for screening fractions was modified to detect the presence of HPV L1, the major protein present in the capsid (Buck et al., 2008), using HPV type-specific anti-L1 dot blots. Each fraction was spotted onto nitrocellulose membrane (0.5 µl) and Cervarix (HPV-16 L1), E. coli-produced His-tagged HPV-16 L2, or the clarified HPV-16, 18, 45 or 52 supernatant initially loaded onto the gradient was used as positive controls.

The membranes were blocked in blocking buffer for 30 min at room temperature and then probed overnight at room temperature with an appropriate primary anti-L1 antibody diluted in blocking buffer. CamVir1 (1:5000; Abcam) was used to detect HPV-16. In addition, rabbit anti HPV-16 L2 sera was available and used to detect L2 in the HPV-16 fractions (1:2000). The H16.I23, H45.N5, H52.C1 and H52.011 MAb kindly provided by Dr Neil Christensen were used to detect HPV-18, 45 and 52 respectively (1:2000; Christensen et al., 1996). Membranes were probed with 1:10,000 secondary antibody (goat anti-mouse IgG conjugated to alkaline phosphatase or goat anti-rabbit alkaline phosphatase conjugate; Sigma), washed and developed as described above. Peak fractions containing a high concentration of L1 were pooled in polystyrene tubes and stored at −70° C. for titration.

Electron Microscopy of Pseudovirions

Purified HPV PsV were analyzed using electron microscopy. The PsV's (1:1000) were trapped on glow-discharged carbon-coated copper grids, stained with 2% uranyl acetate and viewed using a Zeiss EM 912 CRYO EFTEM.

Pseudovirion Titration

The PsV titrations and neutralisation assays were based on the "Papillomavirus Neutralisation Assay" protocol, with the exception that no NAb were included in the titration. PsV stocks were titrated prior to the neutralisation assays in order to determine the minimum amount of PsV required for a robust signal in the SEAP assay.

HEK293TT cells were grown in cDMEM-Ab to 70-80% confluence, collected as described, washed with DPBS and diluted to $3.0 \times 10^5$ cells/ml in neutralisation media (High glucose cDMEM with HEPES and without phenol red or sodium pyruvate, supplemented with 10% fetal calf serum; Gibco). Cells were pre-plated into 96-well tissue culture treated plates (Corning Costar) with 100 µl cell suspension in each internal well and 150 µl DMEM with phenol red in the external wells to avoid evaporation from the inner wells. Cells were incubated for 3-4 hrs at 37° C. before the addition of the PsVs.

Serial dilutions of PsVs were prepared in neutralisation media (doubling dilutions from 1:250 to 1:64000) in non-treated sterile 96-well polystyrene plates (Nunc) and tested in triplicate. The PsV dilutions were added to the pre-plated cells (100 ul/well) as outlined in the Schiller protocol, and each plate contained 6 negative control wells with no pseudovirions (cell control). Plates were incubated for 72 hrs at 37° C. in a humidified $CO_2$ incubator.

SEAP activity was detected using the Great EscAPe™ SEAP Chemiluminescence Kit 2.0 (Clontech Laboratories, Inc.) according to manual instructions, except volumes were adjusted to 0.6 volumes of those given in the manufacturer's protocol (as done in the revised Schiller protocol). Supernatant (125 µl) was transferred into sterile untreated 96-well polysterene plates (Nunc) and centrifuged at 1000×g for 5 min. Clarified supernatant (15 µl) was transferred into a white 96-well Optipiate (96F white maxisorb luminometer plates; Nunc), 45 µl 1× dilution buffer was added to each well and the plate was incubated at 65° C. for 30 min. Plates were chilled for 5 min on ice and then 60 µl substrate was added per well and incubated at room temperature for 20 min. SEAP production was detected using a microplate luminometer (Digene DML 2000). The PsV dilution chosen for the neutralisation assay was one that used the minimum amount of PsVs occurring within the linear range of the titration curve. As the HPV-52 titre was very low, it was re-titred from 1:125 to 1:4000.

Pseudovirion Neutralisation Assay

An in vitro neutralisation assay was used to detect HPV-specific antibody responses in mouse sera and to determine endpoint neutralisation titres.

Controls included:

(a) Cell control (negative infection control): Cells were incubated with neutralisation media only (no sera or pseudovirions) to give a background reading of the cell culture supernatant. The luminescent values associated with this control represented 0% PsV neutralisation.

(b) PsV control (positive PsV infection control): PsVs were pre-incubated in neutralisation buffer prior to cell infection. The values associated with this control represented 100% PsV neutralisation.

(c) MAb or antisera known to neutralise the HPV-type PsV used in the assay (positive neutralisation assay control): PsV's were pre-incubated with 6 dilutions which should span the pre-determined neutralisation titre (0-100% neutralisation).

(d) Pre-bleeds: PsVs were pre-incubated with pooled mouse pre-bleeds (negative control).

The NAb positive controls (Table 8) were titrated prior to the test sera neutralisation assay in order to determine the neutralisation dilution range to be used in the PsV neutralisation assays. The HPV-16, 45 and 52 neutralisation controls were H16.V5, H45.N5, H52.C1 and H52.D11 MAb. The HPV-18 control was rabbit anti-Cervarix sera from our laboratory.

TABLE 8

HPV type-specific neutralising antibodies

| Positive control antibody | HPV type neutralised | Fold dilution | Dilution range |
|---|---|---|---|
| Mouse H16.V5 ascites | HPV-16 | 10-fold | $2 \times 10^2$-$2 \times 10^7$ |
| Rabbit anti-Cervarix sera | HPV-18 | 4-fold | 50-51200 |
| Mouse H45.N5 ascites | HPV-45 | 4-fold | 800-819200 |
| Mouse H52.C1 supernatant | HPV-52 | 10-fold | $2 \times 10^2$-$2 \times 10^7$ |
| Mouse H52.D11 supernatant | HPV-52 | 10-fold | $2 \times 10^2$-$2 \times 10^7$ |

Sera from mice immunized with plant-produced HPV-16 chimaera candidate vaccines were pooled (10 mice/vaccine) and tested for neutralisation of HPV-16, as well as HPV-18, 45 and 52. Pooled vaccine sera was diluted 4-fold in triplicate in the range 1:50 to 1:12800. Pre-bleeds were also pooled and tested in triplicate as a negative control at the lowest dilution of 1:50. Serial dilutions of sera were prepared in sterile non-treated 96-well tissue culture plates (1:10 to 1:2560).

PsVs were diluted in neutralisation buffer to the concentration pre-determined in the titration assay. In another untreated 96-well plate, 1000 diluted PsVs were added to each well and 25 μl of diluted sera (or neutralisation buffer for the PsV control wells) were added to the triplicate wells, resulting in a further 1:5 dilution of pre-diluted sera. The PsVs and sera were incubated at 4° C. for 1 hr to allow for the neutralisation of infectious PsVs, and then 100 μl were added to each well in the pre-plated HEK-293TT plate (neutralisation buffer for the cell control wells). The plates were incubated for a further 72 his in a 37° C. humidified $CO_2$ incubator.

The supernatant was harvested as described above and assayed for the presence of SEAP. The neutralisation titre was stated as the reciprocal of the maximum serum dilution which reduces SEAP activity by at least 50% in comparison to the control sample not pre-incubated with serum.

Results

Humoral Immune Response Against HPV-16 L1

The detection of antibodies elicited against HPV-16 L1 was done by direct ELISA, using insect cell-expressed HPV-16 L1 as the coating antigen (FIG. 9). The anti-L1 titres were expressed as the reciprocal of the maximum serum dilution containing higher absorbance readings than that of the corresponding pre-bleed serum at 1:50.

No anti-L1 response was detected for the L1/L2(56-81) chimaera and the negative control vaccine (V2 and V5; FIG. 9A) as well as the vaccine pre-bleeds (FIG. 9C). In comparison, the ELISA MAbs (H16.V5, CamVir1, FIG. 9B) and the plant-derived L1 positive controls (V4, FIG. 9A) showed a good response and both the plant-derived L1/L2(17-36) and L1/L2(108-120) chimaeras elicited anti-L1 titres of 200 and 12800 respectively (V3 and V1, FIG. 9A). Although HPV-16 L1 elicited the highest anti-L1 titres (12800-51200), L1/L2(108-120) showed a similar response (V4 and V1 respectively, FIG. 9A), suggesting the insertion of the L2 aa 108-120 epitope had less of an effect on L1 immunogenicity in comparison to the other chimaeras. Furthermore, the L1/L2(108-120) and HPV-16 L1 anti-L1 response was statistically significant from their corresponding pre-bleeds and the NSs-infiltrated plant extract (p=0.01).

Humoral Immune Response Against the HPV-16 L2 Epitopes

The anti-L2 response against the E. coli-produced His-tagged HPV-16 L2 protein was determined using western blotting. Individual mouse sera were pooled for each of the vaccines and analysed for anti-L2 responses (FIG. 10).

A non-specific band similar to the ~80 kDa L2 band was detected in both the antisera from the negative vaccine control (V5; plant extract) and the L1 vaccine control (V4; plant-expressed HPV-16 L1) which serves as an additional negative L2 control in this experiment (FIG. 10). All chimaera vaccines (V1-3) appeared to give an anti-L2 response, as strong L2 bands were detected using the chimaera antisera (FIG. 10), However, only the L1/L2(108-120) and L1/L2(17-36) chimaeras (V1 and V3 respectively) gave a definitive anti-L2 response, with L2 bands >2× intensity of HPV-16 L1 (V4).

Neutralisation Assays

Plasmid Analysis

The identity of the pYSEAP and the HPV-16, 18, 45 and 52 L1/L2 pSheLL plasmids was confirmed using restriction enzyme digestion and sequencing (data not shown).

Optiprep Purification and HPV PsV Detection in Purified Fractions

HPV PsVs were purified from the clarified cell supernatant by density gradient ultracentrifugation on a 27-39% Optiprep linear gradient. A light grey band was faintly visible a third of the way up from the gradient and the fractions were collected from the bottom of the tube.

Fractions were screened for the presence of PsVs using HPV type-specific anti-L1 dot blots CamVir1 and rabbit antisera against HPV-16 L2 was used to detect HPV-16 L1 and L2, using Cervarix and E. coli-produced His-tagged HPV-16 L2 as controls. The H16.I23, H45.N5, H52.C1 and H52.D11 MAb were used to detect HPV-18, 45 and 52 respectively, using the initial clarified cell supernatant as the HPV type-specific control (data not shown).

HPV-16 was detected in fraction 3-5 using H16.V5 and weakly detected with the HPV-16 L2 antisera, as the L2 protein is located internally to the L1 capsid surface in co-assembled L1/L2 VLPs (Buck et al., 2008). HPV-18, 45 and 52 L1 was strongly detected in fractions 5-7, 4-6 and 6-10 respectively. PsV fractions were pooled, examined by electron microscopy and used in the neutralisation assays.

Electron Microscopy Analysis

The pooled PsV samples were examined by transmission electron microscopy to determine their assembly, morphology and purification (data not shown). All HPV types assembled into spherical PsVs (55 nm). HPV-45 PsVs appeared to exist exclusively as fully-assembled PsV particles. HPV-16 and 18 PsVs were predominantly assembled, although some capsomeres and aggregates were visible. HPV-52 PsVs contained a large proportion of capsomere aggregates and partial PsVs, possibly as a result of low HPV-52 L1 and L2 expression in the HEK293TT cells.

HPV PsV Titration

The purified PsVs were titrated to determine the PsV dilution to be used for the neutralisation assays. The dilution used was the minimum amount of PsVs giving a robust signal within the linear range of the titration curve.

For HPV-16 and 18 PsVs, the linear range of the titration curve occurred between dilutions 1:250 to 1:1000 (data not shown), and thus 1:500 was chosen for the neutralisation assays. HPV-45 PsVs had the highest titre, with the linear range occurred between dilutions of 1:500 and 1:2000, thus 1:1000 was chosen for further work (data not shown). HPV-52 PsVs had to be re-titred using lower dilutions. The linear range occurred between dilutions 1:125 to 1:250 (data not shown), and a 1:200 dilution was used in the HPV-52 neutralisation assay.

Titration of the Positive Control Neutralising Antibodies

The NAb positive controls were tested prior to the neutralisation assays with the mouse antisera, in order to check their neutralising ability and to determine a suitable dilution range. All positive control antibodies were neutralising and showed a linear relationship within the dilution range tested (Table 9).

TABLE 9

Titration of the positive control neutralising antibodies

| HPV PsV type | Positive control | Dilution range | PsV neutralisation (%) |
|---|---|---|---|
| HPV-16 | H16.V5 | $2 \times 10^2$-$2 \times 10^7$ | 19-100 |
| HPV-18 | anti-Cervarix sera | 50-51200 | 34-99 |
| HPV-45 | H45.N5 | 800-819200 | 29-100 |
| HPV-52 | H52.C1 | $2 \times 10^2$-$2 \times 10^7$ | 0-98 |
|  | H52.D11 | $2 \times 10^2$-$2 \times 10^7$ | 0-98 |

HPV PsV Neutralisation Assays

Sera from mice immunized with plant-produced HPV-16 L1 and L1/L2 chimaeras were tested for homologous neutralisation of HPV-16 PsVs and heterologous cross-protection against HPV-18, 45 and 52 PsVs (FIGS. 10-13). All positive control NAbs successfully neutralised the HPV-16, 18, 45 and 52 PsVs (FIGS. 10-13F), demonstrating that the neutralisation assay results were valid. The neutralisation titre was defined as the highest dilution of serum which reduces SEAP activity by >50% in comparison to the control sample, which was not treated with serum.

HPV-16

The results from the HPV-16 PsV neutralisation assays are shown in FIG. 11. Plant-derived HPV-16 L1 sera (V4; FIG. 11D) mimicked the H16.V5 positive control (FIG. 11F) and strongly neutralised HPV-16 PsV, followed by L1/L2 (108-120) with a similar neutralisation curve (V1; FIG. 11A). Both L1/L2(56-81) and L1/L2(17-36) did not appear to elicit HPV-16 NAb (V2-3; FIG. 11B-C) showing similar neutralisation curves to the negative control (V5; FIG. 11E).

HPV-18

The antisera from all the vaccines did not neutralise HPV-18 PsV (FIG. 12). The L1/L2(56-81) and L1/L2(17-36) chimaeras (V2-3, FIG. 12B-C) produced neutralisation curves similar to the type-specific HPV-16 L1 vaccine and the negative control (V4-5, FIG. 12D-E). L1/L2(108-120) appeared to have some neutralising activity, with reciprocal sera dilutions of <800 reducing luminescent readings below that of the pre-bleed and the unneutralised HPV-18 PsV control (V1; FIG. 12A). However, the chimaera did not reduce SEAP levels by >50%.

HPV-45

The results from the HPV-45 PsV neutralisation assay (FIG. 13) suggest that none of the L1/L2 chimaera vaccines (V1, V2 and V3; FIG. 13A-C) elicited significant titres of HPV-45 NAb, with neutralising curves similar to HPV-16 L1 and the negative vaccine control (V4-5; FIG. 13D-E).

HPV-52

The HPV-52 PsV neutralisation assays (FIG. 14) provide evidence that L1/L2(56-81) sera did not neutralise HPV-52 (L2; FIG. 14C), as seen for HPV-16 L1 and the negative control sera (V4-5; FIG. 14D-E). L1/L2(108-120) and L1/L2(17-36) chimaera vaccines appeared to have some neutralising activity at low reciprocal dilutions (50-200), reducing SEAP levels by >50% in comparison to the unneutralised HPV-52 PsV control (V1 and V3; FIGS. 14A and C).

Although the assay was successful, as shown by the H52.C1 NAb control (FIG. 14F), there was a great deal more variation between triplicates samples and trend lines were difficult to establish. This may be attributed to the partial purification and low concentration of HPV-52 PsVs which may have exaggerated small differences between replicates. The values for the HPV-52 PsV infection control differ between vaccines as V1, V2 and V4 (FIGS. 14A-B and D) were analyzed on a different plate from V3, V5 and H52.C1 (FIGS. 14C and E-F). Time constraints prevented this assay from being repeated.

Table 10 summarizes the HPV-16, 18, 45 and 52 PsV neutralisation antibody titres elicited by the plant-derived vaccines. L1/L2(108-120) elicited homologous HPV-16 NAb and the antisera cross-neutralised heterologous HPV-52 PsV, suggesting this vaccine has the most potential for protection. L1/L2(17-36) chimaeras elicited low levels of cross-neutralising HPV-52 NAb, but homologous HPV-16 NAb were not detected, suggesting the immunogenicity against HPV-16 L1 may be compromised. L1/L2(56-81) did not elicit NAb. None of the HPV vaccines elicited cross-neutralising antibodies against phylogenically-related HPV types 18 and 45.

TABLE 10

Summary of the neutralisation titres for plant-derived L1 and the L1/L2 chimaera candidate vaccines

| Vaccine | Chimaera | PsV neutralisation assay titres* | | | |
|---|---|---|---|---|---|
| | | HPV-16 | HPV-18 | HPV-45 | HPV-52 |
| V1 | L1/L2(108-120) | 50-500 | 0-50 | 0-50 | 50-200 |
| V2 | L1/L2(36-58) | 0-50 | 0-50 | 0-50 | 0-50 |
| V3 | L1/L2(17-36) | 0-50 | 0-50 | 0-50 | 50-200 |
| V4 | HPV-16 L1 | 500-5000 | 0-50 | 0-50 | 0-50 |
| V5 | Plant extract | 0-50 | 0-50 | 0-50 | 0-50 |
| +control | H16.V5 | $2 \times 10^5$-$2 \times 10^6$ | | | |
| | α-CamVir1 | | 12800-51200 | | |
| | H45.N5 | | | 3200-12800 | |
| | H52.C1 | | | | $2 \times 10^4$-$2 \times 10^5$ |
| | H52.D11 | | | | $2 \times 10^5$-$2 \times 10^6$ |

Overview of Vaccine Immunogenicity

The structural assembly (see Example 2 above), the anti-L1 and L2 humoral responses and the HPV-type NAb detected in the L1/L2 chimaera antisera are summarized in Table 11. Assembly into VLPs appears to be associated with higher anti-L1 and HPV-16 PsV neutralisation titres, suggesting assembly is associated with L1 immunogenicity.

TABLE 11

Antibody responses for the L1 and L1/L2 chimaeric vaccines

| Vaccine | Plant-expressed antigen | TEM structure* | Anti-L1 response** | Anti-L1 titres | Anti-L2 response*** | HPV-16/18/45/52 neutralisation |
|---|---|---|---|---|---|---|
| V1 | L1/L2(108-120) | VLPs | Y | 12800 | Y | HPV-16/52 |
| V2 | L1/L2(56-81) | C/CA | N | 0-50 | N | None |
| V3 | L1/L2(17-36) | CA/VLPs | Y | 200 | Y | HPV-52 |
| V4 | HPV-16 L1 (+) | VLPs | Y | >12800 | N | HPV-16 |
| V5 | Plant extract (−) | N/A | N | 0-50 | N | None |

*TEM antigen assembly: C = capsomeres, CA = capsomere aggregates, VLPs = virus-like particles.
**ELISA detection of anti-L1 antibodies. Y = yes, N = no.
***Western blot detection of anti-L2 antibodies.

Discussion

Plant-derived HPV-16 L1 (Maclean et al., 2007; Fernández-San Millán et al., 2008) and L1-based chimaeras (Paz De la Rosa et al., 2009) assemble into immunogenic VLPs and elicit the production of neutralising antibodies (NAb). In this study, the immunogenicity of three plant-derived L1/L2 chimaeras containing cross-neutralising HPV-16 L2 aa 108-120, 56-81 or 17-36 epitopes in the h4 region of HPV-16 L1 were analysed. Mice were subcutaneously immunized with 10 μg of plant-derived antigen in Freund's incomplete adjuvant, and received 4 booster vaccinations within 7 weeks.

Humoral Immune Responses

The humoral anti-L1 and L2 responses elicited by the plant-derived L1/L2 chimaeras were analysed in this study, to determine if the L2 peptides are displayed and whether the L2 insertions compromise L1 immunogenicity.

The detection of L1 and L2 antibodies in mouse antisera was done by direct ELISA (FIG. 9) and western blotting (FIG. 10) respectively, using either insect cell-expressed HPV-16 L1 or E. coli-expressed His-tagged L2 antigen. Plant-derived HPV-16 L1 served as the anti-L1 positive control in the study and elicited the highest anti-L1 response, with titres of 12800-51200 (FIG. 9A). These results are similar to other mouse immunogenicity studies using partially-purified plant-derived HPV-16 L1 VLPs (Titres=20000-40960; Maclean et al., 2007; Fernández-San Millán et al., 2008).

The negative control vaccine (V5: NSs-infiltrated plant extract) and the vaccine pre-bleeds (V1-5 PB) did not give anti-L1 responses (FIG. 9). However, antisera from the negative controls (V4-5, FIG. 10) did detect the E. coli-expressed His-tagged HPV-16 L2 antigen, thus demonstrating the presence of non-specific antibodies in the sera which bound the His-tagged L2 protein. This is possibly due to the partial purification of antigens, which resulted in the vaccines containing contaminating plant proteins. Nevertheless, the negative control bands were less distinct than the bands for the L1/L2(108-120) and L1/L2(17-36) chimaeras, suggesting these L1/L2 chimaeras elicited an anti-L2 response.

L1/L2(108-120) assembled into distinctive ~30 nm cVLPs and was the most successful chimaera vaccine (Table 11), eliciting the highest anti-L1 response with titres of ~12800 (FIG. 9A) and an anti-L2 response (FIG. 10). Furthermore, only the L1/L2(108-120) and HPV-16 L1 antisera demonstrated significant anti-L1 responses (p=0.01) in comparison to the pre-bleeds and the NSs-infiltrated plant extract (negative control). The insect cell-expressed L1/L2 (108-120) chimaera analysed by Varsani et al. (2003a) elicited higher anti-L1 titres (>204800) in comparison to the plant-derived chimaera, however a 10× higher dose was used (100 μg vs. 10 μg). Taken together, there is strong evidence that the L2 aa 108-120 peptide is effectively displayed on the surface of the L1 cVLPs.

The L1/L2(17-36) vaccine elicited a relatively weak anti-L1 response with titres of ~200 (FIG. 9A) but elicited a strong anti-L2 response (FIG. 10), suggesting that the L2 peptide is displayed on the surface of assembled L1. Similarly, fusion of a L2 aa 20-38 peptide to bacterial thioredoxin (Trx) elicited strong anti-L2 responses in comparison to other Trx-L2 peptides comprising of aa 56-120 (Rubio et al., 2009) and the RG-1 MAb directed against the HPV-16 L2 aa 17-36 peptide has been shown to detect L2 in western blotting and ELISA (Gambhira et al., 2007).

The L1/L2(56-81) capsomere vaccine did not elicit a detectable anti-L1 response at the lowest sera dilution 1:50 (FIG. 9A) and the anti-L2 response was inconclusive (FIG. 10), with both the anti-L1 and L2 responses similar to the vaccine pre-bleeds (V1-5 PB) and the negative controls (FIG. 9-10). As a result, plant-derived L1/L2(56-81) do not appear to be immunogenic, unlike E. coli-expressed Trx-L2 fusion peptides (Rubio et al., 2009) and insect cell-expressed L1/L2 chimaeras containing similar L2 epitopes in the DE loop of BPV-1 L1 VLPs (Slupetzkey et al., 2007; Schellenbacher et al., 2009).

Pseudovirion Neutralisation Assays

The L1/L2 chimaeras, containing L2 epitopes aa 108-120, 56-81 and 17-36, were examined for their ability to elicit antibodies which neutralise HPV-16, 18, 45 and 52 PsVs. All of the L2 epitopes analysed in this study have been shown to elicit antibodies which neutralise homologous HPV-16 and cross-neutralise HPV-52 (Kawana et al., 2003; Slupetzky et al., 2007; Kondo et al., 2007, 2008; Gambhira et al., 2007; Schellenbacher et al., 2009). Additionally, L2 aa 56-81 cross-neutralises HPV-18 and L2 aa 17-36 cross-neutralises both HPV-18 and 45 (Gambhira et al., 2007; Kondo et al., 2007, 2008; Alphs et al., 2008; Schellenbacher et al., 2009; Rubio et al., 2009).

HPV-16 was chosen as HPV-16 L1 is the backbone of the chimaeric candidate vaccines and it causes the majority of cervical cancers, followed by phylogenically-related HPV-18 and HPV-45. HPV-16, 18 and 45 are associated with 48%, 23% and 10% of cervical cancers in Africa, and 61%, 10% and 6% of cervical cancers worldwide (de Sanjose et al., 2010). Although HPV-52 is only ranked $5^{th}$ in Africa (3%) and $6^{th}$ worldwide (6%), HPV-52 has been shown to be highly prevalent in low and high-grade cervical lesions in South African women and thus HPV-52 cross-neutralisation is of local significance (Allan et al., 2008).

Homologous HPV-16 Neutralisation

Plant-derived L1/L2(56-81) and L1/L2(17-36) did not elicit detectable HPV-16 NAb titres, giving results similar to the pre-bleeds and the NSs-infiltrated plant extract (FIG. 11). Previous work has shown L1/L2 chimaeras containing HPV-16 L2 peptides aa 17-36, 18-38, 56-75 or 69-81 located in surface regions of BPV-1 or HPV-16 L1 elicited HPV-16 NAb (Slupetzkey et al., 2007; Kondo et al., 2008; Schellenbacher et al., 2009); however, the insertion sites differed from those used in this study and the chimaeras assembled into cVLPs. Furthermore, MAb directed against HPV-16 L2 aa 73-84 were found to be non-neutralising and did not neutralise HPV-16 PsV (Gambhira et al., 2007), similar to the results obtained for the L1/L2(56-81) chimaera in this study.

In this study, only L1/L2(108-120) and HPV-16 L1 neutralised HPV-16 PsV in a similar manner to H16.V5 (positive neutralisation control), giving titres of 50-500 and 500-5000 respectively (Table 10). These results are consistent with other mouse immunogenicity studies using plant-derived HPV L1 antigens. A similar or higher dose of plant-derived HPV-16 L1 VLPs elicited HPV-16 NAb titres of 400-1600 (Maclean et al., 2007; Fernández-San Millán et al., 2008) and plant-derived L1/E6/E7 cVLPS elicited HPV-16 NAb titres of ~400 using a hemagglutination assay (Paz De la Rosa et al., 2009). Furthermore, immunisation of humans with the HPV-16 L2 aa 108-120 peptide has been shown to elicit HPV-16 NAb titres of 100-1000 (Kawana et al., 2003) and mouse antisera from L1/L2 chimaeras containing the L2 epitopes aa 108-120 (Slupetzkey et al., 2007) or L2 aa 75-112 and 115-154 (Schellenbacher et al., 2009) neutralised homologous HPV-16 PsVs with titres<1000. Therefore the titres obtained in the study are within the range reported by L1/L2 chimaera vaccines produced in other expression systems.

Heterologous HPV-18, 45 and 52 Neutralisation

Neutralising activity against phylogenically-related HPV-18 and 45 PsV was not detected for all the HPV vaccines (FIG. 12-13). Similarly, the L1/L2(56-81) antisera did not neutralise HPV-52 PsV (FIG. 14). Although L1/L2(108-120) and L1/L2(17-36) appeared to elicit low HPV-52 NAb titres (50-200), there was a great deal of variation in the assay, possibly due to the purification of partially-assembled PsVs, and the assay should be repeated to confirm results.

Previous work has demonstrated that L1/L2 chimaeras containing the L2 aa 56-81 peptide cross-neutralises both HPV-18 and 52 (Kondo et al., 2008). However, the chimaeras were assembled into cVLPs unlike L1/L2(56-81), suggesting VLP assembly is important to induce the production of high NAb titres. Furthermore, L1/L2 chimaera containing L2 aa 17-36 or 18-36 (Kondo et al., 2008; Schellenbacher et al., 2009) elicits NAb against HPV-18, 45 and 52. However, the L2 peptides were inserted into the DE loop (Schellenbacher et al., 2009) and the dosage was not stated for the study conducted by Kondo et al. (2008). In this study, the low HPV-52 NAb titres elicited by plant-derived L1/L2(17-36) in mice were comparable to titres elicited by a similar L1/L2 chimaera expressed in insect cells (Schellenbacher et al., 2009), suggesting the expression system does not affect the ability of the antigen to cross-neutralise HPV-52.

Plant-derived L1/L2(108-120) chimaera appeared to elicit HPV-52 NAb and may have potential as a cross-protective HPV vaccine, supported by evidence that the L2 aa 108-120 peptide has been shown to elicit HPV-52 NAb titres of 50-1000 respectively in humans (Kawana et al., 2003). There is no evidence that HPV-16 L2 aa 108-120 cross-neutralises HPV-45, however L1/L2 chimaeras containing similar L2 aa 96-115 or 75-112 epitopes cross-neutralised phylogenically-related HPV-18 (Kondo et al., 2008; Schellenbacher et al., 2009). However NAb titres reported in the studies were low (<100) and it is possible that elicited HPV-18 NAb were too low to detect in the L1/L2(108-120) antisera.

REFERENCES

Aires, K. A. et al., (2006) *Appl. Environ. Microbial.* 72, 745-52.
Allan, B. et al., (2008) *J. Clin. Microbial.* 46, 740-2.
Alphs, H. H. et al., (2008) *Proc. Natl. Acad. Sci. U.S.A.* 105, 5850-5.
Baek, J. O. et al., (2011) *Protein Expr. Purif.* 75, 211-7.
Bazan, S. B. et al., (2009) *Arch. Virol.* 154, 1609-17.
Biemelt, S. et al., (2003) *J. Virol.* 77, 9211-20.
Bishop, B. et al., (2007) *Virol. J.* 4, 3.
Breitburd, F. et al., (1995) *J. Virol.* 69, 3959-63.
Brown, D. R. et al., (2009) *J. Infect. Dis.* 199, 926-35.
Buck, C. B. et al., (2005) *Methods Mal Med,* 119, 445-62.
Buck, C. B. et al., (2008) *J. Virol.* 82, 5190-7.
Carter, J. J. et al., (1991) *Virology* 182, 513-21.
Carter, J. J. et al., (2003) *J. Virol.* 77, 11625-32.
Chen, X. S. et al., (2000) *Mol. Cell.* 5, 557-67.
Christensen, N. D. et al., (1996) *Virology* 223, 174-84.
Christensen, N.D. et al., (2001) *Virology* 291, 324-34.
Cook, J.C. et al., (1999) *Protein Expr. Purif.* 17, 477-84.
de Carvalho, F. et al., (1992) *EMBO J.* 11, 2595-602.
de Sanjosé, S. et al., (2010) *Lancet Oncol.* 11, 1048-56.
Embers, M. E. et al., (2002) *J. Virol.* 76, 9798-805.
Ferlay, J. et al., (2010) *Int. J. Cancer* 127, 2893-917.
Fernández-San Millán, A. et al., (2008) *Plant Biotechnol. J.* 6, 427-41.
Fischer, R. et al., (2004) *Curr. Opin. Plant Biol.* 7, 152-8.
Fleury, M. J. et al., (2009) *Protein Sci.* 18, 1425-38.
Fligge, C. et al., (2001) *Virology* 283, 353-7.
FUTURE II Study Group (2007) *J. Infect. Dis.* 196, 1438-46.
Gambhira, R. et al., (2007) *J. Virol.* 81, 13927-31.
Hagensee, M. E. et al., (1993) *J. Virol.* 67, 315-22.
Heidebrecht, F. et al., (2009) *J. Immunol. Methods* 345, 40-8.
Johnson, K. M. et al., (2009) *J. Virol.* 83, 2067-74.
Joura, E. A. et al., (2007) *Lancet* 369, 1693-702.
Joyce, J. G. et al., (1999) *J. Biol. Chem.* 274, 5810-22.
Kawana, K. et al., (1999) *J. Virol.* 73, 6188-90.
Kawana, K. et al., (2003) *Vaccine* 21, 4256-60.
Kim, H.J. et al., (2009) *Arch. Pharm. Res.* 32, 1759-66.
Kim, H.J. et al., (2010) *Protein Expr Purif* 70, 68-74.
Kirnbauer, R. et al., (1992) *Proc. Natl. Acad. Sci. U.S.A.* 89, 12180-4.
Koh, Y. T. et al., (2006) *J. Transl. Med.* 4, 42.
Kohl, T. O. et al., (2007) *BMC Biotechnol.* 7, 56.
Kondo, K. et al., (2007) *Virology* 358, 266-72.
Kondo, K. et al., (2008) *J. Med. Virol.* 80, 841-6.
Lenzi, P. et al., (2008) *Transgenic Res.* 17, 1091-102.
Li, M. et al., (1997) *J. Virol.* 71, 2988-95.
Li, M. et al., (1998) *J. Virol.* 72, 2160-7.
Mach, H. et al., (2006) *J. Pharm. Sci.* 95, 2195-206.
Maclean, J. et al., (2007) *J. Gen. Virol.* 88, 1460-9.
McCarthy, M. P. et al., (1998) *J. Virol.* 72, 32-41.
McLean, C. S. et al., (1990) *J. Clin. Pathol.* 43, 488-92.
Meins, F. Jr. (2000) *Plant Mol. Biol.* 43, 261-73.
Muñoz, N. et al., (2003) *N. Engl. J. Med.* 348, 518-27.
Muñoz, N. et al., (2004) *Int. J. Cancer* 111, 278-285.
Murata, Y. et al., (2009) *Virol J.* 6, 81.
Obembe, O. O. et al., (2011) *Biotechnol. Adv.* 29, 210-22.
Parkin, D. M. and Bray, F. (2006) *Vaccine* 24, S3/11-25.
Paz De la Rosa, G. et al., (2009) *Virol. J.* 6, 2.

Regnard, G. L. et al., (2010) *Plant Biotechnol. J.* 8, 38-46.
Robinson, C. and Ellis, R. J. (1984) *Eur J Biochem.* 142, 337-42.
Rubio, I. et al., (2009) *Vaccine* 27, 1949-56.
Rybicki, E. P. (2009) *Drug Discov. Today* 14, 16-24.
Ryding, J. et al., (2007) *J. Gen. Virol.* 88, 792-802.
Sambrook, J. et al., (1989) Cold Spring Harbor Laboratory Press, New York.
Sapp, M. et al., (1998) *J. Virol.* 72, 6186-9.
Sasagawa, T. et al., (1995) *Virology* 206, 126-35.
Schellenbacher, C. et al., (2009) *J. Virol.* 83, 10085-95.
Schiller, J. T. et al., (2008) *Vaccine* 26, K53-61.
Shen, W. J. and Forde, B. G. (1989) *Nucleic Acids Res.* 17, 8385.
Sijen, T. and Kooter, J. M. (2000) *Bioassays* 22, 520-31.
Slupetzky, K. et al., (2007) *Vaccine* 25, 2001-10.
Studentsov, Y. Y. et al., (2002) *J. Olin. Microbiol.* 40, 1755-60.
Sun, X. Y. et al., (1995) *Virology* 213, 321-7.
Suzich, J. A. et al, (1995) *Proc. Natl. Acad. Sci. U.S.A.* 92, 11553-7.
Takeda, A. et al., (2002) *FEBS Lett.* 532, 75-9.
Thönes, N. et al., (2008) *J. Virol.* 82, 5472-85.
Van Blokland, R. et al., (1994) *Plant J.* 6, 861-877.
Varsani, A. et al., (2003a) *J. Virol.* 77, 8386-93.
Varsani, A. et al., (2003b) *Arch. Virol.* 148, 1771-86.
Varsani, A. et al., (2006a) *Virus Res.* 120, 91-6.
Varsani, A. et al., (2006b) *Virus Res.* 122, 154-63.
Voinnet, O. (2001) *Trends Genet.* 17, 449-59.
Voinnet, O. et al., (2003) *Plant J.* 33, 949-56.
Wang, X. et al., (2003) *Virology* 311, 213-21.
Wheeler, C. M. et al., (2009) *J. Infect. Dis.* 199, 936-44.
White, W. I., et al., (1998) *J. Virol.* 72, 959-64.
White, W. I. et al., (1999) *J. Virol.* 73, 4882-9.
Zhang, W. et al., (1998) *Virology* 243, 423-31.

The invention claimed is:

1. A chimaeric human papillomavirus (HPV) virus like particle (VLP) having a diameter of about 30 nm, wherein the chimaeric HPV VLP is produced according to a method comprising:
(i) providing a chimaeric human codon-optimised nucleotide sequence encoding a chimaeric HPV 16 L1/L2 polypeptide, the chimaeric HPV 16 L1/L2 polypeptide comprising an HPV 16 L1 polypeptide having an HPV L2 peptide of between about 13 amino acids to about 26 amino acids inserted from residue 414 of the HPV 16 L1/L2 polypeptide, wherein the amino acids of the inserted HPV L2 peptide replace the amino acids of the HPV 16 L1 polypeptide;
(ii) cloning the chimaeric human codon-optimised nucleotide sequence into an expression vector adapted to express a polypeptide in a plant;
(iii) transforming or infiltrating a plant cell with the expression vector of step (ii);
(iv) expressing the chimaeric HPV 16 L1/L2 polypeptide in the plant cell of step (iii) such that the expressed chimaeric HPV 16 L1/L2 polypeptide assembles into a chimaeric HPV VLP having a diameter of about 30 nm; and
(v) recovering the chimaeric HPV VLP from the plant cell using a high salt extraction buffer having a NaCl concentration of at least 1M.

2. The chimaeric HPV VLP of claim 1, wherein the inserted HPV L2 peptide is selected from the group consisting of:
(i) a 13 amino acid peptide of SEQ ID NO: 3 encoded by a human codon-optimised nucleotide sequence of SEQ ID NO: 7;
(ii) a 20 amino acid peptide of SEQ ID NO: 5 encoded by a human codon-optimised nucleotide sequence of SEQ ID NO: 9; and
(iii) a 26 amino acid peptide of SEQ ID NO: 4 encoded by a human codon-optimised nucleotide sequence of SEQ ID NO: 8.

3. The chimaeric HPV VLP of claim 1 or 2, wherein the human codon-optimised nucleotide sequence encoding the chimaeric HPV 16 L1/L2 polypeptide is modified to be nuclear localisation signal deficient.

4. The chimaeric HPV VLP of claim 1 or 2, wherein the chimaeric HPV 16 L1/L2 polypeptide comprises an amino acid sequence selected from the group consisting of SEQ ID NO: 22, SEQ ID NO: 23 and SEQ ID NO: 24.

5. The chimaeric HPV VLP of claim 4 wherein the chimaeric HPV 16 L1/L2 polypeptide is encoded by a human codon-optimised nucleotide sequence selected from the group consisting of SEQ ID NO: 26, SEQ ID NO: 27 and SEQ ID NO: 28.

6. The chimaeric HPV VLP of claim 1 or 2, wherein the chimaeric HPV 16 L1/L2 polypeptide is expressed in and recovered from a plant.

7. The chimaeric HPV VLP of claim 6, wherein the chimaeric HPV 16 L1/L2 polypeptide is targeted to a chloroplast of the plant.

8. A method of preventing or treating HPV infection in a subject, the method comprising administering a therapeutically effective amount of the chimaeric HPV VLP of claim 1 or 2 to the subject.

9. A method eliciting an immune response against a chimaeric HPV VLP in a subject, the method comprising administering a therapeutically effective amount of the chimaeric HPV VLP of claim 1 or 2 to the subject.

10. The method of claim 9, wherein the immune response is a neutralising antibody response or a cytotoxic T lymphocyte response.

11. The method of claim 9, wherein the immune response is a cross-protective immune response to multiple HPV types present in the subject.

12. The method of claim 8, wherein the subject is human.

13. A pharmaceutical composition comprising the chimaeric HPV VLP of claims 1 or 2 and a pharmaceutically acceptable carrier or adjuvant.

* * * * *

SEQUENCE LISTING

<160> NUMBER OF SEQ ID NOS: 29

<210> SEQ ID NO 1
<211> LENGTH: 505
<212> TYPE: PRT
<213> ORGANISM: Artificial sequence
<220> FEATURE:
<223> OTHER INFORMATION: Human papilomavirus type 16 L1 polpeptide

<400> SEQUENCE: 1

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240
```

```
Pro Tyr Gly Asp Ser Leu Phe Phe Tyr Leu Arg Arg Glu Gln Met Phe
                245                 250                 255
Val Arg His Leu Phe Asn Arg Ala Gly Ala Val Gly Glu Asn Val Pro
            260                 265                 270
Asp Asp Leu Tyr Ile Lys Gly Ser Gly Ser Thr Ala Asn Leu Ala Ser
        275                 280                 285
Ser Asn Tyr Phe Pro Thr Pro Ser Gly Ser Met Val Thr Ser Asp Ala
    290                 295                 300
Gln Ile Phe Asn Lys Pro Tyr Trp Leu Gln Arg Ala Gln Gly His Asn
305                 310                 315                 320
Asn Gly Ile Cys Trp Gly Asn Gln Leu Phe Val Thr Val Val Asp Thr
                325                 330                 335
Thr Arg Ser Thr Asn Met Ser Leu Cys Ala Ala Ile Ser Thr Ser Glu
            340                 345                 350
Thr Thr Tyr Lys Asn Thr Asn Phe Lys Glu Tyr Leu Arg His Gly Glu
        355                 360                 365
Glu Tyr Asp Leu Gln Phe Ile Phe Gln Leu Cys Lys Ile Thr Leu Thr
    370                 375                 380
Ala Asp Val Met Thr Tyr Ile His Ser Met Asn Ser Thr Ile Leu Glu
385                 390                 395                 400
Asp Trp Asn Phe Gly Leu Gln Pro Pro Gly Gly Thr Leu Glu Asp
                405                 410                 415
Thr Tyr Arg Phe Val Thr Ser Gln Ala Ile Ala Cys Gln Lys His Thr
            420                 425                 430
Pro Pro Ala Pro Lys Glu Asp Pro Leu Lys Lys Tyr Thr Phe Trp Glu
        435                 440                 445
Val Asn Leu Lys Glu Lys Phe Ser Ala Asp Leu Asp Gln Phe Pro Leu
    450                 455                 460
Gly Arg Lys Phe Leu Leu Gln Ala Gly Leu Lys Ala Lys Pro Lys Phe
465                 470                 475                 480
Thr Leu Gly Lys Arg Lys Ala Thr Pro Thr Thr Ser Ser Thr Ser Thr
                485                 490                 495
Thr Ala Lys Arg Lys Lys Arg Lys Leu
            500                 505

<210> SEQ ID NO 2
<211> LENGTH: 1521
<212> TYPE: DNA
<213> ORGANISM: Artificial Sequence
<220> FEATURE:
<223> OTHER INFORMATION: Human-codon optimised HPV-16 L1

<400> SEQUENCE: 2
atgtccctgt ggctgcccag cgaggccacc gtgtacctgc ccccgtgcc cgtgagcaag      60 gtggtgagca ccgatgagta cgtggcccgg accaacatct actaccacgc cggcacctcc    120
agactgctgg ccgtgggcca ccctacttc cccatcaaga agcccaacaa caacaagatc     180
ctggtgccca aggtgagcgg cctgcaatac cgggtgttca aatccaccct gcccgacccc    240
aataagttcg gcttccccga caccagcttc tacaaccccg acacccagag actggtgtgg    300
gcctgcgtgg gcgtggaggt gggcagaggc cagcctctgg gcgtgggcat cagcggccac    360
cctctgctga caagctgga cgacaccgag aacgccagcg cctacgccgc caacgccggc    420
gtggataaca gagaatgcat cagcatggac tacaagcaga cccagctgtg cctcatcggc    480
tgcaagcccc ccatcggcga gcactggggc aagggcagcc cctgcaccaa cgtggccgtg    540
```

```
aatcctggcg actgtcctcc cctggaactc atcaacaccg tgatccagga cggcgacatg    600
gtggacaccg gcttcggcgc catggacttc accaccctcc aggccaataa gagcgaggtg    660
cccctggaca tctgcaccag catctgcaag taccccgact acatcaagat ggtgagcgag    720
ccctacggcg atagcctgtt cttctacctg cggcgggagc agatgttcgt gcggcacctg    780
ttcaacagag ccggcgccgt gggcgagaac gtgcccgacg acctgtacat caagggcagc    840
ggcagcaccg ccaacctggc cagcagcaac tacttcccta cccccagcgg ctccatggtg    900
accagcgacg cccagatctt caacaagccc tactggctcc agagagccca gggccacaac    960
aatggcatct gctggggcaa ccagctgttc gtgaccgtgg tggataccac ccggagcacc   1020
aacatgtccc tgtgcgccgc catcagcacc agcgagacca cctacaagaa caccaacttc   1080
aaggagtacc tgaggcacgg cgaggagtac gacctccagt tcatcttcca gctgtgcaag   1140
atcaccctca ccgccgacgt gatgacctac atccacagca tgaacagcac catcctggag   1200
gactggaact tcggcctgca gcccctcct ggcggcaccc tggaggacac ctacagattc   1260
gtgaccagcc aggccatcgc atgccagaag cacacccctc ccgcccctaa ggaggacccc   1320
ctgaagaagt acaccttctg ggaggtgaac ctgaaggaga agttcagcgc cgacctggac   1380
cagttccctc tgggcagaaa gttcctgctg aagccggcc tgaaggccaa gcctaagttc   1440
accctgggca agagaaaggc caccccccacc acaagcagca ccagcaccac cgccaagcgg   1500
aagaagcgca agctgtgata g                                              1521
```

<210> SEQ ID NO 3
<211> LENGTH: 13
<212> TYPE: PRT
<213> ORGANISM: Artificial Sequence
<220> FEATURE:
<223> OTHER INFORMATION: HPV L2(108-120) epitope

<400> SEQUENCE: 3

Leu Val Glu Glu Thr Ser Phe Ile Asp Ala Gly Ala Pro
1               5                   10

<210> SEQ ID NO 4
<211> LENGTH: 26
<212> TYPE: PRT
<213> ORGANISM: Artificial sequence
<220> FEATURE:
<223> OTHER INFORMATION: HPV L2(56-81) epitope

<400> SEQUENCE: 4

Gly Gly Leu Gly Ile Gly Thr Gly Ser Gly Thr Gly Gly Arg Thr Gly
1               5                   10                  15

Tyr Ile Pro Leu Gly Thr Arg Pro Pro Thr
            20                  25

<210> SEQ ID NO 5
<211> LENGTH: 20
<212> TYPE: PRT
<213> ORGANISM: Artificial sequence
<220> FEATURE:
<223> OTHER INFORMATION: HPV L2(17-36) epitope

<400> SEQUENCE: 5

Gln Leu Tyr Lys Thr Cys Lys Gln Ala Gly Thr Cys Pro Pro Asp Ile
1               5                   10                  15

Ile Pro Lys Val
            20

<210> SEQ ID NO 6
<211> LENGTH: 88
<212> TYPE: PRT
<213> ORGANISM: Artificial sequence
<220> FEATURE:
<223> OTHER INFORMATION: L2 BPV (1-88) epitope

<400> SEQUENCE: 6

```
Met Ser Ala Arg Lys Arg Val Lys Arg Ala Ser Ala Tyr Asp Leu Tyr
1               5                   10                  15

Arg Thr Cys Lys Gln Ala Gly Thr Cys Pro Pro Asp Val Ile Pro Lys
            20                  25                  30

Val Glu Gly Asp Thr Ile Ala Asp Lys Ile Leu Lys Phe Gly Gly Leu
        35                  40                  45

Ala Ile Tyr Leu Gly Gly Leu Gly Ile Gly Thr Trp Ser Thr Gly Arg
    50                  55                  60

Val Ala Ala Gly Gly Ser Pro Arg Tyr Thr Pro Leu Arg Thr Ala Gly
65                  70                  75                  80

Ser Thr Ser Ser Leu Ala Ser Ile
                85
```

<210> SEQ ID NO 7
<211> LENGTH: 41
<212> TYPE: DNA
<213> ORGANISM: Artificial sequence
<220> FEATURE:
<223> OTHER INFORMATION: Human codon optimised nucleotide sequence encoding L2(108-120) epitope

<400> SEQUENCE: 7
ctggtggagg agaccagctt catcgacgcc ggagccccccg c                    41

<210> SEQ ID NO 8
<211> LENGTH: 78
<212> TYPE: DNA
<213> ORGANISM: Artificial sequence
<220> FEATURE:
<223> OTHER INFORMATION: Human codon optimised nucleotide sequence encoding L2(56-81) epitope

<400> SEQUENCE: 8
ggcggcctgg gcatcggcac cggcagcggc accggggggca ggaccggcta catcccccctg    60 ggcaccagac cccccacc                                                   78

<210> SEQ ID NO 9
<211> LENGTH: 60
<212> TYPE: DNA
<213> ORGANISM: Artificial sequence
<220> FEATURE:
<223> OTHER INFORMATION: Human codon optimised nucleotide sequence encoding L2(17-36) epitope

<400> SEQUENCE: 9
cagctgtaca agacctgcaa gcaggccggc acctgccccc ctgacatcat ccccaaggtg    60

<210> SEQ ID NO 10
<211> LENGTH: 270
<212> TYPE: DNA
<213> ORGANISM: Artificial sequence
<220> FEATURE:
<223> OTHER INFORMATION: Human codon optimised nucleotide sequence encoding L2 BPV(1-88) epitope

```
<400> SEQUENCE: 10
atgagcgccc ggaagcgggt gaagcgggcc agcgcctacg acctgtaccg gacctgcaag      60
caggccggca cctgcccccc tgacgtgatc cccaaggtgg agggcgacac aatcgccgac     120
aagatcctga agttcggcgg cctggccatc tacctgggcg gcctgggcat tggcacctgg     180
tccaccggca gagtggccgc tggaggaagc cctagataca ccccccctgcg gaccgccggc    240 agcacaagca gcctggccag catctgatga                                      270

<210> SEQ ID NO 11
<211> LENGTH: 22
<212> TYPE: DNA
<213> ORGANISM: Artificial sequence
<220> FEATURE:
<223> OTHER INFORMATION: Oligonucleotide - pTRAc Forward

<400> SEQUENCE: 11
catttcattt ggagaggaca cg                                               22

<210> SEQ ID NO 12
<211> LENGTH: 23
<212> TYPE: DNA
<213> ORGANISM: Artificial sequence
<220> FEATURE:
<223> OTHER INFORMATION: Oligonucleotide - pTRAc Reverse

<400> SEQUENCE: 12
gaactactca cacattattc tgg                                              23

<210> SEQ ID NO 13
<211> LENGTH: 20
<212> TYPE: DNA
<213> ORGANISM: Artificial sequence
<220> FEATURE:
<223> OTHER INFORMATION: Oligonucleotide - ModNew Forward

<400> SEQUENCE: 13
cgacgacctg tacatcaagg                                                  20

<210> SEQ ID NO 14
<211> LENGTH: 19
<212> TYPE: DNA
<213> ORGANISM: Artificial sequence
<220> FEATURE:
<223> OTHER INFORMATION: Oligonucleotide - VEET Reverse

<400> SEQUENCE: 14
gatgaagctg gtctcctcc                                                   19

<210> SEQ ID NO 15
<211> LENGTH: 18
<212> TYPE: DNA
<213> ORGANISM: Artificial sequence
<220> FEATURE:
<223> OTHER INFORMATION: Oligonucleotide - SAF2 Reverse

<400> SEQUENCE: 15
ggatgtagcc ggtcctgc                                                    18

<210> SEQ ID NO 16
<211> LENGTH: 20
<212> TYPE: DNA
<213> ORGANISM: Artificial sequence
<220> FEATURE:
<223> OTHER INFORMATION: Oligonucleotide - QLYK Reverse
```

<400> SEQUENCE: 16
accttgggga tgatgtcagg                                          20

<210> SEQ ID NO 17
<211> LENGTH: 20
<212> TYPE: DNA
<213> ORGANISM: Artificial sequence
<220> FEATURE:
<223> OTHER INFORMATION: Oligonucleotide - SALIBPV Reverse

<400> SEQUENCE: 17
tatctagggc ttcctccagc                                          20

<210> SEQ ID NO 18
<211> LENGTH: 22
<212> TYPE: DNA
<213> ORGANISM: Artificial sequence
<220> FEATURE:
<223> OTHER INFORMATION: Oligonucleotide - L1 Forward

<400> SEQUENCE: 18
tgaccttatg ggactttcct ac                                       22

<210> SEQ ID NO 19
<211> LENGTH: 19
<212> TYPE: DNA
<213> ORGANISM: Artificial sequence
<220> FEATURE:
<223> OTHER INFORMATION: Oligonucleotide - L1 Reverse

<400> SEQUENCE: 19
caccataagc agccacaat                                           19

<210> SEQ ID NO 20
<211> LENGTH: 19
<212> TYPE: DNA
<213> ORGANISM: Artificial sequence
<220> FEATURE:
<223> OTHER INFORMATION: Oligonucleotide - L2 Forward

<400> SEQUENCE: 20
taccaccacg aacaagcac                                           19

<210> SEQ ID NO 21
<211> LENGTH: 18
<212> TYPE: DNA
<213> ORGANISM: Artificial sequence
<220> FEATURE:
<223> OTHER INFORMATION: Oligonucleotide - L2 Reverse

<400> SEQUENCE: 21
aagccatacg ggaagcaa                                            18

<210> SEQ ID NO 22
<211> LENGTH: 505
<212> TYPE: PRT
<213> ORGANISM: Artificial sequence
<220> FEATURE:
<223> OTHER INFORMATION: Chimaeric HPV L1/L2(108-120) polypeptide

<400> SEQUENCE: 22

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn

```
                 20                  25                  30
Ile Tyr Tyr His Ala Gly Thr Ser Arg Leu Leu Ala Val Gly His Pro
             35                  40                  45

Tyr Phe Pro Ile Lys Lys Pro Asn Asn Asn Lys Ile Leu Val Pro Lys
 50                  55                  60

Val Ser Gly Leu Gln Tyr Arg Val Phe Arg Ile His Leu Pro Asp Pro
 65                  70                  75                  80

Asn Lys Phe Gly Phe Pro Asp Thr Ser Phe Tyr Asn Pro Asp Thr Gln
                 85                  90                  95

Arg Leu Val Trp Ala Cys Val Gly Val Glu Val Gly Arg Gly Gln Pro
                100                 105                 110

Leu Gly Val Gly Ile Ser Gly His Pro Leu Leu Asn Lys Leu Asp Asp
            115                 120                 125

Thr Glu Asn Ala Ser Ala Tyr Ala Ala Asn Ala Gly Val Asp Asn Arg
            130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
                180                 185                 190

Thr Val Ile Gln Asp Gly Asp Met Val Asp Thr Gly Phe Gly Ala Met
            195                 200                 205

Asp Phe Thr Thr Leu Gln Ala Asn Lys Ser Glu Val Pro Leu Asp Ile
            210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
                260                 265                 270

Asp Asp Leu Tyr Ile Lys Gly Ser Gly Ser Thr Ala Asn Leu Ala Ser
            275                 280                 285

Ser Asn Tyr Phe Pro Thr Pro Ser Gly Ser Met Val Thr Ser Asp Ala
290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
            370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Val Glu
                405                 410                 415

Glu Thr Ser Phe Ile Asp Ala Gly Ala Pro Ala Cys Gln Lys His Thr
            420                 425                 430

Pro Pro Ala Pro Lys Glu Asp Pro Leu Lys Lys Tyr Thr Phe Trp Glu
            435                 440                 445
```

```
Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505

<210> SEQ ID NO 23
<211> LENGTH: 505
<212> TYPE: PRT
<213> ORGANISM: Artificial sequence
<220> FEATURE:
<223> OTHER INFORMATION: Chimaeric HPV L1/L2(56-81) polypeptide

<400> SEQUENCE: 23

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300
```

```
Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
            325                 330                 335

Thr Arg Ser Thr Asn Met Ser Leu Cys Ala Ala Ile Ser Thr Ser Glu
        340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
        370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Gly Gly Leu
            405                 410                 415

Gly Ile Gly Thr Gly Ser Gly Thr Gly Gly Arg Thr Gly Tyr Ile Pro
            420                 425                 430

Leu Gly Thr Arg Pro Pro Thr Pro Leu Lys Lys Tyr Thr Phe Trp Glu
        435                 440                 445

Val Asn Leu Lys Glu Lys Phe Ser Ala Asp Leu Asp Gln Phe Pro Leu
450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
            485                 490                 495

Thr Ala Lys Arg Lys Lys Arg Lys Leu
            500                 505

<210> SEQ ID NO 24
<211> LENGTH: 505
<212> TYPE: PRT
<213> ORGANISM: Artificial sequence
<220> FEATURE:
<223> OTHER INFORMATION: Chimaeric HPV L1/L2(17-36) polypeptide

<400> SEQUENCE: 24

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
            85                  90                  95

Arg Leu Val Trp Ala Cys Val Gly Val Glu Val Gly Arg Gly Gln Pro
        100                 105                 110

Leu Gly Val Gly Ile Ser Gly His Pro Leu Leu Asn Lys Leu Asp Asp
    115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160
```

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Thr Gln Leu Tyr
                405                 410                 415

Lys Thr Cys Lys Gln Ala Gly Thr Cys Pro Pro Asp Ile Ile Pro Lys
            420                 425                 430

Val Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
                500                 505

<210> SEQ ID NO 25
<211> LENGTH: 501
<212> TYPE: PRT
<213> ORGANISM: Artificial sequence
<220> FEATURE:
<223> OTHER INFORMATION: Chimaeric HPV L1/L2 BPV(1-88) polypeptide

<400> SEQUENCE: 25

Met Ser Leu Trp Leu Pro Ser Glu Ala Thr Val Tyr Leu Pro Pro Val
1               5                   10                  15

-continued

Pro Val Ser Lys Val Ser Thr Asp Glu Tyr Val Ala Arg Thr Asn
              20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Met Ser Ala
                405                 410                 415

Arg Lys Arg Val Lys Arg Ala Ser Ala Tyr Asp Leu Tyr Arg Thr Cys
            420                 425                 430

```
Lys Gln Ala Gly Thr Cys Pro Pro Asp Val Ile Pro Lys Val Glu Gly
            435                 440                 445

Asp Thr Ile Ala Asp Lys Ile Leu Lys Phe Gly Gly Leu Ala Ile Tyr
    450                 455                 460

Leu Gly Gly Leu Gly Ile Gly Thr Trp Ser Thr Gly Arg Val Ala Ala
465                 470                 475                 480

Gly Gly Ser Pro Arg Tyr Thr Pro Leu Arg Thr Ala Gly Ser Thr Ser
            485                 490                 495

Ser Leu Ala Ser Ile
            500

<210> SEQ ID NO 26
<211> LENGTH: 1521
<212> TYPE: DNA
<213> ORGANISM: Artificial sequence
<220> FEATURE:
<223> OTHER INFORMATION: Human-codon optimised nucleotide sequence
      encoding chimaeric HPV L1/L2(108-120) polypeptide

<400> SEQUENCE: 26
```

| | | | | | |
|---|---|---|---|---|---|
| atgagcctgt | ggctgcccag | cgaggccacc | gtgtacctgc | ccccgtgcc | cgtgagcaag | 60 |
| gtggtgagca | ccgatgagta | cgtggcccgg | accaacatct | actaccacgc | cggcacctcc | 120 |
| agactgctgg | ccgtgggcca | ccctacttc | cccatcaaga | agcccaacaa | caacaagatc | 180 |
| ctggtgccca | aggtgagcgg | cctgcaatac | cgggtgttca | gaatccacct | gcccgacccc | 240 |
| aataagttcg | gcttccccga | caccagcttc | tacaaccccg | acacccagag | actggtgtgg | 300 |
| gcctgcgtgg | gcgtggaggt | gggcagaggc | cagcctctgg | gcgtgggcat | cagcggccac | 360 |
| cctctgctga | acaagctgga | cgacaccgag | aacgccagcg | cctacgccgc | caacgccggc | 420 |
| gtggataaca | gagaatgcat | cagcatggac | tacaagcaga | cccagctgtg | cctcatcggc | 480 |
| tgcaagcccc | ccatcggcga | gcactgggc | aagggcagcc | cctgcaccaa | cgtggccgtg | 540 |
| aatcctggcg | actgtcctcc | cctggaactc | atcaacaccg | tgatccagga | cggcgacatg | 600 |
| gtggacaccg | gcttcggcgc | catggacttc | accaccctcc | aggccaataa | gagcgaggtg | 660 |
| cccctggaca | tctgcaccag | catctgcaag | taccccgact | acatcaagat | ggtgagcgag | 720 |
| ccctacggcg | atagcctgtt | cttctacctg | cggcgggagc | agatgttcgt | gcggcacctg | 780 |
| ttcaacagag | ccgcgccgt | gggcgagaac | gtgcccgacg | acctgtacat | caagggcagc | 840 |
| ggcagcaccg | ccaacctggc | cagcagcaac | tacttcccta | cccccagcgg | ctccatggtg | 900 |
| accagcgacg | cccagatctt | caacaagccc | tactggctcc | agagagccca | gggccacaac | 960 |
| aatggcatct | gctggggcaa | ccagctgttc | gtgaccgtgg | tggataccac | ccggagcacc | 1020 |
| aacatgtccc | tgtgcgccgc | catcagcacc | agcgagacca | cctacaagaa | caccaacttc | 1080 |
| aaggagtacc | tgaggcacgg | cgaggagtac | gacctccagt | tcatcttcca | gctgtgcaag | 1140 |
| atcaccctca | ccgccgacgt | gatgacctac | atccacagca | tgaacagcac | catcctggag | 1200 |
| gactggaact | tcggcctgca | gccccctcct | ggcggcaccc | tggtggagga | gaccagcttc | 1260 |
| atcgacgccg | gagcccccgc | catgccagaa | gcacacccctc | ccgcccctaa | ggaggacccc | 1320 |
| ctgaagaagt | acaccttctg | ggaggtgaac | ctgaaggaga | agttcagcgc | cgacctggac | 1380 |
| cagttcccctc | tgggcagaaa | gttcctgctg | caagccggcc | tgaaggccaa | gcctaagttc | 1440 |
| accctgggca | agagaaaggc | caccccccacc | acaagcagca | ccagcaccac | cgccaagcgg | 1500 |
| aagaagcgca | agctgtgata | g | | | | 1521 |

<210> SEQ ID NO 27
<211> LENGTH: 1521
<212> TYPE: DNA
<213> ORGANISM: Artificial sequence
<220> FEATURE:
<223> OTHER INFORMATION: Human-codon optimised nucleotide sequence encoding chimaeric HPV L1/L2(56-81) polypeptide

<400> SEQUENCE: 27

```
atgagcctgt ggctgcccag cgaggccacc gtgtacctgc cccccgtgcc cgtgagcaag      60
gtggtgagca ccgatgagta cgtggcccgg accaacatct actaccacgc cggcacctcc     120
agactgctgg ccgtgggcca cccctacttc cccatcaaga agcccaacaa caacaagatc     180
ctggtgccca aggtgagcgg cctgcaatac cgggtgttca gaatccacct gcccgacccc     240
aataagttcg gcttccccga caccagcttc tacaaccccg acacccagag actggtgtgg     300
gcctgcgtgg gcgtggaggt gggcagaggc cagcctctgg gcgtgggcat cagcggccac     360
cctctgctga acaagctgga cgacaccgag aacgccagcg cctacgccgc caacgccggc     420
gtggataaca gagaatgcat cagcatggac tacaagcaga cccagctgtg cctcatcggc     480
tgcaagcccc ccatcggcga gcactggggc aagggcagcc cctgcaccaa cgtggccgtg     540
aatcctggcg actgtcctcc cctggaactc atcaacaccg tgatccagga cggcgacatg     600
gtggacaccg gcttcggcgc catggacttc accaccctcc aggccaataa gagcgaggtg     660
cccctggaca tctgcaccag catctgcaag taccccgact acatcaagat ggtgagcgag     720
ccctacggcg atagcctgtt cttctacctg cggcgggagc agatgttcgt gcggcacctg     780
ttcaacagag ccggcgccgt gggcgagaac gtgcccgacg acctgtacat caagggcagc     840
ggcagcaccg ccaacctggc cagcagcaac tacttcccta cccccagcgg ctccatggtg     900
accagcgacg cccagatctt caacaagccc tactggctcc agagagccca gggccacaac     960
aatggcatct gctggggcaa ccagctgttc gtgaccgtgg tggataccac ccggagcacc    1020
aacatgtccc tgtgcgccgc catcagcacc agcgagacca cctacaagaa caccaacttc    1080
aaggagtacc tgaggcacgg cgaggagtac gacctccagt tcatcttcca gctgtgcaag    1140
atcaccctca ccgccgacgt gatgacctac atccacagca tgaacagcac catcctggag    1200
gactggaact tcggcctgca gccccctcct ggcggcacag gcggcctggg catcggcacc    1260
ggcagcggca ccgggggcag gaccggctac atcccccctgg gcaccagacc ccccaccccc    1320
ctgaagaagt acaccttctg ggaggtgaac ctgaaagaga agttcagcgc cgacctggac    1380
cagttccctc tgggccggaa gttcctgctc caggctgggc tgaaggccaa gcccaagttc    1440
accctgggca agcggaaggc cacccccacc acctccagca ccagcaccac cgccaagcgg    1500
aagaaacgga agctgtgatg a                                              1521
```

<210> SEQ ID NO 28
<211> LENGTH: 1521
<212> TYPE: DNA
<213> ORGANISM: Artificial sequence
<220> FEATURE:
<223> OTHER INFORMATION: Human-codon optimised nucleotide sequence encoding chimaeric HPV L1/L2(17-36) polypeptide

<400> SEQUENCE: 28

```
atgagcctgt ggctgcccag cgaggccacc gtgtacctgc cccccgtgcc cgtgagcaag      60
gtggtgagca ccgatgagta cgtggcccgg accaacatct actaccacgc cggcacctcc     120
agactgctgg ccgtgggcca cccctacttc cccatcaaga agcccaacaa caacaagatc     180
```

```
ctggtgccca aggtgagcgg cctgcaatac cgggtgttca gaatccacct gcccgacccc

-continued

```
ccctggaca  tctgcaccag  catctgcaag  taccccgact  acatcaagat  ggtgagcgag    720
ccctacggcg  atagcctgtt  cttctacctg  cggcgggagc  agatgttcgt  gcggcacctg    780
ttcaacagag  ccggcgccgt  gggcgagaac  gtgcccgacg  acctgtacat  caagggcagc    840
ggcagcaccg  ccaacctggc  cagcagcaac  tacttcccta  cccccagcgg  ctccatggtg    900
accagcgacg  cccagatctt  caacaagccc  tactggctcc  agagagccca  gggccacaac    960
aatggcatct  gctggggcaa  ccagctgttc  gtgaccgtgg  tggataccac  ccggagcacc   1020
aacatgtccc  tgtgcgccgc  catcagcacc  agcgagacca  cctacaagaa  caccaacttc   1080
aaggagtacc  tgaggcacgg  cgaggagtac  gacctccagt  tcatcttcca  gctgtgcaag   1140
atcaccctca  ccgccgacgt  gatgacctac  atccacagca  tgaacagcac  catcctggag   1200
gactggaact  tcggcctgca  gcctccccct  ggcggcacca  tgagcgcccg  gaagcgggtg   1260
aagcgggcca  gcgcctacga  cctgtaccgg  acctgcaagc  aggccggcac  ctgcccccct   1320
gacgtgatcc  ccaaggtgga  gggcgacaca  atcgccgaca  agatcctgaa  gttcggcggc   1380
ctggccatct  acctgggcgg  cctgggcatt  ggcacctggt  ccaccggcag  agtggccgct   1440
ggaggaagcc  ctagatacac  cccctgcgg  accgccggca  gcacaagcag  cctggccagc   1500
atctgatga                                                               1509
```